US006458158B1

(12) United States Patent
Anderson et al.

(10) Patent No.: US 6,458,158 B1
(45) Date of Patent: Oct. 1, 2002

(54) COMPOSITE BONE GRAFT, METHOD OF MAKING AND USING SAME

(75) Inventors: Billy G. Anderson, Virginia Beach, VA (US); Lloyd Wolfinbarger, Jr., Norfolk, VA (US)

(73) Assignee: LifeNet, Virginia Beach, VA (US)

( * ) Notice: Subject to any disclaimer, the term of this patent is extended or adjusted under 35 U.S.C. 154(b) by 0 days.

(21) Appl. No.: 09/699,029

(22) Filed: Oct. 27, 2000

Related U.S. Application Data

(63) Continuation-in-part of application No. 09/286,975, filed on Apr. 6, 1999, now abandoned, which is a continuation-in-part of application No. 09/225,299, filed on Jan. 5, 1999, now abandoned.

(51) Int. Cl.[7] ................................................. A61F 2/28
(52) U.S. Cl. .................................. 623/16.11; 623/11.11
(58) Field of Search ........................... 623/11.11, 16.11; 606/70

(56) References Cited

U.S. PATENT DOCUMENTS

| | | | | |
|---|---|---|---|---|
| 4,512,038 A | * | 4/1985 | Alexander et al. | 623/23.75 |
| 5,084,051 A | * | 1/1992 | Tormala et al. | 606/77 |
| 5,152,791 A | * | 10/1992 | Hakamatsuka et al. | 623/16 |
| 5,314,478 A | * | 5/1994 | Oka et al. | 623/18 |
| 5,728,157 A | * | 3/1998 | Prescott | 623/11 |
| 5,769,897 A | * | 6/1998 | Harle | 623/16 |
| 5,876,453 A | * | 3/1999 | Beaty | 623/16 |
| 5,888,227 A | * | 3/1999 | Cottle | 623/17 |
| 5,899,939 A | * | 5/1999 | Boyce et al. | 623/16 |
| 6,123,731 A | * | 9/2000 | Boyce et al. | 623/23.63 |
| 6,241,771 B1 | * | 6/2001 | Gresser et al. | 623/17.16 |

\* cited by examiner

*Primary Examiner*—John J. Wilson
*Assistant Examiner*—Michael B. Priddy
(74) *Attorney, Agent, or Firm*—Susanne Hopkins

(57) ABSTRACT

The invention is directed to a composite bone graft for implantation in a patient, and methods of making and using the composite bone graft, along with methods for treating patients by implanting the composite bone graft at a site in a patient. The composite bone graft includes two or more connected, discrete, bone portions, and includes one or more biocompatible connectors which hold together the discrete bone portions to form the composite bone graft. The composite bone graft may include one or more textured bone surfaces. The textured surface preferably includes a plurality of closely spaced protrusions, preferably closely spaced continuous protrusions. The composite bone graft is useful for repairing bone defects caused by congenital anomaly, disease, or trauma, in a patient, for example, for restoring vertical support of the anterior and/or posterior column. Implantation of the composite bone graft results in improved graft stability and osteoinductivity, without a decrease in mechanical strength. The composite bone graft does not shift, extrude or rotate, after implantation. The present composite bone graft can be appropriately sized for any application and can be used to replace traditional non-bone prosthetic implants.

15 Claims, 22 Drawing Sheets

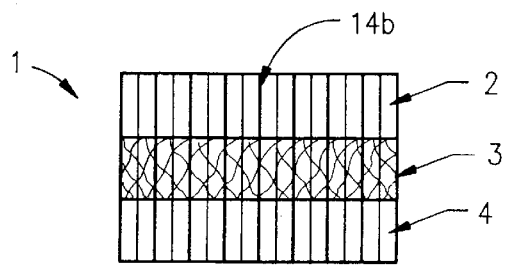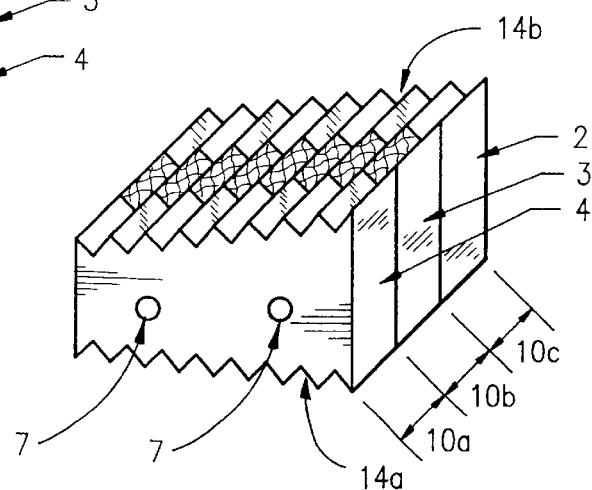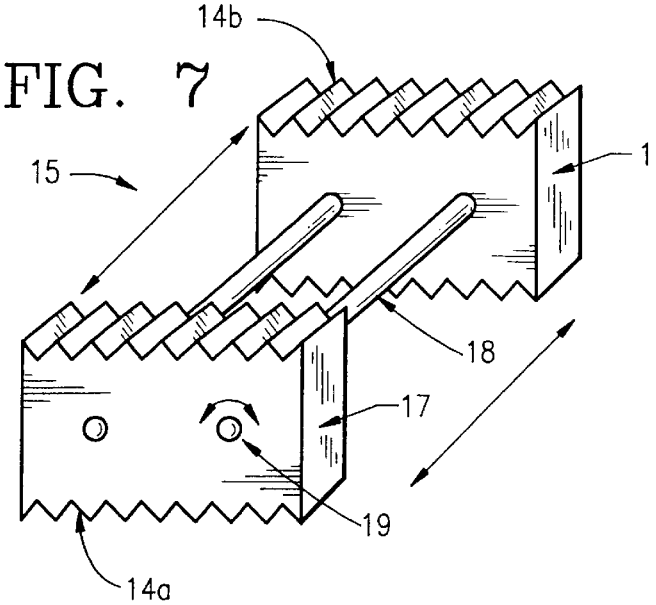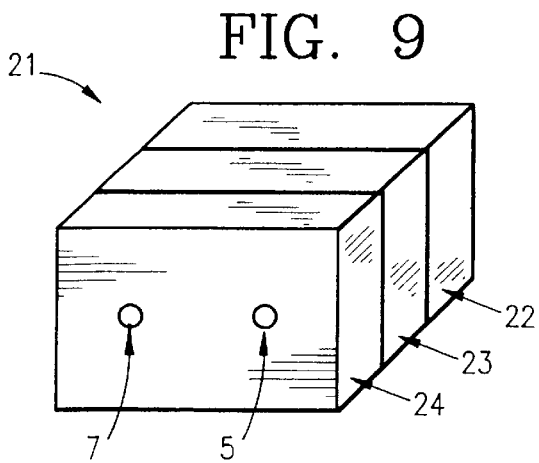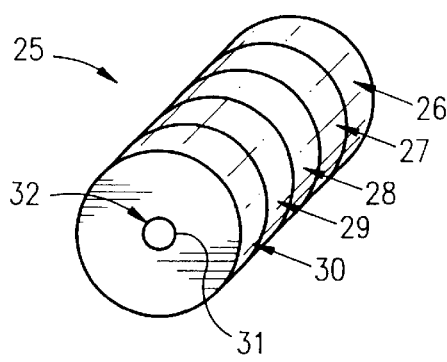

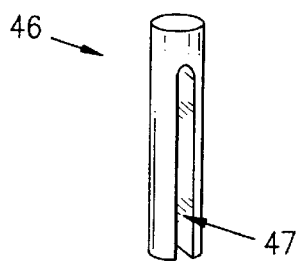
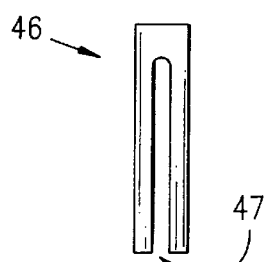
FIG. 16  FIG. 17  FIG. 18
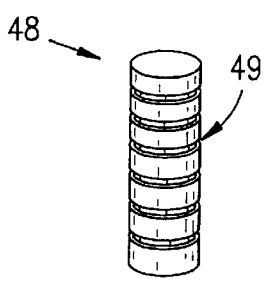
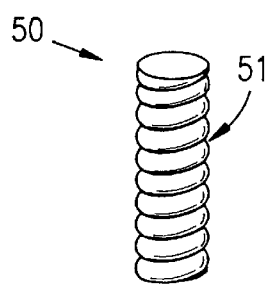
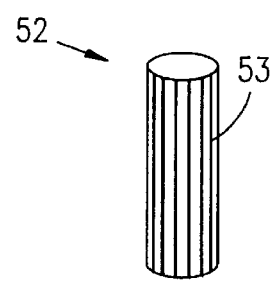
FIG. 19  FIG. 20  FIG. 21
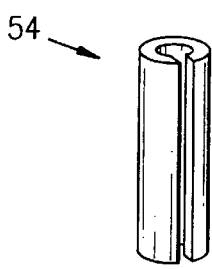
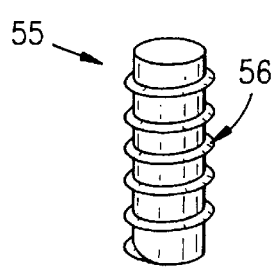
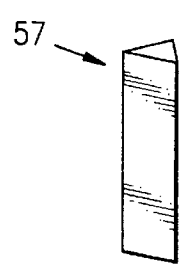
FIG. 22  FIG. 23  FIG. 24
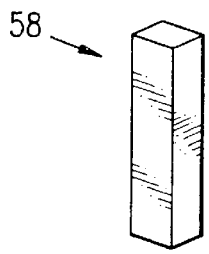
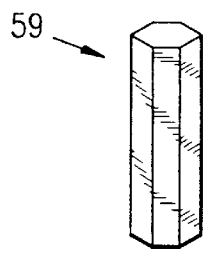
FIG. 25  FIG. 26

COMPOSITE BONE GRAFT, METHOD OF MAKING AND USING SAME

This application is a Continuation-in-Part application of U.S. patent application Ser. No: 09/286,975, filed Apr. 6, 1999, now abandoned which is a Continuation-in-Part of U.S. patent application Ser. No: 09/225,299, filed Jan. 5, 1999, now abandoned.

FIELD OF THE INVENTION

The invention relates to bone grafts and more particularly, to bone grafts useful for spinal fusion. The invention provides a composite bone graft for implantation in a patient, and methods of making and using the composite bone graft. The composite bone graft contains two or more distinct bone portions where the bone portions are connected. The bone portions are preferably self-locking, interlocking, and/or connected by at least one mechanical connector, including for example, a bone pin. One or more of the bone portions may be demineralized, and may also be continuous or discontinuous. The composite bone graft may include one or more textured surfaces, preferably including a plurality of closely spaced protusions. The composite bone graft is useful for repairing bone defects caused by congenital anomaly, disease, or trauma, and is particularly useful for spinal fusions. The composite bone graft can be appropriately sized for any application and can be used to replace traditional non-bone prosthetic implants. The composite bone graft promotes the growth of patient bone at an implantation site by promoting osteoinductivity and cellularization, provides added stability and mechanical strength, and does not shift, extrude or rotate, after implantation.

BACKGROUND OF THE INVENTION

In the field of prosthetic implants, materials often used include bone grafts and implants produced from non-bone materials, including for example stainless steel, titanium and plastics. The choice of whether to use a bone or a non-bone implant often depends on the clinical indication, implant site, whether the implant is load-bearing, and the size of the implant needed.

Prior to the present invention, the use of bone grafts versus non-bone prosthetic implants to for example, support and fuse together adjacent vertebrae, has been limited in part by the physical size of a cortical bone graft. Interbody bone grafting involves the problem of strength. Strong cortical bone (the outer layer) is required as a strut in the interbody position to prevent collapse of the disc space while healing occurs. For example, cortical bone obtained from a cadaver source fashioned into struts, is not wide enough for optimum load bearing. This natural limitation often excludes the use of a bone graft product.

The success or failure of a bone graft further depends on whether the bone graft remains at the implant site, is cellularized, and whether it can withstand the mechanical load. In spinal surgery, there are two primary indications for use of allograft bone: (1) when there is insufficient available autograft bone, and (2) in spinal fusion procedures when a structural element in needed. Typically, bone grafts are affixed at an implant site by fusion. Bone grafts for spinal applications often fail because they are extruded from the implantation site due to shifting, rotation, and slippage of the graft, are not cellularized, or fail mechanically.

The invention enables the use of bone grafts for applications normally suited for only non-bone prosthetic implants.

The invention solves the problem of graft failure by providing a composite bone graft which can be appropriately sized for any application out of for example, strong cortical bone; promotes the ingrowth of patient bone at an implantation site by promoting osteoinductivity and cellularization; provides added stability and mechanical strength; and does not shift, extrude or rotate; after implantation.

SUMMARY OF THE INVENTION

The present invention is directed to a composite bone graft for repairing bone defects caused by congenital anomaly, disease, or trauma, including for example, for restoring vertical support of the posterior and/or anterior colunm. The present composite bone grafts can be used as structural grafts placed posteriorly in the spine as interbody grafts or as strut grafts spanning multiple segments. Posterior composite bone grafts can be used to supplement autologous bone for spinal fusions in patients who lack sufficient host bone and to avoid significant donor site morbidity. The present composite bone grafts can be used for applications normally suited for only non-bone prosthetic implants because the composite bone graft can be appropriately sized for any application and has adequate mechanical strength.

The invention provides a composite bone graft including a plurality of bone portions layered to form a graft unit, and one or more biocompatible connectors for holding together the graft unit.

The invention also provides a composite bone graft including two or more distinct bone portions, and one or more biocompatible connectors, where the biocompatible connectors hold together the two or more bone portions to form the composite bone graft.

The present invention provides a composite bone graft including two or more connected, distinct bone portions.

The present invention provides a composite bone graft including three or more connected, distinct bone portions.

The present invention provides a composite bone graft including three or more connected, distinct cortical bone portions.

The present invention provides a composite bone graft including one or more horizontally disposed channels provided through the composite bone graft perpendicular to the interfaces of the bone portions.

The present invention also provides a composite bone graft including one or more vertically disposed channels provided through the composite bone graft parallel to the interfaces of the bone portions.

The present invention further provides a composite bone graft including one or more horizontally disposed channels and vertically disposed channels where the one or more channels includes one or more therapeutically beneficial substances.

The invention further provides a composite bone graft including two or more connected bone portions, where the bone portions can include cortical bone and cancellous bone.

The invention also provides a composite bone graft, including a first bone portion, a second bone portion, a third bone portion, the first, second and third bone portions are disposed one on the other (ie. layered) to form a graft unit; and one or more biocompatible connectors for holding together the graft unit.

The invention provides a composite bone graft, including a first cortical bone portion, a second cortical bone portion, a cancellous bone portion disposed between the first cortical bone portion and the second cortical bone portion to form a graft unit, and one or more biocompatible connectors for holding together the graft unit.

The invention further provides a composite bone graft, including a first cortical bone portion, a second cortical bone portion provided on the first cortical bone portion to form a graft unit; and one or more biocompatible connectors for holding together the graft unit.

The invention provides a composite bone graft, including a plurality of layered cortical bone portions forming a graft unit, and one or more biocompatible connectors for holding together the graft unit.

The invention provides a composite bone graft, including a plurality of layered bone portions forming a graft unit, and one or more biocompatible connectors for holding together the graft unit.

The invention also provides a composite bone graft, including a first bone portion, a second bone portion provided on the first bone portion to form a graft unit, and one or more biocompatible connectors for holding together the graft unit.

The invention provides a composite bone graft including a plurality of distinct bone portions, where one or more of the bone portions are demineralized.

The invention provides a composite bone graft including a plurality of distinct bone portions, where one or more of the bone portions are continuous or discontinuous.

The invention further provides a composite bone graft including a plurality of distinct bone portions where one or more of the bone portions include a discontinuous bone portion, the discontinuous bone portion including one or more therapeutically beneficial substances including but not limited to, for example, one or more of the following: osteoinductive substances, osteoconductive substances, and pharmaceutically active agents. Such therapeutically beneficial substances may optionally be provided with a carrier. Suitable osteoinductive substances include but are not limited to, for example, autograft bone; allograft bone; Grafton™ produced by Osteotech; DynaGraft™; demineralized cortical bone; demineralized cancellous bone; collagen including one or more growth factors including for example Novus™ produced by Stryker Biotech; collagen including demineralized bone including for example DynaGraft™; cancellous bone; cortical bone; OpteoForm™ produced by the University of Florida; OsteoFill™ produced by the University of Florida; and growth factors including for example, bone morphogenic protein, and transforming growth factor-β. Suitable osteoconductive substances include but are not limited to, for example, hydroxyapitate; collagen; any biocompatible matrix material including for example, polymeric matrix materials, bioglass, bioceramics, resorbable Biomaterials; bioabsorbable polymers; a plastic matrix; stainless steel; titanium; cobalt-chromium-molybdenum alloy matrix; and substances including hydroxyapitate, including for example, Osteoset™ produced by Wright Medical. Suitable pharmaceutically active agents include but are not limited to, for example, growth factors including for example bone growth factors including for example bone morphogenic protein, and transforming growth factor-β, chemotherapeutic agents, anti-inflammatory agents, and antibiotics.

The invention also provides a composite bone graft, including a first cortical bone portion, a second cortical bone portion, a cancellous bone portion disposed between the first cortical bone portion and the second cortical bone portion to form a graft unit, and one or more biocompatible connectors for holding together the graft unit, where the cancellous bone portion is demineralized and discontinuous.

The invention provides a composite bone graft, including a first cortical bone portion, a second cortical bone portion, and a third cortical bone portion disposed between the first cortical bone portion and the second cortical bone portion to form a graft unit, and one or more biocompatible connectors for holding together the graft unit, where the third cortical bone portion is demineralized and discontinuous.

The invention provides a composite bone graft, including a first cortical bone portion, and a second cortical bone portion disposed apart from each other, and forming a graft unit, and one or more biocompatible mechanical connector for holding together the graft unit, where the first and second cortical bone portions are disposed separate from each other by the biocompatible mechanical connectors, thereby forming a substantially void central area.

The invention further provides a composite bone graft including a substantially void central area, where the substantially void central area further includes one or more therapeutically beneficial substances including but not limited to, for example, one or more of the following: osteoinductive substances, osteoconductive substances, and pharmaceutically active agents. Such therapeutically beneficial substances may optionally be provided with a carrier. Suitable osteoinductive substances include but are not limited to, for example, autograft bone; allograft bone; Grafton™ produced by Osteotech; DynaGraft™; demineralized cortical bone; demineralized cancellous bone; collagen including one or more growth factors including for example Novus™ produced by Stryker Biotech; collagen including demineralized bone including for example DynaGraft™; cancellous bone; cortical bone; OpteoForm™ produced by the University of Florida; OsteoFill™ produced by the University of Florida; and growth factors including for example bone morphogenic protein, and transforming growth factorβ. Suitable osteoconductive substances include but are not limited to, for example, hydroxyapitate; collagen; any biocompatible matrix material including for example, polymeric matrix materials, bioglass, bioceramics, resorbable Biomaterials; bioabsorbable polymers; a plastic matrix; stainless steel; titanium; cobalt-chromium-molybdenum alloy matrix; and substances including hydroxyapitate, including for example, Osteoset™ produced by Wright Medical. Suitable pharmaceutically active agents include but are not limited to, for example, growth factors including for example bone growth factors including for example bone morphogenic protein, and transforming growth factorβ; chemotherapeutic agents; anti-inflammatory agents; and antibiotics. The material may be in any suitable form including for example, in the form of a solid, sponge, paste, powder, and/or gel.

The invention further provides a composite bone graft where the biocompatible connectors include one or more mechanical biocompatible connectors.

The invention provides a composite bone graft where the biocompatible connectors include a chemical biocompatible connector.

The invention further provides a composite bone graft where the mechanical biocompatible connectors include one or more pins.

The invention further provides a composite bone graft where the chemical biocompatible connectors include a biocompatible adhesive.

The invention provides a composite bone graft where one or more biocompatible connectors include one or more of the following: a mechanical connector and a chemical connector.

The invention also provides a composite bone graft where the mechanical biocompatible connectors include one or more of the following biocompatible materials: cortical bone; stainless steel; titanium; cobalt-chromium-molybdenum alloy; a bioceramic; a bioglass; a plastic of one or more of the following: nylon, polycarbonate, polypropylene, polyacetal, polyethylene, and polysulfone; and one or more bioabsorbable polymers.

The invention also provides a composite bone graft where the mechanical biocompatible connectors include cortical bone.

The invention provides a composite bone graft where the one or more pins include one or more cortical bone pins.

The invention provides a composite bone graft where the graft unit includes one or more through-holes configured to accomadate the one or more pins.

The invention further provides a composite bone graft where the through-holes are disposed perpendicular to interfaces of bone portions forming the graft unit.

The invention further provides a composite bone graft where the through-holes are disposed perpendicular to interfaces of for example, the first bone portion, the second bone portion, and the third bone portion, of the graft unit.

The invention provides a composite bone graft where the one or more pins and the one or more through-holes are configured to provide an interference fit for holding together the graft unit.

The invention also provides a composite bone graft where the one or more through-holes and the one or more pins are round and an inner diameter of a through-hole is smaller than a diameter of a pin, to provide an interference fit between the through-hole and the pin.

The invention further provides a composite bone graft where the one or more cortical bone pins include a plurality of vertical groves provided on a surface thereof.

The invention further provides a composite bone graft where the one or more cortical bone pins includes a roughened surface.

The invention provides a composite bone graft where the one or more cortical bone pins further includes a slot extending from one end of the bone pin.

The invention provides a composite bone graft where the one or more pins is threaded to provide a threaded engagement with the one or more through-holes.

The invention further provides a composite bone graft where the one or more pins is threaded and the one or more through-holes is threaded, to provide a threaded engagement between the one or more pins and the one or more through-holes.

The invention provides a composite bone graft where the one or more pins and the one or more through-holes are configured to provide a slidable connection, for example, to provide a composite bone graft including a substantially void central area.

The invention also provides a composite bone graft where a cross-section of the one or more pins includes a shape selected from the group including the following: round, ovoid, square, rectangular, triangular, pentagon, hexagon, and trapezoidal.

The invention further provides a composite bone graft including a plurality of plate-like cortical bone portions, the cortical bone portions layered to form a graft unit, the graft unit held together with one or more cortical bone pins.

The invention further provides a composite bone graft where the composite bone graft is a cortical cylinder.

The invention provides a composite bone graft including a graft unit having one or more through-holes configured to accommadate one or more pins, the graft unit including two or more bone portions layered to form the graft unit, and one or more pins for holding together the graft unit.

The invention further provides a composite bone graft, including a graft unit having one or more through-holes configured to accommadate one or more pins, the graft unit including a first plate-like cortical bone, a second plate-like cortical bone, a plate-like cancellous bone disposed between the first plate-like cortical bone and the second plate-like cortical bone to form the graft unit, and one or more cortical bone pins for holding together the graft unit.

The invention also provides a composite bone graft, including a graft unit having one or more through-holes configured to accommadate one or more pins, the graft unit including a first plate-like bone, a second plate-like bone provided on the first plate-like bone to form the graft unit, and one or more bone pins for holding together the graft unit.

The invention also provides a cervical composite bone graft, including a flattened curved wedge graft unit having one or more through-holes configured to accommadate one or more pins, the graft unit including two or more plate-like cortical bone portions layered to form the graft unit, and at least two bone pins for holding together the graft unit, where the graft unit includes a substantially centrally located through-hole. The diameter of the through-hole may be readily selected by one of ordinary skill in the art without undue experimentation depending upon the particular application; for example, the diameter of the through-hole may be from about 2.0 mm–4.0 mm; preferably 2.5 mm–3.0 mm; and more preferably 3.0 mm.

The invention also provides a composite bone graft where the one or more through-holes are disposed perpendicular to interfaces of plate-like bones of the graft unit.

The invention provides a composite bone graft where the composite bone graft is a parallelepiped; a parallel block; a square block; a trapezoid wedge; a cylinder; a tapered cylinder; a cervical wedge (flattened curved wedge); an ovoid wedge (anterior lumbar wedge graft) and a polyhedron.

The invention further provides a composite bone graft where the composite bone graft is a polyhedron including six planer surfaces.

The invention provides a composite bone graft where the composite bone graft further includes one or more textured surfaces.

The invention also provides a composite bone graft where the one or more textured surfaces includes a plurality of closely spaced continuous protrusions.

The invention provides a composite bone graft where the continuous protrusions include a cross-section having one or more shapes selected from the following: irregular; triangular, square, rectangular, and curved.

The invention further provides a composite bone graft where the plurality of continuous protrusions are sized to be in a range of greater than or equal to about 1.5 mm in length; 0.5 to about 10.0 mm in width and 0.1 to about 5.0 mm in depth.

The invention provides a composite bone graft where the plurality of closely spaced continuous protrusions are spaced from about 0.0 to about 3.0 mm apart.

The invention provides a composite bone graft where the plurality of protrusions are spaced from about 0.1 to about 2.0 mm apart.

The invention also provides a composite bone graft where the plurality of protrusions are spaced about 0.5 mm apart.

The invention provides a method for restoring vertical support of the posterior and/or anterior column by implanting a composite bone graft including two or more distinct bone portions held together by one or more connectors, at a site in a patient.

The invention provides a composite bone graft containing two or more connected bone portions, where the composite bone graft has a plurality of closely spaced protrusions on one or more surfaces thereof, where the protrusions are continuous protrusions, discrete protrusions, or a combination thereof.

The invention provides a composite bone graft where the plate-like cortical and/or cancellous bone portions are continuous bone portions and/or discontinuous bone portions.

The invention provides a composite bone graft including one or more discontinuous bone portions.

The invention provides a composite bone graft including one or more discontinuous, demineralized cortical bone portions.

The invention provides a composite bone graft including one or more discontinuous, demineralized cancellous bone portions.

The invention further provides a composite bone graft where one or more continuous or discontinuous cancellous bone portions, (continuous or discontinuous and/or demineralized)includes one or more therapeutically beneficial substances including but not limited to, for example, one or more of the following: osteoinductive substances, osteoconductive substances, and pharmaceutically active agents. Such therapeutically beneficial substances may optionally be provided with a carrier. Suitable osteoinductive substances include but are not limited to, for example, autograft bone; allograft bone; Grafton™ produced by Osteotech; DynaGraft™; demineralized cortical bone; demineralized cancellous bone; collagen including one or more growth factors including for example Novus™ produced by Stryker Biotech; collagen including demineralized bone including for example DynaGraft™; cancellous bone; cortical bone; OpteoForm™ produced by the University of Florida; Osteo-Fill™ produced by the University of Florida; and growth factors including for example bone morphogenic protein, and transforming growth factor-β. Suitable osteoconductive substances include but are not limited to, for example, hydroxyapitate; collagen; any biocompatible matrix material including for example, polymeric matrix materials, bioglass, bioceramics, resorbable Biomaterials; bioabsorbable polymers; a plastic matrix; stainless steel; titanium; cobalt-chromium-molybdenum alloy matrix; and substances including hydroxyapitate, including for example, Osteoset™ produced by Wright Medical. Suitable pharmaceutically active agents include but are not limited to, for example, growth factors including for example bone growth factors including for example bone morphogenic protein, and transforming growth factor-β; chemotherapeutic agents; anti-inflammatory agents; and antibiotics.

The invention provides a composite bone graft where one or more continuous or discontinuous cancellous bone portions are demineralized and include one or more therapeutically beneficial substances.

The invention provides a composite bone graft where one or more discontinuous cortical bone portions, include one or more therapeutically beneficial substances.

The invention further provides a composite bone graft where one or more discontinuous cortical bone portions are demineralized and include one or more therapeutically beneficial substances.

The invention also provides a composite bone graft including a two or more distinct bone portions held together by one or more connectors, where the composite bone graft includes two diametrically opposing chamfered edges, one provided along the length of the graft at its top edge and the other provided along the length of the graft at its bottom edge, such that the chamfered edges are diametrically opposing.

The invention further provides a composite bone graft including two or more distinct interlocking cortical bone portions.

The invention provides a composite bone graft including two or more distinct interlocking bone portions, where the interlocking bone portions are self-locking.

The invention also provides a composite bone graft including two or more distinct interlocking bone portions, where the interlocking bone portions are locked with one or more locking pins.

The invention further provides a composite bone graft where bone portions are locked with one or more locking pins entirely or partially traversing a dimension of the composite bone graft.

The invention provides an interlocking composite bone graft where each complementary bone portion is provided with a discrete or continuous interlocking pattern.

The invention also provides an interlocking composite bone graft including two or more distinct adjacent bone portions where adjacent bone portions are configured to interlock with each other, and one or more bone pins partially or entirely traversing a dimension of the graft, where the dimension of the graft is the length, width, or height of the graft.

The invention provides an interlocking composite bone graft including two or more distinct adjacent bone portions where adjacent bone portions are configured to interlock with each other.

The invention provides a composite bone graft including two or more distinct adjacent interlocking bone portions where adjacent bone portions include complementary peg-like protrusions and corresponding depressions, such that the protrusions and depressions provide an interlocking fit between the bone portions.

BRIEF DESCRIPTION OF THE DRAWINGS

FIG. 1 illustrates a perspective view of a trapezoid wedge composite bone graft having a non-textured surface.

FIG. 2 illustrates a side view of a trapezoid wedge composite bone graft having opposing textured surfaces provided perpendicular to the interfaces of the bone portions. The textured surfaces illustrate continuous linear protrusions defining a saw-tooth-like pattern.

FIG. 3 illustrates a cross-section posterior view of the trapezoid wedge composite bone graft of FIG. 2.

FIG. 4 illustrates a cross-section anterior view of the trapezoid wedge composite bone graft of FIG. 2.

FIG. 5. FIG. 5 illustrates a top view of the trapezoid wedge composite bone graft of FIG. 2, and having a textured surface.

FIG. 6. FIG. 6 is a perspective view of the trapezoid wedge composite bone graft of FIG. 2, and having a textured surface.

FIG. 7. FIG. 7 illustrates a perspective of a preferred slidably connected composite bone graft having a first cortical bone portion, a second cortical bone portion, cortical bone pins, through-holes, and a centrally located void.

FIG. 8. FIG. 8 illustrates a top view of the slidably connected composite bone graft of FIG. 7, having a first cortical bone portion, a second cortical bone portion, and a cancellous bone portion disposed there between.

FIG. 9. FIG. 9 illustrates a perspective view of a preferred embodiment of the composite bone graft.

FIG. 10. FIG. 10 illustrates a preferred cortical dowel composite bone graft including a plurality of cortical bone portions connected by a single cortical bone pin inserted into a through-hole.

FIG. 11A illustrates the method of making a preferred embodiment of the composite bone graft.

FIG. 11B illustrates a method for producing bone pins and producing a pinned graft unit.

FIG. 12 illustrates another method for making a composite bone graft.

FIG. 13A is a perspective view of a preferred trapezoid block composite bone graft having opposing textured surfaces; FIG. 13B is a detail of the protrusions of the textured surface.

FIGS. 14A, 14B and 14C, illustrate a cervical wedge (flattened curved wedge) composite bone graft for use in cervical fusions where 14A is a perspective standing view, 14B is a side view, and 14C is a perspective view where the graft is provided with opposing textured surfaces.

FIG. 15 illustrates a method for making a cervical wedge composite bone graft for use in cervical fusions.

FIG. 16. FIG. 16 illustrates a perspective view of a mechanical pin connector having a slot extending from its lower end.

FIG. 17. FIG. 17 illustrates a side view of the mechanical pin connector of FIG. 16, having a slot extending from its lower end.

FIG. 18. FIG. 18 illustrates a cross-section view of the mechanical pin connector of FIG. 16, having a slot extending from its lower end.

FIG. 19. FIG. 19 illustrates a perspective view of a mechanical pin connector having a plurality of horizontally disposed grooves.

FIG. 20. FIG. 20 illustrates a perspective view of a mechanical pin connector having helical threads.

FIG. 21. FIG. 21 illustrates a perspective view of a mechanical pin connector having a plurality of vertically disposed grooves.

FIG. 22. FIG. 22 illustrates a perspective view of a mechanical slotted pin connector.

FIG. 23. FIG. 23 illustrates a perspective view of a mechanical pin connector having a plurality of horizontally disposed ridges.

FIG. 24. FIG. 24 illustrates a perspective view of a mechanical triangular pin connector.

FIG. 25. FIG. 25 illustrates a perspective view of a mechanical square pin connector FIG. 26. FIG. 26 illustrates a perspective view of a mechanical hexagon pin connector.

FIG. 27 illustrates a perspective view of a rectangular block composite bone graft having a demineralized cortical bone portion sandwiched between two cortical bone portions, where the demineralized cortical bone portion is provided with perforations and channels, and where the composite graft includes opposing textured surfaces provided perpendicular to the interfaces of the bone portions. The textured surfaces illustrate continuous linear protrusions defining a saw-tooth-like pattern.

FIG. 28 illustrates a perspective view of a rectangular block composite bone graft having a demineralized cancellous bone portion sandwiched between two cortical bone portions, where the composite graft includes opposing textured surfaces provided perpendicular to the interfaces of the bone portions. The textured surfaces illustrate continuous linear protrusions defining a saw-tooth-like pattern.

FIG. 29 illustrates a preferred method of making the bone graft of FIG. 27.

FIG. 30 illustrates a preferred method of making the bone graft of FIG. 28.

FIG. 31A illustrates a top view of a composite bone graft including a void disposed between two cortical bone portions where the void includes one or more therapeutically beneficial substances.

FIGS. 32A, 32B, and 32C, illustrate a top view, a cross-section, and a side view, respectively, of a preferred parallel block composite bone graft.

FIGS. 33A, 33B, and 33C, illustrate a top view, a cross-section, and a side view, respectively, of a preferred trapezoid wedge composite bone graft.

FIG. 34 illustrates a perspective view of a preferred trapezoid wedge composite bone graft having opposing textured surfaces and having a horizontally disposed channel and vertically disposed canals.

FIG. 35A illustrates a standing view of a preferred cervical wedge composite bone graft for use in cervical fusions, having horizontally disposed channels and having a centrally located through-hole including an osteo-conductive substance. FIG. 35B illustrates a side view of the cervical wedge graft of FIG. 35A including a vertically disposed channel.

FIGS. 36A, 36B, and 36C, illustrate a cross-section, a top view, and a side view, respectively, of a preferred trapezoid wedge composite bone graft.

FIG. 37 illustrates a standing view of a cervical wedge (flattened curved wedge)composite bone graft for use in cervical fusions.

FIG. 38 illustrates a standing view of a cervical wedge (flattened curved wedge)composite bone graft for use in cervical fusions.

FIG. 39 illustrates a perspective view of a preferred embodiment of the composite bone graft including two interlocking cortical bone portions.

FIG. 40A illustrates a side view of a preferred embodiment of a cervical wedge composite bone graft including two interlocking cortical bone portions, and FIG. 40B illustrates a perspective view of the graft including two interlocking cortical bone portions.

FIG. 41 illustrates a perspective view of a preferred trapezoid wedge bone graft including three interlocking cortical bone portions.

FIGS. 42A, 42B, & 42C illustrate side views of preferred composite bone grafts including two interlocking cortical bone portions where the interlocking interface defines a sawtooth pattern, a stepped pattern and a lock & key pattern respectively.

FIG. 43 illustrates a standing view of a cervical wedge (flattened curved wedge)composite bone graft for use in cervical fusions.

FIG. 44 illustrates a standing view of a cervical wedge (flattened curved wedge)composite bone graft for use in cervical fusions.

DETAILED DESCRIPTION OF THE PREFERRED EMBODIMENTS

I. Definitions

Figure 1:
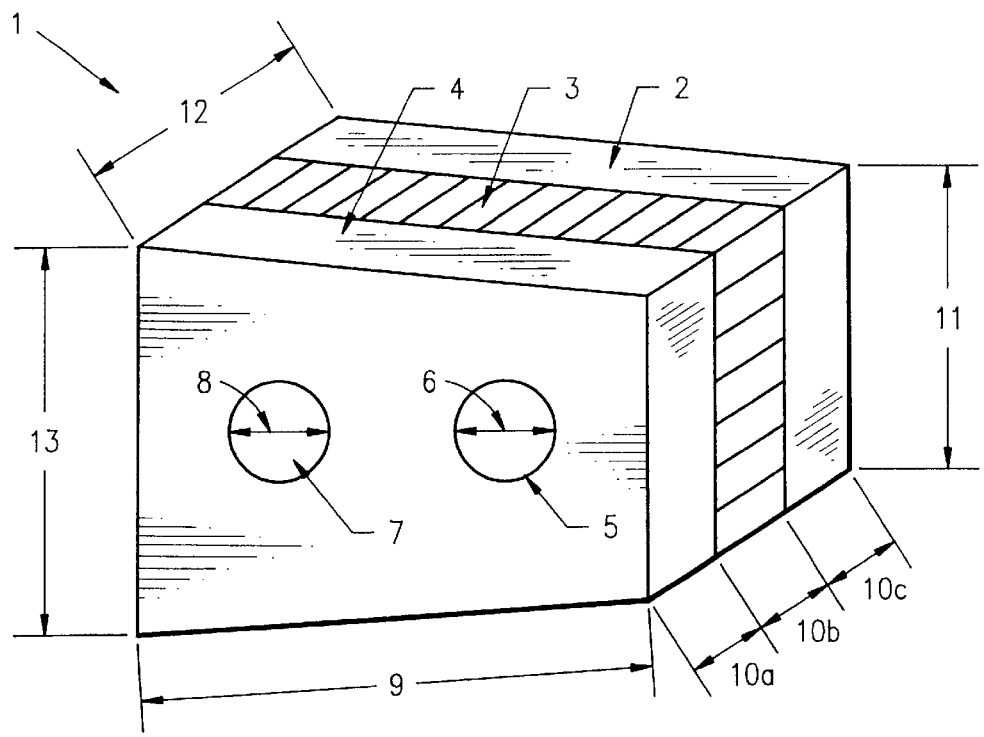
FIG. 1.

The below definitions serve to provide a clear and consistent understanding of the specification and claims, including the scope to be given such terms.

Bioabsorbable polymers. By the term "bioabsorbable polymers" is intended for the purposes of the present invention, bioresorbable, bioabsorbable, biodegradable, and bioerodible materials that are well known to those of ordinary skill in the art and are described in *Biomaterials Science—An Introduction to Materials in Medicine,* edited by Ratner, B. D. et al., Academic Press, (1996), and include for example, the following materials: chitosan; isomorphic ploy(hexamethylene co-trans-1,4-cyclohexane dimethylene oxalates); poly(glycolic acid); copolymers of poly(glycolic acid) and poly(lactic acid); polydioxanone; poly(latic acid); polymers having a back-bone structure selected from the group consisting of: polyanhydrides, polyphophazenes, polyphosphonates, polyamides, and polyiminocarbonates; polyhydroxybutyrate; polyhydroxyvalerate; copolymers of polyhydroxybutyrate and polyhydroxylerate; polycaprolactone; polydioxanone; poly($\gamma$-ethyl glutamate); poly(DTH iminocarbonate); poly(Bisphenol A iminocarbonate); poly(DETOSU-1,6 HD-t-CDM ortho ester); poly(Sebacic acid-hexadecandioic acid anhydride); poly(ortho esters); poly(amino acids); and PLOA. Such polymers may optionally include one or more pharmaceutically active agents for controlled release applications, such agents including for example: osteoinductive factors including for example bone morphogenic protein; growth factors including for example transforming growth factor$\beta$; chemotherapeutic agents; antiobiotics; and anti-inflammatory agents.

Biocompatible. By the term "biocompatible" is intended for the purposes of the present invention, any material which when implanted in a patient does not provoke an adverse response in the patient. A suitable biocompatible material when introduced into a patient is not toxic or injurious to that patient, or does not cause immunological rejection.

Biomechaanical strength. By the term "biomechanical strength" is intended for the purposes of the present invention, those properties exhibited by a bone graft, including loading strength, compressive strength, and tensile strength.

Bone. By the term "bone" is intended for the purposes of the present invention, bone recovered from any source including animal and human, for example, human bone recovered for the production of allografts, and animal bone recovered for the production of xenografts, such allografts and xenografts suitable for implantation into a human. Such bone includes: any bone or portion thereof, including cut pieces of bone, including cortical and/or cancellous bone, for example, recovered from a human including a living human or a cadaver, or animal, and processed for implantation into a living patient. Such bones including for example: the humorous, hemi-pelvi, tibia, fibula, radius, ulna, rib, vertebrae, mandibular, femur, and ilia, and any cut portion thereof. Such bone may be demineralized or not demineralized. In a preferred embodiment a cancellous or cortical bone section is demineralized and disposed between two non-demineralized cortical bone portions. Suitable bone may also include continuous or discontinuous bone portions. For example, one or more bone portions of a composite bone graft may be discontinuous, for example, a bone portion may be perforated and demineralized, for example perforated either before or after demineralization, for example, to allow for uniform demineralization (perforations before demineralization) and to promote ingrowth of patient bone. Cancellous and/or demineralized cancellous and/or discontinuous cancellous and/or demineralized discontinuous cancellous and or discontinuous cortical and/or demineralized discontinuous cortical, bone, may optionally include one or more therapeutically beneficial substances provided with or without a carrier. transforming growth factor$\beta$; The composite bone graft may include a substantially void central area, where the substantially void central area further includes one or more therapeutically beneficial substances provided with or without a carrier. The material may be in any suitable form including for example, in the form of a solid, sponge, paste and/or gel.

Bone marrow elements. By the term "bone marrow elements" is intended for the purposes of the present invention, the highly cellular hematopoietic connective tissue filling the medullary cavities and spongy epiphysis of bone which may harbor bacterial and/or viral particles and/or fungal particles, and includes for example, blood and lipid.

Chamfer. By the term "chamfer" is intended for the purposes of the invention, an oblique face formed at a corner of a composite bone graft, at an angle to the adjacent principal faces. Suitable angles include angles in the range of from 38° to 52°, more preferably 40° to 50°, even more preferably 42° to 48°, and most preferably about 45°.

Cleaned bone. By the term "cleaned bone" is intended for the purposes of the present invention, a bone or cut portion thereof, that has been processed using means known in the art, to remove bone marrow elements.

Closely Spaced. By the term "closely spaced" is intended for the purposes of the present invention, protrusions (discrete or continuous) which are in close proximity to each other. Preferably the protrusions are spaced no more than 3.0 mm apart (i.e. the distance between the edges of two adjacent protrusions), more preferably no more than 2.0 mm apart, even more preferably no more than 1.5 mm apart, and most preferably about 0.5 mm apart.

Composite. By the term "composite" is intended for the purposes of the present invention, a bone graft which is made up of two or more distinct bone portions.

Connector. By the term "connector" is intended for the purposes of the present invention, a means of connecting two or more distinct bone portions, including for example a chemical and/or mechanical means. By the term "mechanical connector" is intended for the purposes of the present invention, a structural member including for example, a pin. By the term "chemical connector" is intended for the purposes of the present invention, a biocompatible composition including for example, one or more biocompatible adhesives and one or more surface modification agents and methods.

Continuous Bone Portion. By the term "continuous bone portion" is intended for the purposes of the present invention, a bone portion that is substantially solid without any artificial void areas.

Figure 2:
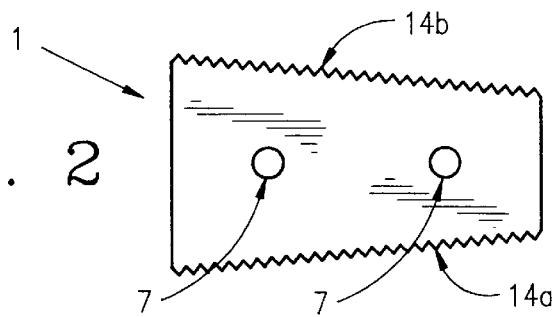
FIG. 2.

Continuous Protrusion. By the term "continuous protrusion" is intended for the purposes of the present invention, a protrusion whose length continues substantially uninterrupted, including for example a linear or curved protrusion whose length is at least three times greater than its width, preferably at least five times greater, and includes for example a continuous, protruding concentric ring, and a continuous linear protrusion for example, as illustrated in FIG. 2. Each continuous protrusion may or may not be distinct from another continuous protrusion.

Demineralized Bone. By the term "demineralized bone" is intended for the purposes of this invention, one or more distinct bone portions which have been demineralized by any method well known to those of ordinary skill in the art. Cortical bone is preferably demineralized in 0.5 to 0.6 N hydrochloric acid for a period of time of from about 1 to about 8 hours, more preferably for a time period of about two hours, at 25° C., to 50° C., more preferably at 25° C. to 37° C. Cancellous bone is preferably demineralized in 0.5 to 0.6N hydrochloric acid for a period of time of from about 20 minutes to about 6.0 hours, more preferably for a time period of from about 30 minutes to about 2.0 hours. Preferably, cortical and/or cancellous bone is demineralized to contain less than 10 wt % residual calcium, more preferably about less than 5 wt % residual calcium, even more preferably about 1 wt % to about 3 wt %, and most preferably about 2 wt % residual calcium. Other methods for demineralizing bone are well known in the art to which the present invention pertains, and can be readily selected and employed by one of ordinary skill in the art, without undue experimentation.

Discontinuous Bone Portion. By the term "discontinuous bone portion" is intended for the purposes of the present invention, a bone portion that contains artificially created void areas including for example, a perforated bone portion, where the perforations or channels may be of any shape and may partially or completely transverse the bone portion. Such perforations may be randomly disposed or disposed in a regular pattern on and/or through the bone portion. Suitable perforations include perforations traversing the width of the bone portion provided perpendicular to the interfaces of the bone portions of the composite graft, and channels traversing the height of the bone portion provided parallel to the interfaces of the bone portions of the composite graft. Such perforations allow for uniform demineralization of a bone portion, and allow for ingrowth of patient bone. A demineralized discontinuous bone portion may be perforated prior to demineralization or after demineralization.

Discrete Protrusion. By the term "discrete protrusion" is intended for the purposes of the present invention, a protrusion which is discontinuous, i.e. which has a distinct length and width, where each discrete protrusion is separate and distinct from every other discrete protrusion, and includes for example a protrusion whose length is less than three times its width, preferably less than twice its width and more preferably a protusion whose length is about equal to its width.

Interlocking. By the term "interlocking" is intended for the purposes of the present invention, any pattern provided on a bone portion which allows that bone portion to engage or interlace with another bone portion, such that the engaged bone portions act as a single bone portion when stressed. Such bone portions may be provided with engaging patterns including but not limited to the following: step patterns, sawtooth patterns, and ridged patterns, patterns that define mortise and tenon joints, and lock and key type patterns. These patterns may be either discrete, for example one bone portion may include one or more protrusions and a complementary bone portion may be provided with one or more corresponding depressions, or continuous, for example bone portions are provided with complementay continuous grooves (See FIGS. 39, 40, and 41). The discrete patterns, may include protrusions and corresponding depressions of any shape and size sufficient to provide an interlocking fit, and include round, square, rectangular, triangular, oval, irregular, and any combination of geometric and curved shaped protrusions and corresponding depressions. The depth/height of the discrete or continuous patterns is from about 0.1 mm to about 3.5 mm, preferably from about 0.2 mm to about 2.0 mm, more preferably from about 0.3 mm to 1.5 mm, and most preferably from about 0.5 mm to about 1.0 mm. One of ordinary skill in the art to which the invention pertain can readily determine, select and employ an appropriate depth/height of the depression/protrusion based on the desired graft dimensions, whether or not a pin will also be used, clinical application, etc., without undue experimentation. Adjacent bone portions provided with interlocking patterns, may be self-locking such that no other connecting means, for example one or more pins, is necessary to form a unitary structure, ie. to hold the composite bone graft together. Alternatively, interlocking bone portions may be "locked" to form a unitary structure using other connection means, for example, one or more pins partially or entirely traversing a dimension of the composite bone graft, where the dimension is for example the height, width, or length of the composite bone graft.

Load-bearing. By the term "load-bearing" is intended for the purposes of the present invention a non-demineralized bone product for implantation in a patient at a site where the bone graft will be expected to withstand some level of physical load(s).

Locking pin. By the term "locking-pin" is intended for the purposes of the present invention, one or more pins entirely or partially traversing a dimension of a composite bone graft which serve to hold the bone graft together, for example, two or more interlocking bone portions provided with complementary patterns for example, a stepped pattern, may be locked using one or more pins, for example, one bone pin partially traversing the length of the graft.

Mechanical Strength:. By the term "mechanical strength" is intended for the purposes of the present invention, the ability of a bone allograft to withstand mechanical loads at an implant site without failing.

Materials properties. By the term "materials properties" is intended for the purposes of the present invention, those properties present in normal fresh bone and include loading strength, compressive strength, tensile strength, and brittleness.

Normal bone. By the term "normal bone" is intended for the purposes of the present invention, fresh hydrated autogenous and/or fresh-frozen hydrated allograft bone tissue.

Osteoconductivity. By the term "osteoconductivity" is intended for the purposes of the present invention, the ability of a substance which by its presence conducts osteoinductive activity. Suitable osteoconductive materials include but are not limited to, for example, one or more biocompatible matrix materials. Suitable osteoconductive substances include but are not limited to, for example, hydroxyapitate; collagen; any biocompatible matrix material including for example, polymeric matrix materials, bioglass, bioceramics, resorbable Biomaterials, bioabsorbable polymers, a plastic matrix, stainless steel, titanium, and cobalt-chromium-molybdenum alloy matrix; and substances including hydroxyapitate, including for example, Osteoset™ produced by Wright Medical.

Osteoinductivity. By the term "osteoinductivity" is intended for the purposes of the present invention, the ability of a substance to promote bone growth. Suitable osteoinductive substances include but are not limited to, for example, autograft bone; allograft bone; Grafton™ produced by Osteotech; DynaGraft™; demineralized cortical bone; demineralized cancellous bone; collagen including one or more growth factors including for example Novus™ produced by Stryker Biotech; collagen including demineralized bone including for example DynaGraft™; cancellous bone; cortical bone; OpteoForm™ produced by the University of Florida; OsteoFill™ produced by the University of Florida; growth factors including for example, bone morphogenic protein and transforming growth factor-β. Preferably, when a demineralized bone product is used the bone is demineralized to contain less than 6 wt % residual calcium, more preferably demineralized to contain 1 wt % to about 3 wt % residual calcium, and most preferably demineralized to contain about 2 wt % residual calcium.

Parallelepiped. By the term "parallelepiped" is intended for the purposes of the present invention, a six-faced polyhedron all of whose faces are parallelograms lying in pairs of parallel planes.

Polyhedron. By the term "polyhedron" is intended for the purposes of the present invention, a solid formed by plane faces, preferably formed by six faces.

Protrusion. By the term "protrusion" is intended for the purposes of the present invention, an irregularity in a surface of a bone allogaft having a height of from 0.1 to 5.00 mm, preferably 0.3 to 3.0 mm, more preferably 0.5 to 1.5 mm, and most preferably 0.75 mm to 1.2 mm. The protrusions can be discrete, continuous, or a combination thereof, and can be of any shape including for example: irregular; pyrimidal; conical; cuboidal; rectangular; and cylindrical; or any combination thereof. Further, a cross-section of a continuous or discrete protrusion may be of any shape including for example: irregular; rectangular; square; oval; round; triangular; trapizoidal; and a regular or irregular curve; or any combination thereof. The protrusions can be provided on the bone allograft surface in a regular, symmetric pattern including for example a linear pattern or in an irregular pattern.

Self-locking, interlocking pattern. By the term "self-locking, interlocking pattern" is intended for the purposes of the present invention, any complementary patterns provided on adjacent bone portions which enable the bone portions: to interlock, act as a unitary structure, and the bone portions are held together, without the use of any additional connecting means.

Stability. By the term "stability" is intended for the purposes of the present invention the ability of the present composite bone graft to remain at an implantation site without significantly shifting, rotating, or being extruded.

Stress. By the term "stress" is intended for the purposes of the present invention, load per unit cross-sectional area.

Textured. By the term "textured" is intended for the purposes of the present invention, a composite bone graft having one or more textured surfaces provided on the surface of the composite bone graft where the surface of the composite bone graft can be any surface or a portion of any surface including a natural surface and/or cut surface. The textured surface preferably includes a plurality of protrusions provided on the surface or a portion thereof, the protrusions of a shape including for example, irregular; pyrimidal; conical; cuboidal; rectangular; trapizoidal; curved; and cylindrical; or any combination thereof. The protrusions can be discrete, continuous, or a combination thereof.

Therapeutically Beneficial. By the term "therapeutically beneficial" is intended any material which by its action or presence, bring about a therapeutic result in a patient. Such materials include but are not limited to, for example, one or more of the following: osteoinductive substances, osteoconductive substances, and pharmaceutically active agents. Such therapeutically beneficial substances may optionally be provided with a carrier. Suitable osteoinductive substances include but are not limited to, for example, autograft bone; allograft bone; Grafton™ produced by Osteotech; DynaGraft™; demineralized cortical bone; demineralized cancellous bone; collagen including one or more growth factors including for example Novus™ produced by Stryker Biotech; collagen including demineralized bone including for example DynaGraft™; cancellous bone; cortical bone; OpteoForm™ produced by the University of Florida; OsteoFill™ produced by the University of Florida; growth factors including for example bone morphogenic protein, and transforming growth factor-β. Suitable osteoconductive substances include but are not limited to, for example, hydroxyapitate; collagen; any biocompatible matrix material including for example, polymeric matrix materials, bioglass, bioceramics, resorbable Biomaterials; bioabsorbable polymers; a plastic matrix; stainless steel; titanium; cobalt-chromium-molybdenum alloy matrix; and substances including hydroxyapitate, including for example, Osteoset™ produced by Wright Medical. Suitable pharmaceutically active agents include but are not limited to, for example, growth factors including for example bone growth factors including for example bone morphogenic protein, and transforming growth factor-β, and transforming growth factor-β; chemotherapeutic agents; anti-inflammatory agents; and antibiotics.

II. Procurement and Preliminary Processing of Bone Tissue

Suitable bone tissue includes bone obtained from any animal or human source. Preferably, bone graft tissue can be obtained from the patient himself (autologous bone) or from a cadaver (allograft bone). When allograft bone tissue is used, it is processed under strict aseptic conditions in certified clean room operating suites. The bone tissue is preferably processed to remove all soft tissue, including marrow and blood, to produce a cleaned bone graft. Suitable processing methods are well known to those skilled in the art and can be readily selected and employed by those of ordinary skill in the art without undue experimentation. Suitable methods include the methods disclosed in, for example, U.S. Pat. Nos.: 5,556,379; 5,820,581; and 5,797,891.

After processing, the cleaned grafts are packaged under sterile conditions and stored for latter processing into the present composite bone allograft, or immediately processed into the present composite bone allograft followed by appropriate packaging. The use of fresh-frozen and/or freeze-dried, bone allografts are preferred.

III. How to Make a Preferred Embodiment of the Composite Bone Graft

Figure 11A:
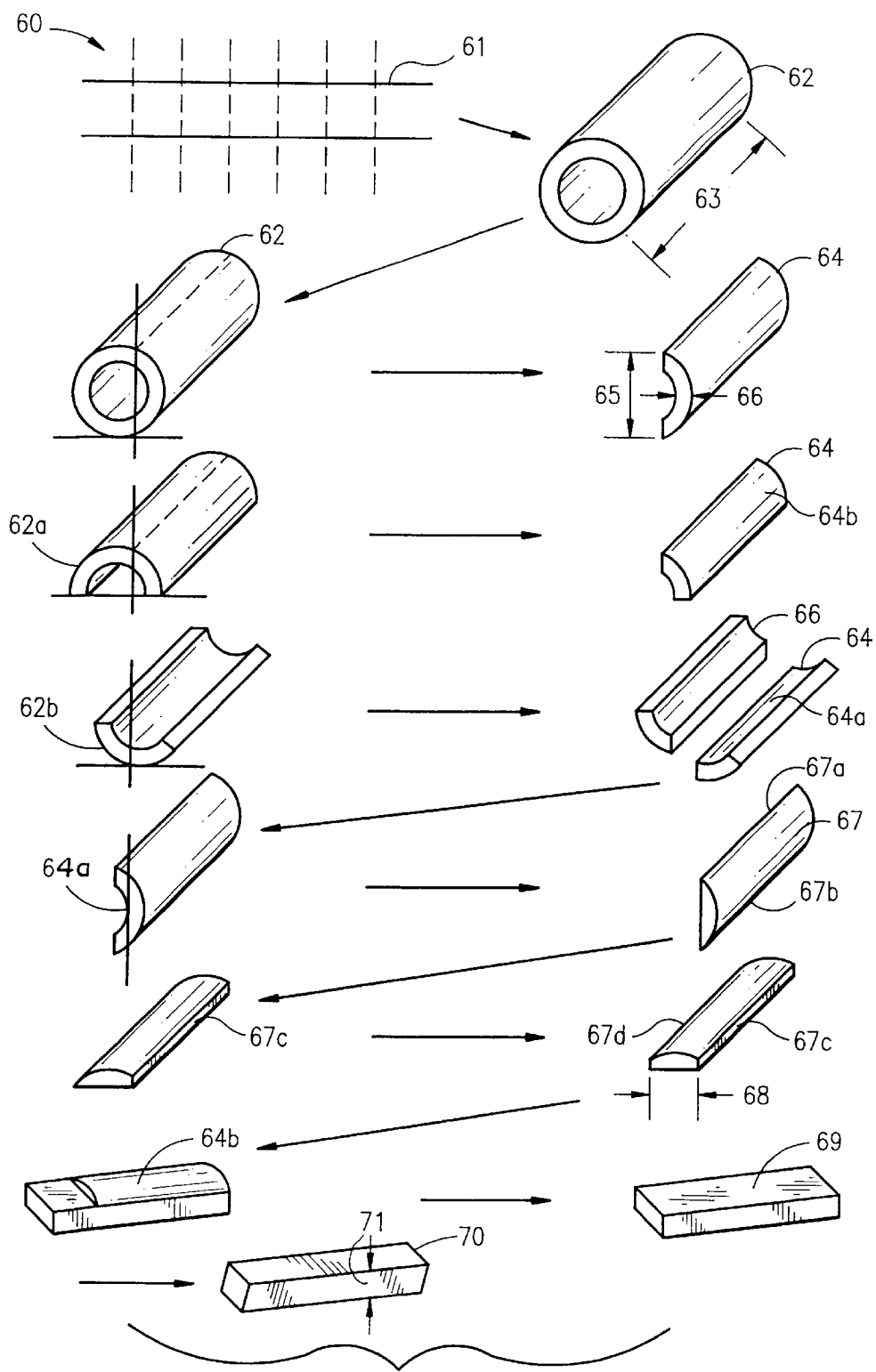
FIG. 11A.

FIG. 11A illustrates a preferred method 60 of making the present composite bone graft. A composite bone graft having of any size necessary for a particular application, can be made using the preferred method discussed hereafter. A cortical bone shaft 61 is obtained from a cadaver and is transected into cortical sections 62 having a length 63 of at least 18.0 mm, preferably at least 21.0 mm.

A cortical section 62 is then first cut to produce a cortical plank 64, the remaining cortical section 62a is turned and again cut to produce a second cortical plank, the remaining cortical plank 62b is again turned and cut into third and fourth cortical planks 64. The cortical planks 64 are cut to an appropriate width 65 and thickness 66. The concave surface 64a of the plank 64 can be smoothed if needed to produce a smoothe plank 67. Opposing edges 67a and 67b can be cut such that the cut surfaces 67c and 67d are approximately parallel. The cut width 68 should be larger than the final composite bone graft width. More specifically, cut width 68 is preferably greater than about 12.0 mm.

The convex surface 64b of plank 64 is then smoothed to produce a smoothed plank 69. The smoothed plank 64 is further smoothed by for example, milling, such that the opposing surfaces 64a and 64b, and 67c and 67d, are parallel, to produce a parallel plank 70 having a thickness 71 of at least 1.0 mm, preferably from about 1.5 mm to about 6.0 mm, and more preferably from about 2.0 mm to about 5.5 mm.

Figure 11B:
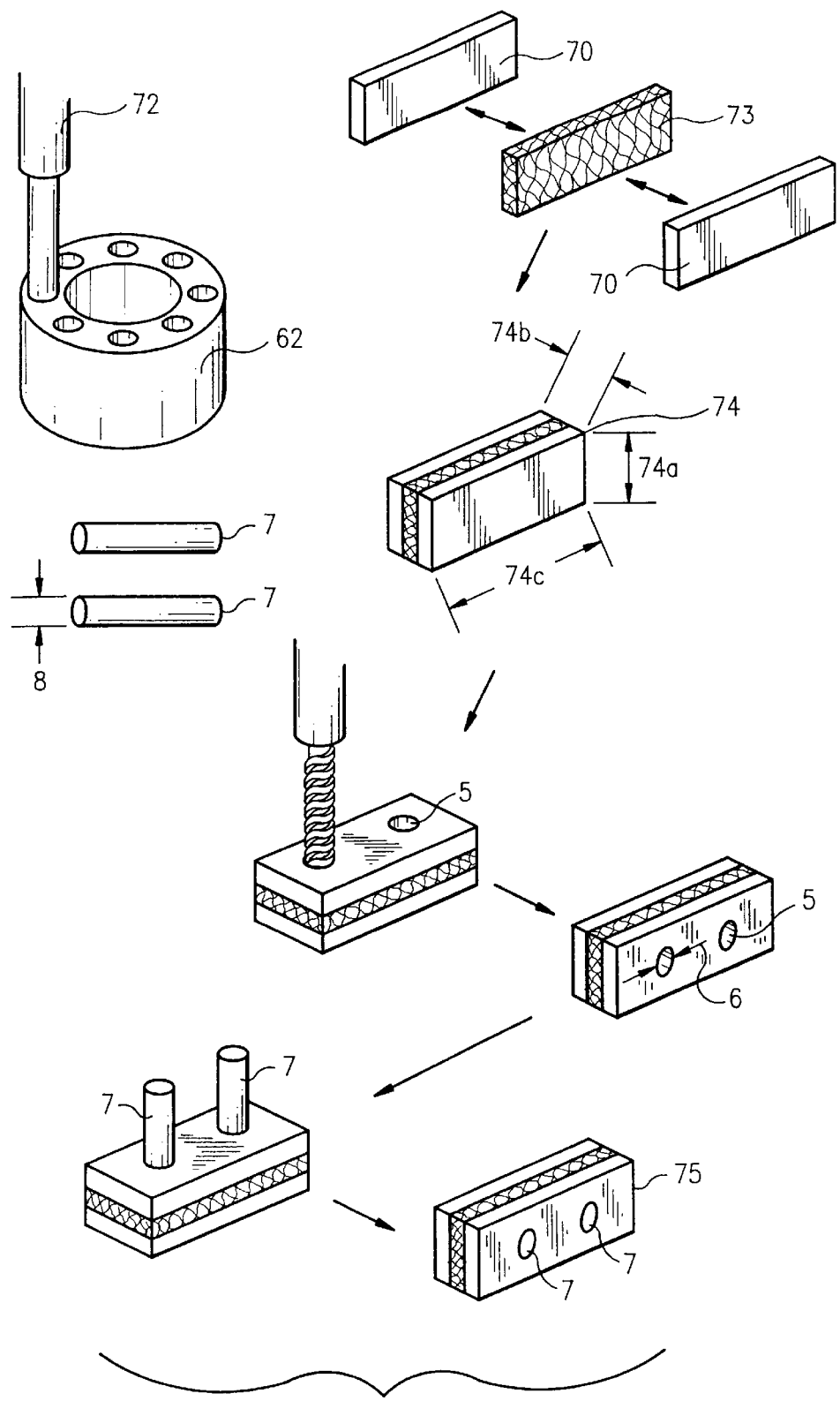
FIG. 11B.

FIG. 11B illustrates cortical pins 7 cut from a cortical section 62, using for example a drill press 72 or other means known in the art. The cortical pins 7, can also be made from a cortical plank 64, for example by turning on a lathe. The pins 7 have a diameter of from about 1.0 to about 6.0 mm, preferably from about 1.5 mm to about 4.5 mm, and more preferably from about 2.0 mm to about 4.0 mm.

If the composite bone graft includes cancellous bone, cancellous bone planks 73 are produced and sized by the method as described above for producing cortical bone planks 69 and 70. The composite bone unit 74 is then assembled as desired, for example a cortical parallel plank 70, a cancellous plank 73, and another cortical parallel plank 70. The composite bone unit 74 has a height 74a, a width 74b and a length 74c. The height 74a, width 74b and length 74c, can be readily selected by one of ordinary skill in the art, depending on factors including for example, the particular application and site of implantation in a patient. The planks are secured and holes 5 are drilled there through. The through-holes 5 are sized such that a tight or frictional fit is provided between a pin 7 and a though-hole 5. The cortical pins 7 are then inserted through the through-holes 5, and pressed to fit if needed, to produce pinned composite graft 75. The cortical bone pins 7 have a diameter 8 sufficient to provide an interference fit or frictional fit between a pin 7 and a through-hole 5. More specifically the diameter 8 of a cortical pin 7 is generally the same or slightly larger than the diameter 6 of a through-hole 5 into which it is to be inserted. The diameter of the pin 7 is preferably no more than 1.5 mm larger than the diameter of the through-hole 5.

The assembled pinned graft can thereafter be shaped as desired, for example into a trapezoid shaped graft and appropriately dimensioned to produce a composite bone graft. One or more surfaces of the composite bone graft may be textured if desired, for example, depending upon the particular application.

Figure 12:
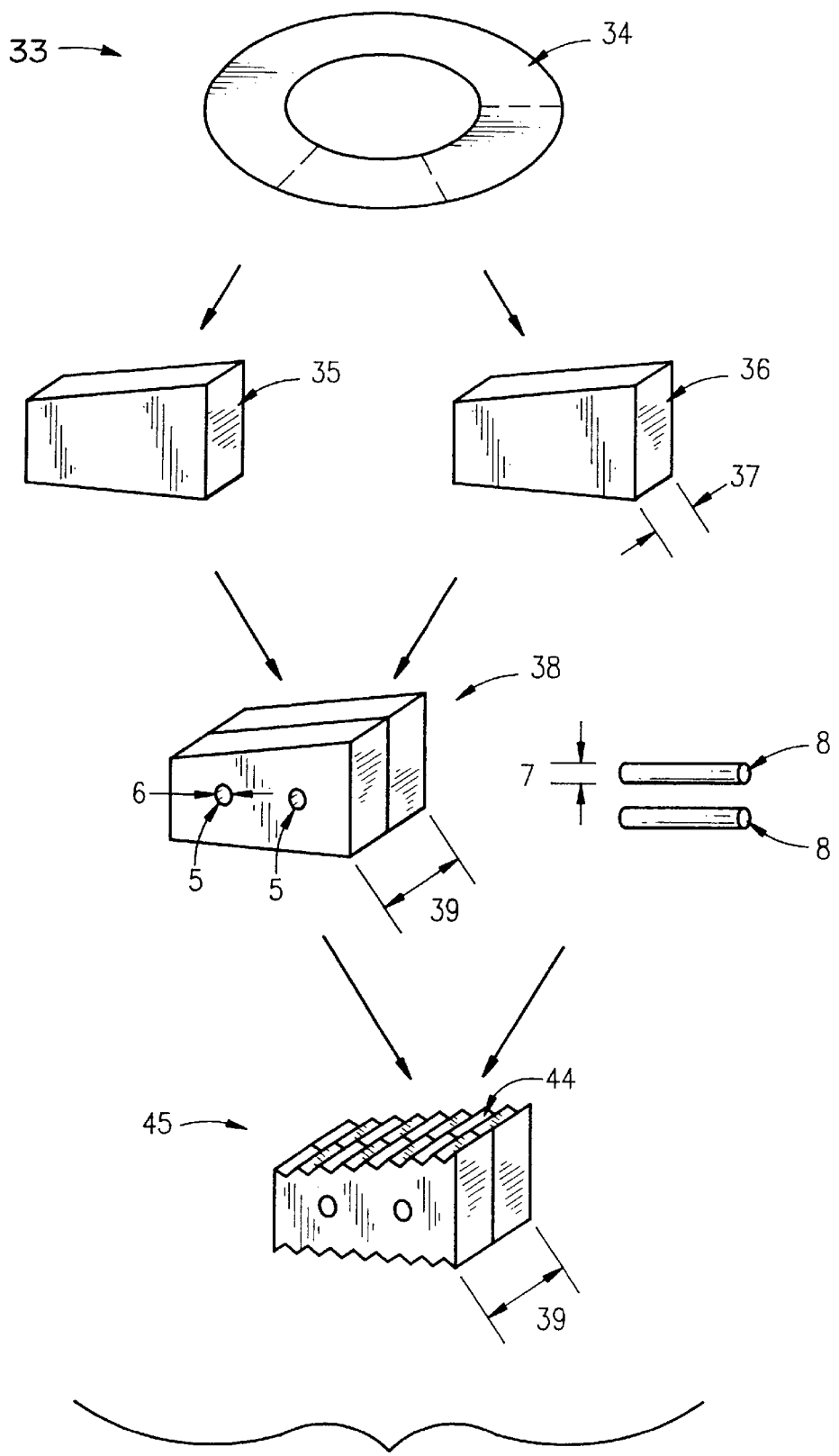
FIG. 12.

FIG. 12 illustrates an additional method 33 of making a preferred embodiment of the present composite bone graft. A cross-section of a femur is obtained from a cadaver, and cleaned using methods well known to those of ordinary skill in the art to which the present invention pertains, to remove bone marrow elements thereby producing the cleaned femural ring 34. The cleaned femural ring is then sectioned into several sections of cortical bone including a first cortical bone portion 35 and a second cortical bone portion 36, each portion having a width 37 of from about 2.0 to about 10.0 mm; preferably of from about 4.0 to about 8.0 mm; and more preferably of from about 5.0 to about 6.0 mm. Portions 35 and 36 are then held together to form a graft unit 38 having a width of 39 which is at least 4.0 mm; preferably greater than 9.0 mm; using for example, a clamp, and one or more through-holes 5 having a diameter 6 of about 0.5 mm to about 10.0 mm, preferably 2.0 mm to about 5.0 mm, more preferably 2.0 mm to about 4.0 mm, are then drilled there through.

Cortical pins 7 are produced from cortical bone by methods well known to those of ordinary skill in the art to which the present invention pertains. The pins 7 have a diameter of from 1.0 mm to about 6.0 mm, preferably from about 1.5 mm to about 4.5 mm, and more preferably from about 2.0 mm to about 4.0 mm. The graft unit 38, having through-holes 5 drilled there through is then placed in a press and one or more cortical pins 7 are inserted into the through-holes 5.

Thereafter, one or more surfaces 44 of the composite bone graft 45 can be textured by for example, milling to create a desired texture including the illustrated continuous linear protrusions (sawtooth pattern). Preferably, the composite bone graft includes opposing textured surfaces disposed perpendicular to the interface(s) of the bone portions.

Figure 15:
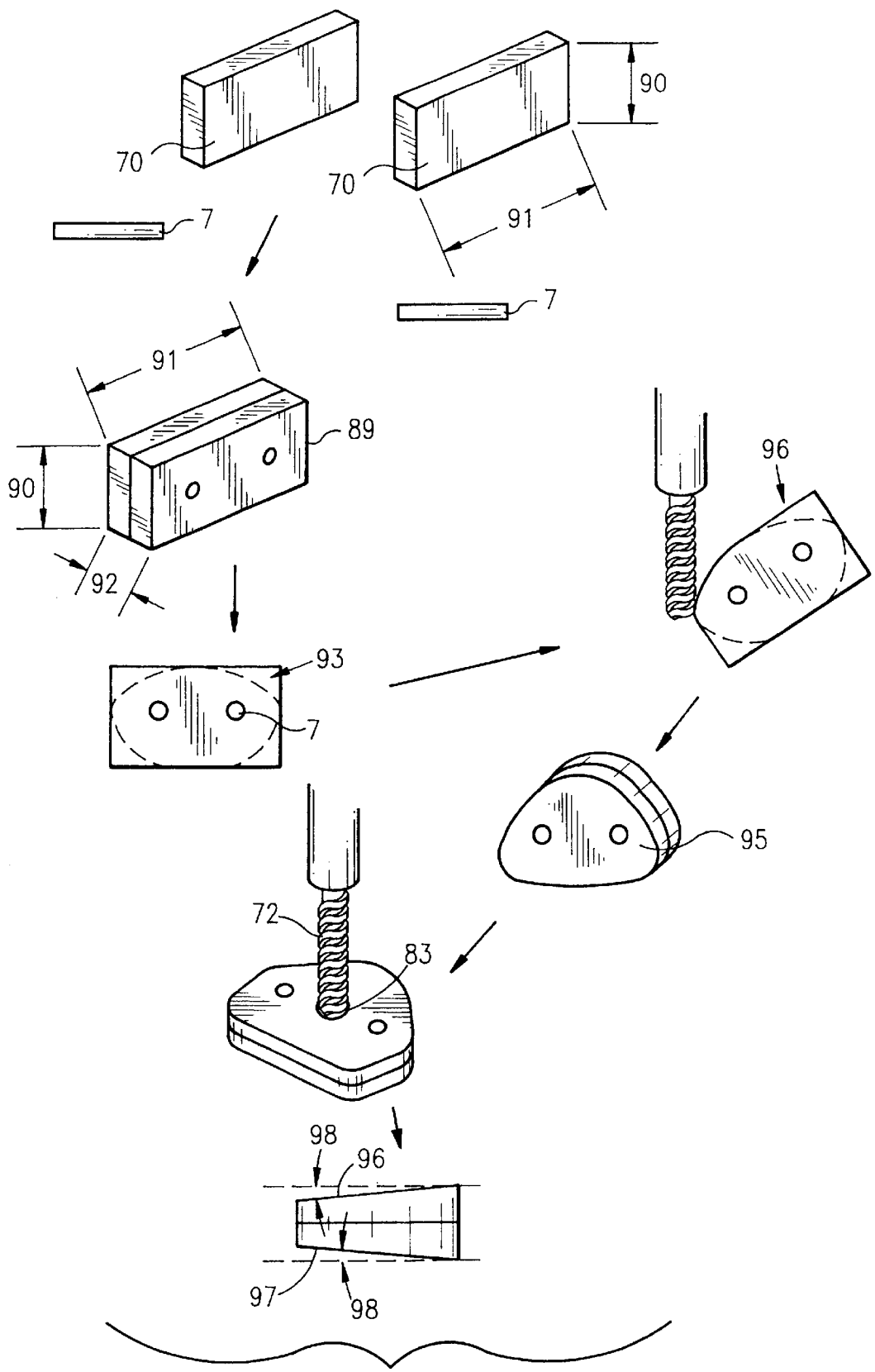
FIG. 15.

FIG. 15 illustrates a preferred method for making a cervical wedge(flattened curved wedge) composite bone graft. Cortical planks 70 are produced and pinned using cortical pins 7 as previously described in FIGS. 11A and 11B to form a pinned cortical graft unit 89. The pinned graft unit 89 has a height 90, a length 91 and a width 92. The pinned graft unit 89 is then cut and shaped 94 to a designated pattern 93 to form a flattened curved block 95. A through-hole 83 is then provided centrally through the flattened curved block 95 using for example a drill press 72. The top 96 and bottom 97 faces of the block 95 are then provided with a slope at an angle 98 for example by milling. The top 96 and/or bottom 97 faces may optionally be textured, for example by providing the faces with a plurality of pyrimidal protrusions.

Figure 29:
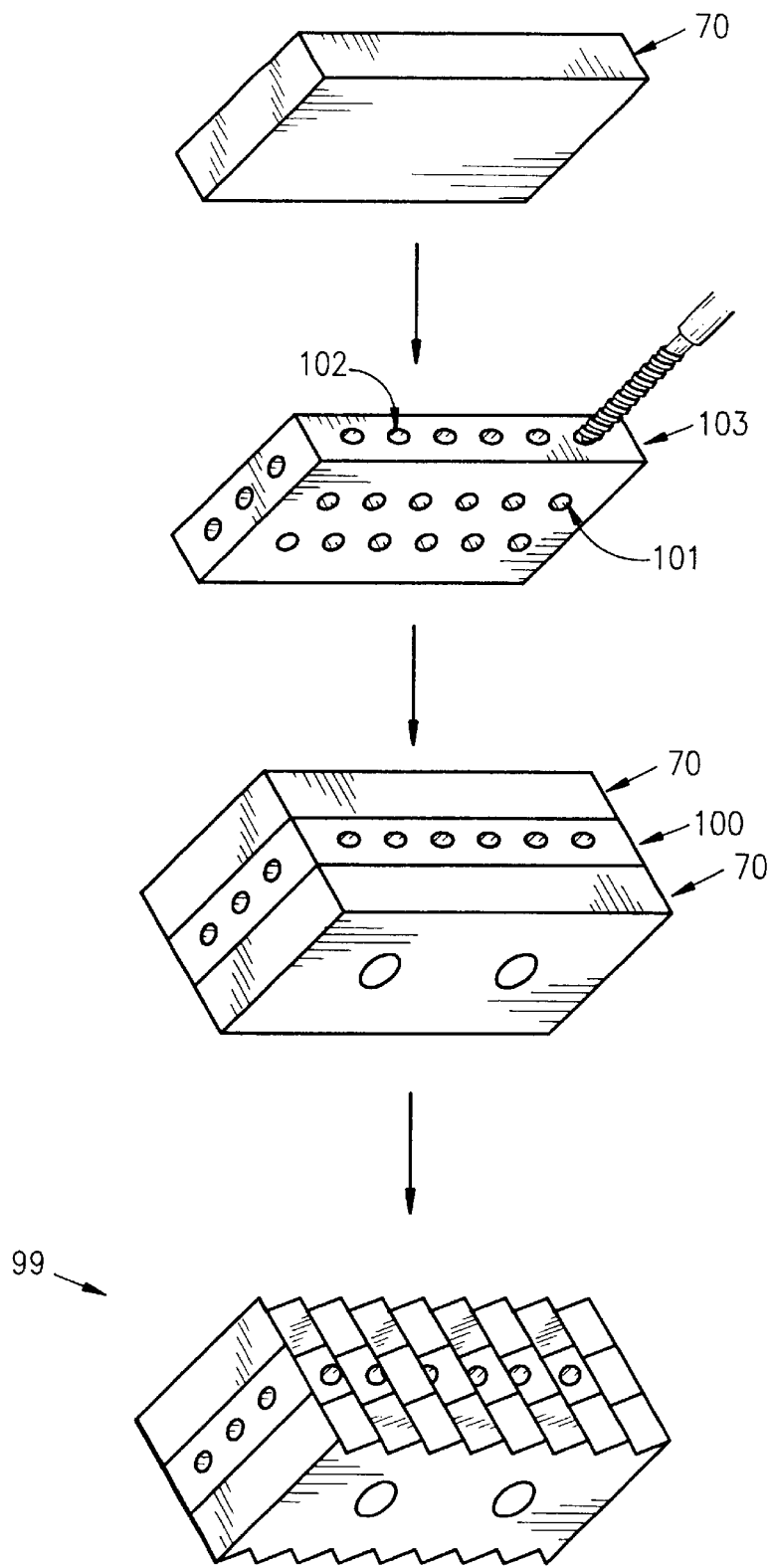
FIG. 29.

FIG. 29 illustrates a method of making a composite bone graft 99 including a discontinuous, demineralized, cortical bone portion 100 disposed between two cortical bone portions 70. The cortical parallel planks 70 are produced as discussed above in reference to FIG. 11. The discontinuous, demineralized, cortical bone portion 100 is produced by first producing a cortical parallel plank 70, as described above in reference to FIG. 11. The cortical parallel plank 70 is then perforated, for example using a drill press, to create perforations 101 traversing the width of the plank, and to create channels 102 traversing the height of the plank, to produce a discontinuous bone plank 103. The discontinuous bone plank 103 is then demineralized by any method well known to those of ordinary skill in the art, including for example, demineralizing in 0.5–0.6N hydrochloric acid at from 25° C. to 50° C., preferably at from 25° C. to 37° C., for a period of time of from about 1 hour to about 8 hours, preferably for about 2 hours, more preferably demineralization is carried out until the discontinuous bone plank 103 contains less than 6 wt % residual calcium, preferably about 1 wt % to about 3 wt % residual calcium, and most preferably demineralized to contain about 2 wt % residual calcium, to produce a demineralized discontinuous plank 100. The demineralized discontinuous bone plank 100 and the cortical parallel planks 70 are then assembled, shaped, and textured to produce the composite bone graft 99, according to the methods described in reference to FIG. 11.

Figure 30:
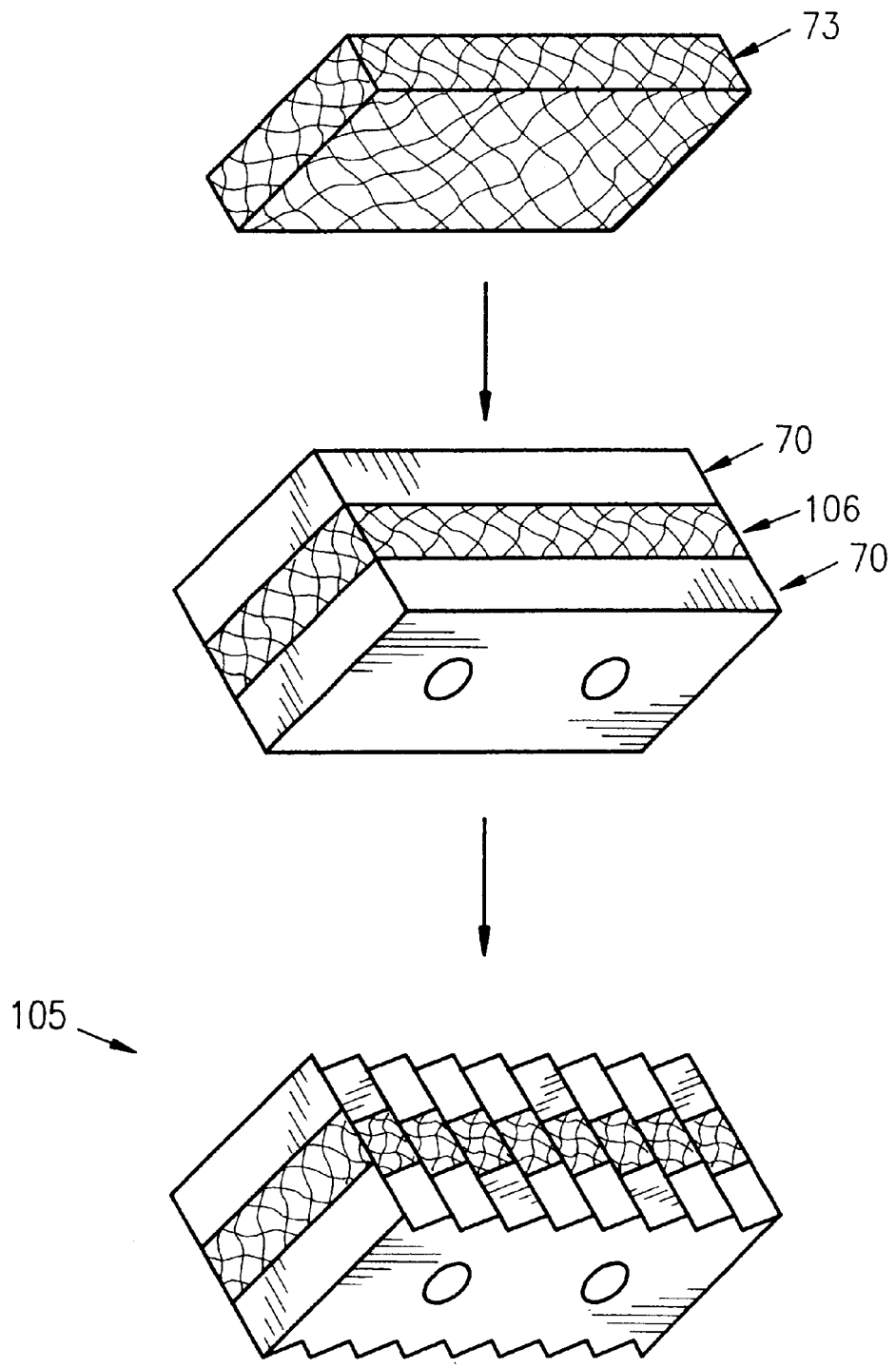
FIG. 30.

FIG. 30 illustrates a method of making a composite bone graft 105 including a demineralized cancellous bone portion 106 disposed between two cortical bone portions 70. The cortical parallel planks 70 are produced as discussed above in reference to FIG. 11. The demineralized cancellous bone portion 106 is produced by first producing a cancellous parallel plank 73, as described above in reference to FIG. 11. The cancellous parallel plank 73 is then demineralized by any method well known to those of ordinary skill in the art, including for example, demineralizing in 0.5–0.6N hydrochloric acid at from 25° C. to 50° C., preferably at from 25°

C. to 37° C., for a period of time of from about 20 minutes to about 6.0 hours, preferably for about 30 minutes to about 2.0 hour to produce a demineralized cancellous bone plank 106. More preferably, demineralization is carried out until the bone plank 106 produced, contains less than 6 wt % residual calcium, preferably about 1 wt % to about 3 wt % residual calcium, and most preferably demineralized to contain about 2 wt % residual calcium. The demineralized cancellous bone plank 106 and the cortical parallel planks 70 are then assembled, shaped, and textured to produce the composite bone graft 105, according to the methods described in reference to FIG. 11.

Composite bone grafts including two or more distinct cortical bone portions each bone portion provided with a pattern thereon to enable the bone portions to interlock or engage, are made by first making cortical bone planks as described. After the planks are made they are each provided with a pattern, for example a discrete or continuous pattern. The patterned planks are then fitted together. The patterned planks may be self-locking, ie. provided with a "key" type pattern, to form a unitary structure, or may be locked using one or more pins entirely or partially traversing a dimension, ie. the graft's height, width, and/or length. Thereafter, the locked graft is shaped to form the composite bone graft. Suitable patterns include any complementary patterns which when provided on two or more adjacent bone portions, enable two or more bone portions to act as one, where the patterns are self-locking or are locked with one or more additional connection means, including for example one or more pins.

IV. Description of Preferred Embodiments of the Composite Bone Graft

The present composite bone graft provides a bone graft which can be appropriately sized for any application, has increased stability of the graft at an implant site and promotes the ingrowth of patient bone, while providing excellent mechanical strength.

FIG. 1 illustrates a perspective view of a preferred composite bone graft 1 including a first cortical bone portion 2, a second cortical bone portion 4, a cancellous bone portion 3 sandwiched between bone portions 2 and 4, a through-hole 5 having a diameter 6, and a cortical bone pin 7 having a diameter 8. The composite bone graft 1, has a length 9, a posterior height 13, an anterior height 11, a composite width 12, and section widths 10a, 10b, and 10c.

FIG. 2 illustrates a side view of a composite bone graft 1 having opposing textured surfaces 14a and 14b provided perpendicular to the interfaces of the bone portions. 14a and 14b illustrate continuous linear protrusions defining a saw-tooth-like pattern.

Figure 3:
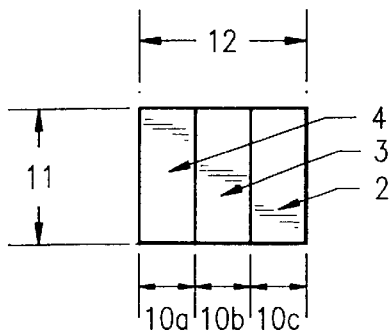
FIG. 3.

FIG. 3 illustrates a cross-section posterior view of composite bone graft 1, illustrating section widths 10a, 10b, and 10c of bone portions 2, 3, and 4, respectively, and having an anterior height 11 and composite width 12.

Figure 4:
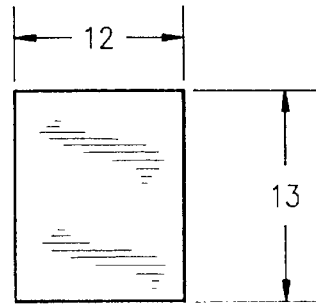
FIG. 4.

FIG. 4 illustrates a cross-section anterior view of composite bone graft 1, illustrating an posterior height 13 and composite width 12.

FIG. 5 illustrates a top view of composite bone graft 1 illustrating cortical bone portions 2 and 4, cancellous bone portion 3 disposed there between, and textured surface 14b.

FIG. 6 is a perspective view of composite bone graft 1 illustrating cortical bone portions 2 and 4, cancellous bone portion 3 disposed there between, textured surfaces 14a and 14b, and cortical bone pins 7.

FIG. 7 illustrates a perspective of a preferred composite bone graft 15 having a first cortical bone portion 16, a second cortical bone portion 17, cortical bone pins 18, through-holes 19, and void 107, where the diameter of the through-holes 19 and the diameter of the cortical bone pins 18 are configured to allow a slidable connection between the bone portions 16 and 17, and the bone portions 16 and 17 and the cortical bone pins 18. The composite bone graft 15 includes a top textured surface 14b and a bottom textured surface 14a disposed perpendicular to an interface between bone portions 16 and 17. Composite bone graft 15 may optionally include one or more cancellous or cortical bone portions disposed between and slidably connected to cortical bone portions 16 and 17, and to cortical bone pins 18.

FIG. 8 illustrates a top view of composite bone graft 15 having a first cortical bone portion 16, a second cortical bone portion 17, and a cancellous bone portion 20 disposed there between, with one portions 16, 17, and 20 being slidably connected with cortical bone pins 19. This graft can be used in place of the traditional iliac crest vedge.

FIG. 9 illustrates a perspective view of a preferred composite bone graft 21 including a first cortical bone portion 22, a second cortical bone portion 23, a third cortical bone portion 24, through-holes 5 and cortical bone pins 7.

FIG. 10 illustrates a preferred composite bone graft 25 including a plurality of cortical bone portions including a first cortical bone portion 26, a second cortical bone portion 27, a third cortical bone portion 28, a forth cortical bone portion 29, a fifth cortical bone portion 30, and a single cortical bone pin 31 inserted in through-hole 32. This graft can be used in place of the traditional cloward dowel.

Figure 13A:
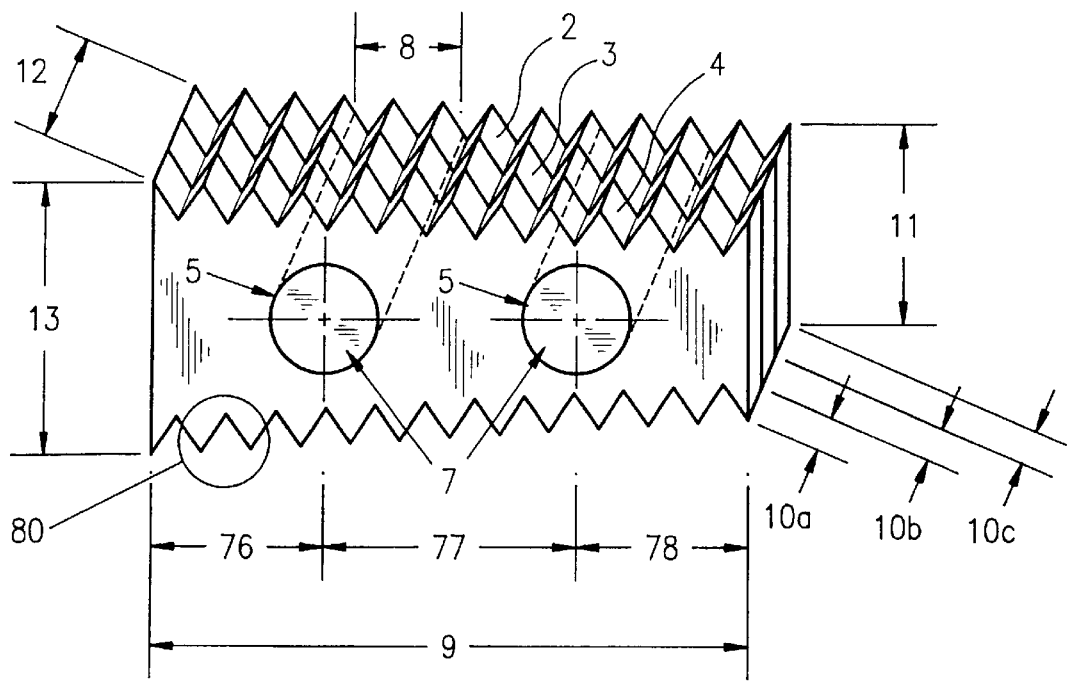
FIGS. 13A & 13B.
Figure 13B:
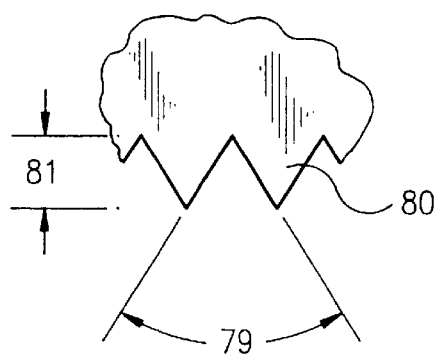

FIG. 13A is a perspective view of a preferred trapezoid block composite bone graft having opposing textured surfaces which include a plurality of protrusions 80, and having a first cortical bone portion 2, a second cortical bone portion 4, a cancellous bone portion 3 sandwiched between bone portions 2 and 4, through-holes 5, and a cortical bone pins 7 having a diameter 8. The composite bone graft, has a length 9, a posterior height 13, an anterior height 11, a composite width 12, section widths 10a, 10b, and 10c, a length 76 which is the length of the graft measured from the anterior end to the center of the first pin 7, a length 77 which is the length of the graft measured from the center point of a first pin 7 to a center point of a second pin 7, and a length 78 which is the length of the graft measured from a center point of a second pin to the posterior end of the graft. The textured surface is detailed in FIG. 13B. The protrusions 80 have a height of 81, and are cut in a "saw-tooth" pattern at an angle of 79.

Figure 14A:
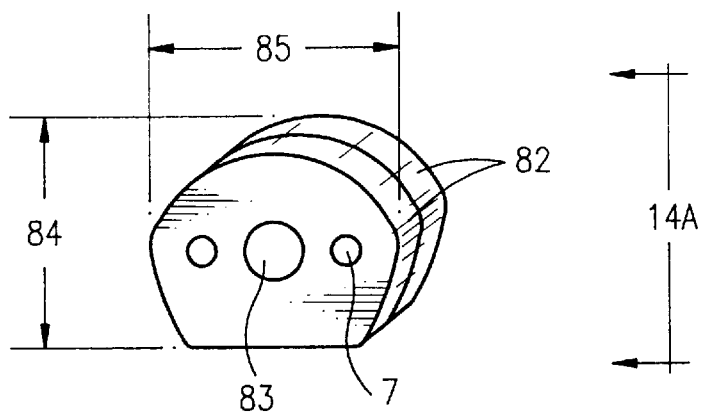
FIGS. 14A, 14B & 14C.
Figure 14B:
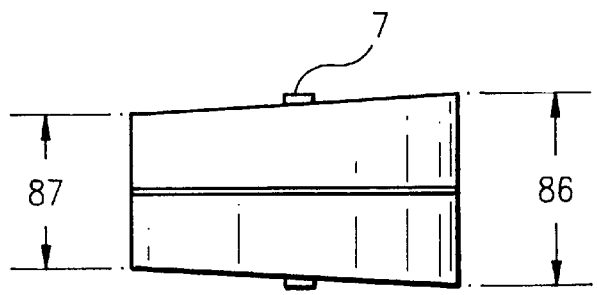
Figure 14C:
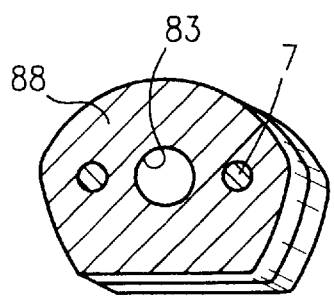

FIGS. 14A, 14B and 14C, illustrate a cervical wedge composite bone graft (flattened curved wedge composite bone graft) for use in cervical fusions where 14A is a perspective standing view, 14B is a side view, and 14C is a perspective view where the graft is provided with opposing textured surfaces. The flattened curved wedge composite bone graft includes first and second cortical bone portions 82 held together by two cortical bone pins 7 to form a pinned graft unit, and the pinned graft unit having a hole 83 disposed there through located between pins 7. The cervical fusion graft has a diameter 84, a width 85, an front composite width 87, and a back composite width 86. The cervical fusion graft as shown in FIG. 14C has textured opposing faces which include a plurality of pyrimidal protrusions 88.

FIG. 16 illustrates a perspective view of a mechanical connector 46 having a slot 47 extending from its lower end.

FIG. 17 illustrates a side view of mechanical connector 46 having a slot 47 extending from its lower end.

FIG. 18 illustrates a cross-section view of mechanical connector 46 having a slot 47 extending from its lower end.

FIG. 19 illustrates a perspective view of a mechanical connector 48 having a plurality of horizontally disposed grooves 49.

FIG. 20 illustrates a perspective view of a mechanical connector 50 having helical threads 51.

FIG. 21 illustrates a perspective view of a mechanical connector 52 having a plurality of vertically disposed grooves 53.

FIG. 22 illustrates a perspective view of a mechanical slotted pin connector 54.

FIG. 23 illustrates a perspective view of a mechanical connector 55 having a plurality of horizontally disposed ridges 56.

FIG. 24 illustrates a perspective view of a mechanical triangular pin connector 57.

FIG. 25 illustrates a perspective view of a mechanical square pin connector 58.

FIG. 26 illustrates a perspective view of a mechanical hexagon pin connector 59.

Figure 27:
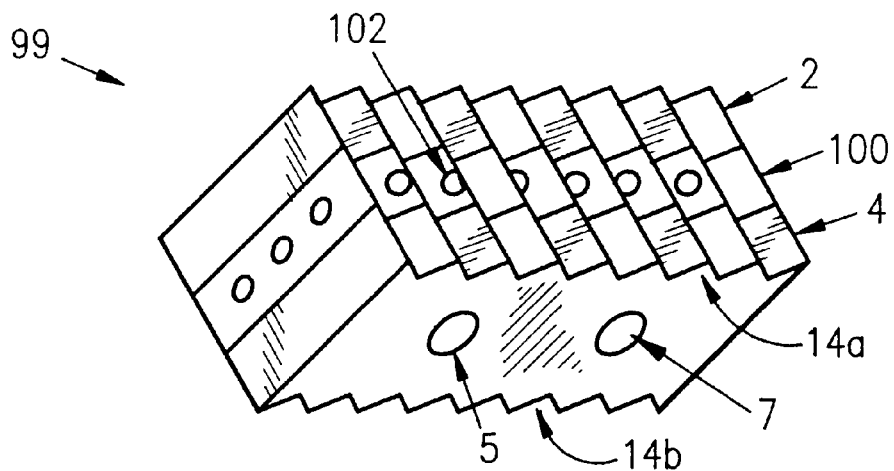
FIG. 27.

FIG. 27 illustrates a perspective view of a rectangular block composite bone graft 99, including a first cortical bone portion 2, a second cortical bone portion 4, a discontinuous, demineralized cortical bone portion 104 disposed between cortical bone portions 2 and 4, where the discontinuous, demineralized cortical bone portion 100 includes perforations traversing the width of the bone portion 100 and are disposed perpendicular to the interfaces of the bone portions 2, 100 and 4, and channels 102 traversing the height of bone portion 100 and are disposed parallel to the interfaces of the bone portions 2, 100, and 4, through-holes 5, and cortical bone pins 7. The composite bone graft 99 includes opposing textured surfaces 14a and 14b provided perpendicular to the interfaces of the bone portions and defining a saw-tooth-like pattern.

Figure 28:
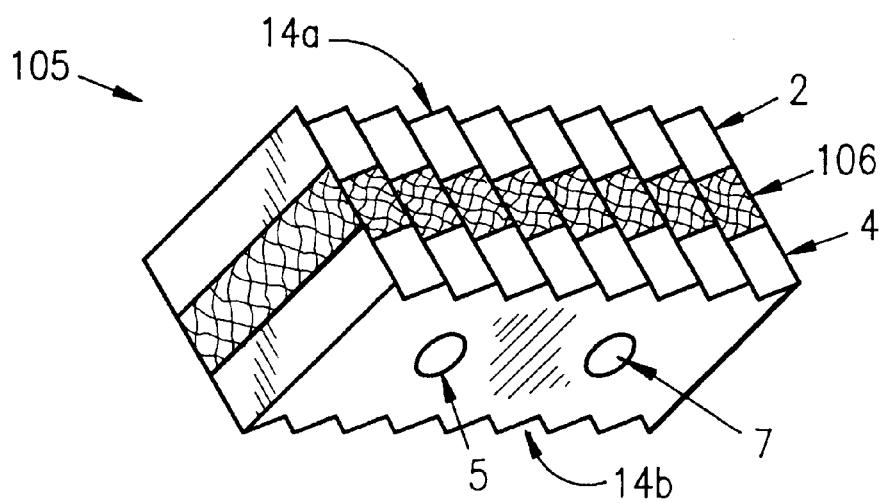
FIG. 28.

FIG. 28 illustrates a perspective view of a rectangular block composite bone graft 105, including a first cortical bone portion 2, a second cortical bone portion 4, a demineralized cancellous bone portion 106 disposed between cortial bone portions 2 and 4, through-holes 5, and cortical bone pins 7. The composite bone graft 105 includes opposing textured surfaces 14a and 14b provided perpendicular to the interfaces of the bone portions and defining a saw-tooth-like pattern.

Figure 31A:
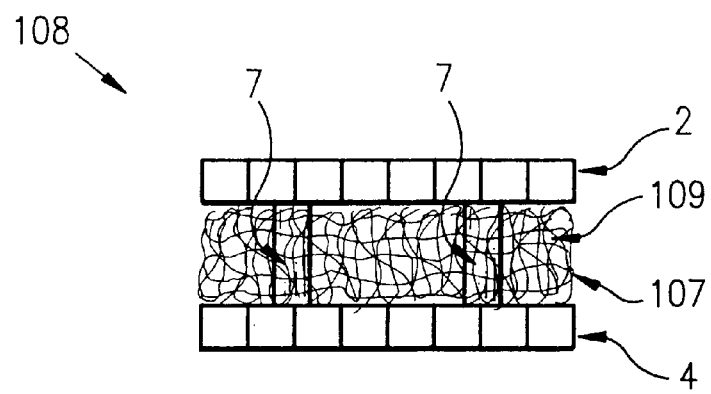
FIG. 31A.

FIG. 31A illustrates a top view of a rectangular block composite bone graft 108, including a first cortical bone portion 2, a second cortical bone portion 4, a void 107 disposed between cortical bone portions 2 and 4, and cortical bone pins 7. The void 107 includes one or more therapeutically beneficial substances 109.

Figure 31B:
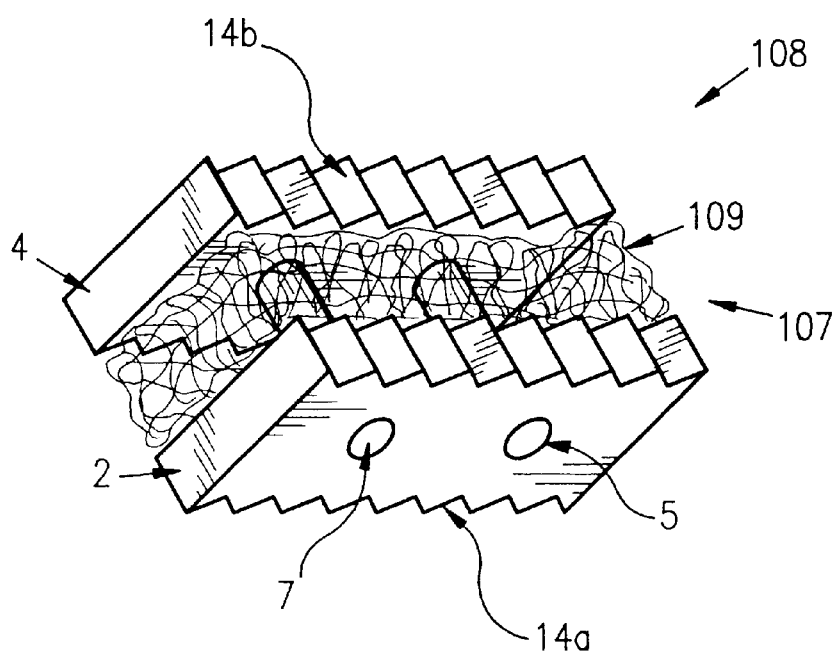
FIG. 31B illustrates a perspective view of a composite bone graft including a void disposed between two cortical bone portions where the void includes one or more therapeutically beneficial substances, and the composite graft includes opposing textured surfaces.

FIG. 31B illustrates a perspective view of a rectangular block composite bone graft 108, including a first cortical bone portion 2, a second cortical bone portion 4, a void 107 disposed between cortical bone portions 2 and 4, through-holes 5, and cortical bone pins 7. The void 107 includes one or more therapeutically beneficial substances 109. The composite bone graft 108 includes opposing textured surfaces 14a and 14b provided perpendicular to the interfaces of the bone portions 2 and 4, with the therapeutically beneficial substance 109, and defining a saw-tooth-like pattern.

Figure 32A:
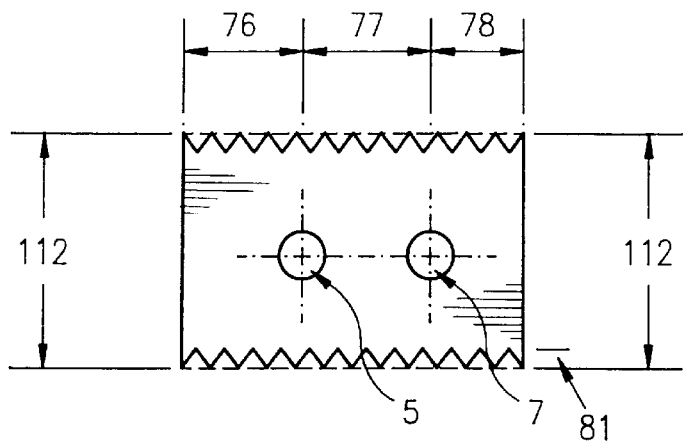
FIG. 32A, 32B, & 32C.
Figure 32B:
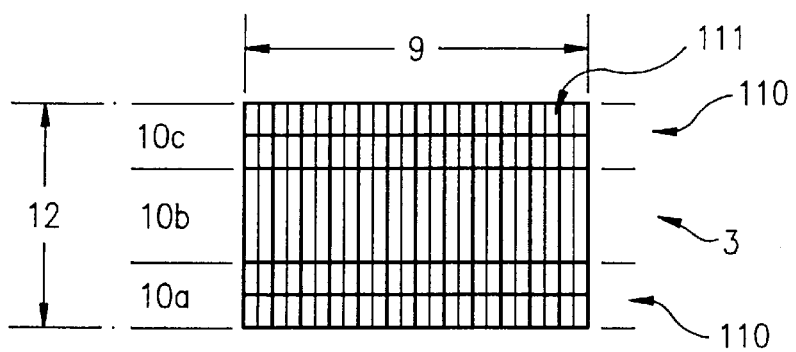
Figure 32C:
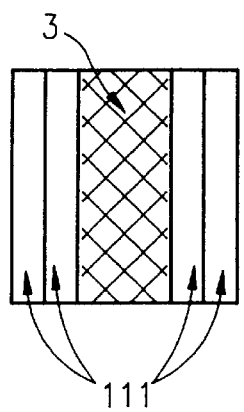

FIGS. 32A, 32B and 32C, illustrate a parallel block composite bone graft where 32A is a cross-section view, 32B is a top-view, and 32C is a is a side view of the width of the composite graft, where the graft is provided with opposing textured surfaces. The composite bone graft includes first and second cortical bone units 110, a cancellous bone portion 3 sandwiched between bone units 110, through-holes 5, and a cortical bone pins 7 (The diameter of each bone pin may be the same or different depending on the particular application, implant and size of the graft, the diameter of a pin is preferably about 1.0 to about 5.0 mm, more preferably from about 1.5 mm to about 4.0 mm, even more preferably from about 2.0 to about 3.5 mm, and most preferably 2.5 to 3.0 mm). The composite bone graft, has a length 9 (preferably from 5.0 to about 50.0 mm, more preferably from about 10.0 to about 30.0 mm, even more preferably from about 15.0 mm to about 25.0 mm, and most preferably about 21.0 mm), a height 112 (preferably from about 3.0 mm to about 30.0 mm, more preferably from about 5.0 mm to about 25.0 mm, even more preferably from about 8.0 mm to about 15.0 mm), a composite width 12 (preferably from about 4.0 mm to about 20.0 mm, more preferably from about 5.0 mm to about 15.0 mm), section widths 10a, 10b, and 10c, which are preferably 4.0 mm, 3.0 mm, and 4.0 mm; 4.0 mm, 5.0 mm, and 4.0 mm; and 3.0 nmm, 5.0 mm, and 3.0 mm; respectively, where two bone portions 111 are layered to form the bone unit 110, and where the width of each bone portion 111 is such that when layered with another bone portion 111, the resultant width 113 is as desired, for example, 4.0 mm. The bone graft has a length 76 (for example when the length of the graft is 21.0 mm, length 76 is preferably about 7.5 mm) which is the length of the graft measured from the anterior end to the center of the first pin 7, a length 77 (for example when the length of the graft is 21.0 mm, length 77 is preferably about 8.0 mm) which is the length of the graft measured from the center point of a first pin 7 to a center point of a second pin 7, and a length 78 (for example when the length of the graft is 21.0 mm, length 78 is preferably about 5.5 mm) which is the length of the graft measured from a center point of a second pin to the posterior end of the graft. The protrusions 80 have a height of 81 (preferably from about 0.5 mm to about 2.5 mm, more preferably from about 1.0 mm to about 2.0 mm, and most preferably from about 1.1 mm to about 1.6 mm), and are cut in a "saw-tooth" pattern at an angle (preferably about 60°).

Figure 33A:
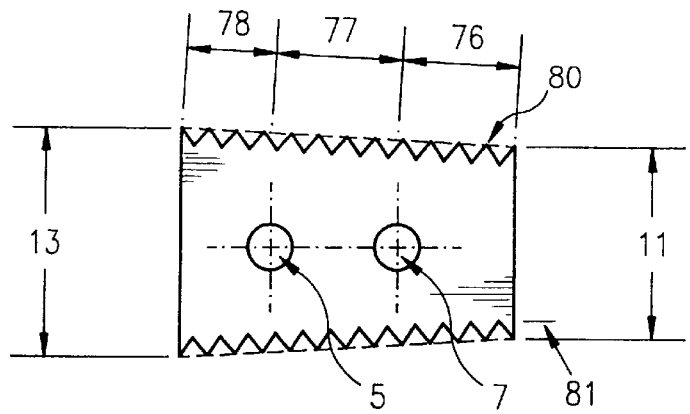
FIG. 33A, 33B, & 33C.
Figure 33B:
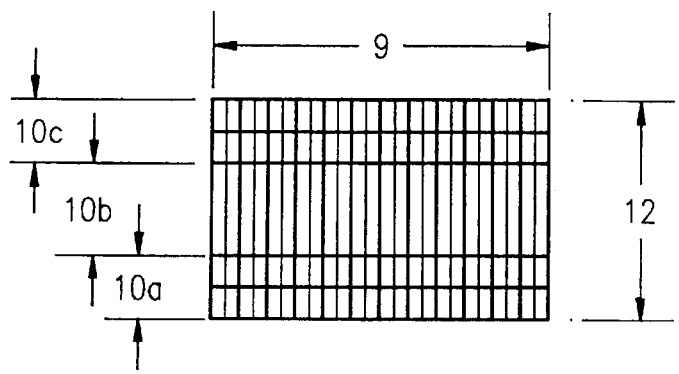
Figure 33C:
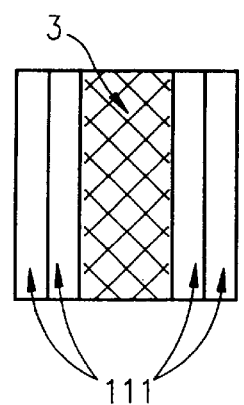

FIGS. 33A, 33B, and 33C, illustrate a trapezoid wedge composite where 33A is a cross-section view, 33B is a top-view, and 33C is a side view of the width of the composite graft. The composite bone graft includes first and second cortical bone units 110, a cancellous bone portion 3 sandwiched between bone units 110, through-holes 5, and a cortical bone pins 7 (The diameter of each bone pin may be the same or different depending on the particular application, implant and size of the graft, the diameter of a pin is preferably about 1.0 to about 5.0 mm, more preferably from about 1.5 to about 4.0 mm, even more preferably from about 2.0 to about 3.5 mm, and most preferably 2.5 to 3.0 mm). The composite bone graft, has a length 9 (preferably from 5.0 to about 50.0 mm, more preferably from about 10.0 to about 30.0 mm, even more preferably from about 15.0 mm to about 25.0 mm, and most preferably about 21.0 mm), an anterior height 11 (preferably from about 3.0 mm to about 30.0 mm, more preferably from about 5.0 mm to about 25.0 mm, even more preferably from about 8.0 mm to about 15.0 mm), a posterior height 13 (preferably from about 5.0 mm to about 50.0 mm, more preferably from about 7.0 mm to about 25.0 mm, and even more preferably from about 10.0 to about 15.0 mm), a composite width 12 (preferably from about 4.0 mm to about 20.0 mm, more preferably from bout 5.0 mm to about 15.0 mm, section widths 10a, 10b, and 10c, which are preferably 4.0 mm, 3.0 mm, and 4.0 mm; 4.0 mm, 5.0 mm, and 4.0 mm; and 3.0 mm, 5.0 mm, and 3.0 mm; respectively, where two bone portions 111 are layered to form the bone unit 110, and where the width of each bone portion 111 is such that when layered with another bone portion 111, the resultant width 10a or 10c is as desired, for example, 4.0 mm. The bone graft has a length 76 (for example when the length of the graft is 21.0 mm, length 76 is preferably about 7.5 mm) which is the length of the graft measured from the anterior end to the center of the first pin 7, a length 77 (for example when the length of the graft is 21.0 mm, length 77 is preferably about 8.0 mm) which is the length of the graft measured from the center point of a first pin 7 to a center point of a second pin 7, and a length 78 (for example when the length of the graft is 21.0 mm, length 78 is preferably about 5.5 mm) which is the length of the graft measured from a center point of a second pin to the posterior end of the graft. The protrusions 80 have a height of 81 (preferably from about 0.5 mm to about 2.5 mm, more preferably from about 1.0 mm to about 2.0 mm, and most preferably from about 1.1 mm to about 1.6 mm), a d are cut in a "saw-tooth" pattern at an angle (preferably about 60°).

Figure 34:
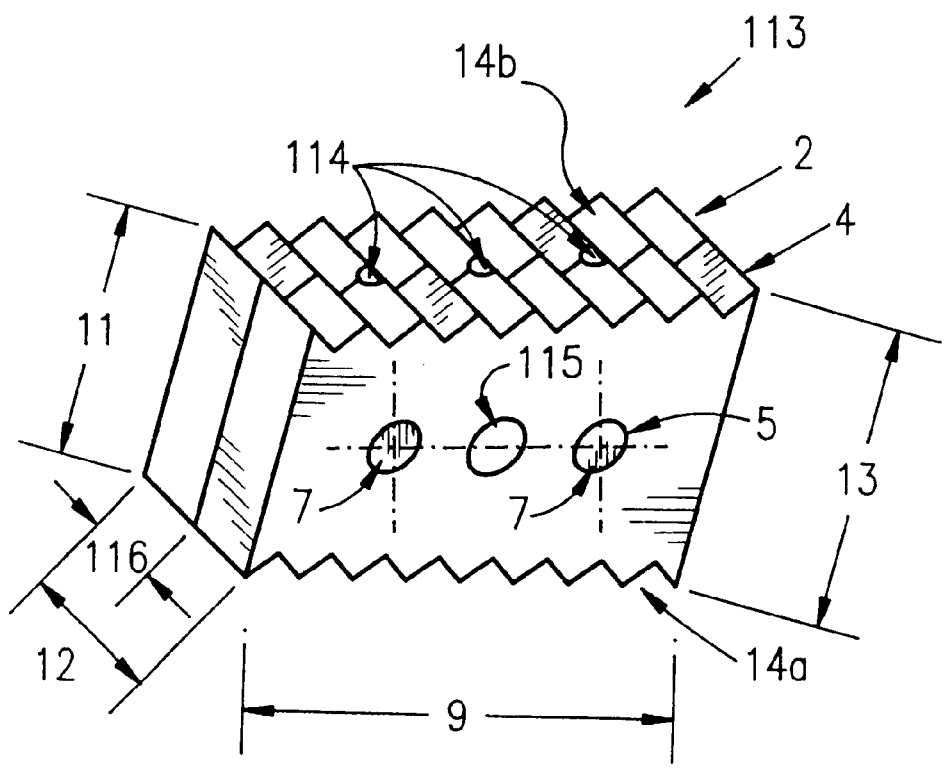
FIG. 34.

FIG. 34 illustrates a trapezoid wedge composite bone graft 113 including a first cortical bone portion 2, a second cortical bone portion 4, opposing textured surfaces 14a and 14b, vertically disposed channels 114 (preferably channels 114 have a diameter of from 0.25 mm to about 5.0 mm, more preferably from about) 0.5 mm to about 4.0 mm, and most preferably from about 1.0 mm to about 3.0 mm), and horizontally dispose channel 115 (preferably channels 115 have a diameter of from about 0.5 to about 6.0 mm, more preferably from about 1.0 mm to about 5.0 mm, and most preferably from about 2.0 mm to about 4.0 mm). The composite bone graft also includes cortical bone pins 7 (preferably bone pins 7 have a diameter of from about 2.0 mm to about 3.5 mm, more preferably from about 2.5 mm to about 3.0 mm, where each pin may have the same or a different diameter) and through-holes 5. The channels may optionally include one or more therapeutically beneficial substances. The graft has a length 9 (preferably from 5.0 to about 50.0 mm, more preferably from about 10.0 to about 30.0 mm, even more preferably from about 15.0 mm to about 25.0 mm, and most preferably about 21.0 rm), an front height 11 (preferably from about 3.0 mm to about 30.0 mm, more preferably from about 5.0 mm to about 25.0 mm, even more preferably from about 8.0 mm to about 15.0 mm), a back height 13 (preferably from about 5.0 mm to about 50.0 mm, more preferably from about 7.0 mm to about 25.0 mm, and even more preferably from about 10.0 mm to about 15.0 mm), a composite width 12 (preferably from about 4.0 mm to about 20.0 mm, more preferably from about 5.0 mm to about 15.0 mm and most preferably about 6.0 mm to about 8.0 mm), and a section width 116 (preferably from about 1.0 mm to about 5.0 mm, more preferably from about 2.0 mm to about 4.0 mm, and most preferably from about 3.0 mm to about 3.5 mm).

Figure 35A:
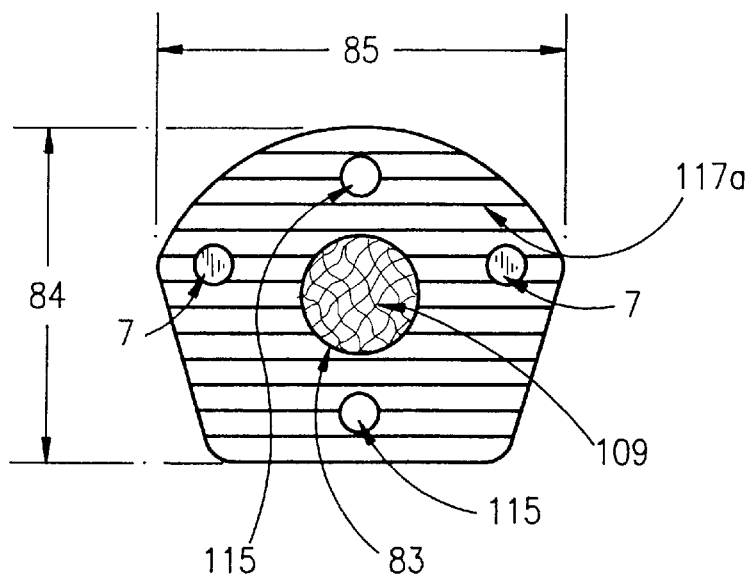
FIGS. 35A & 35B.
Figure 35B:
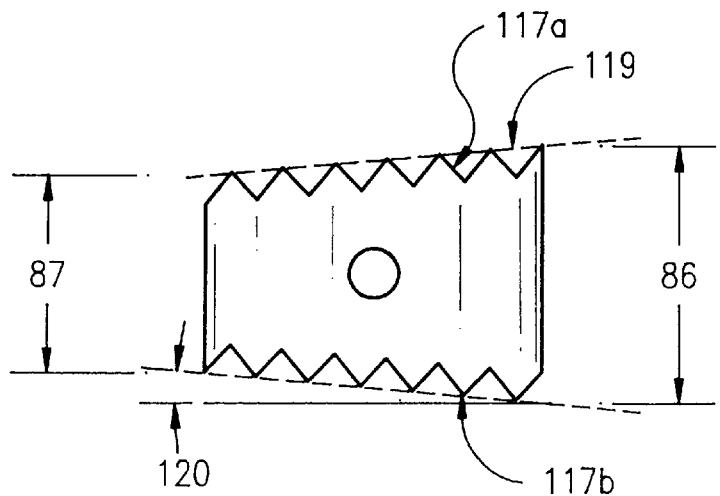

FIG. 35A illustrates a standing view of a cervical wedge composite bone graft having a textured surface 117a. The cervical wedge composite bone graft includes first and second cortical bone portions 82 held together by two conical bone pins 7 to form a pinned graft unit, and the pinned graft unit having a through-hole 83 (preferably from about 2.0 mm to about 8.0 mm in diameter, more preferably from about 3.0 mm to about 5.0 mm) disposed there through located between pins 7. The cervical fusion graft has a diameter 84, a width 85, a front composite width 87, and a back composite width 86. The cervical wedge also includes horizontally disposed channels 115 (preferably channels 115 have a diameter of from about 0.5 to about 10.0 mm, more preferably from about 1.0 mm to about 5.0 mm, and most preferably from about 2.0 mm to about 4.0 mm), and one or more therapeutically beneficial substances 109, for example cancellous bone or demineralized cancellous bone, disposed in through-hole 83 and/or channels 115. FIG. 35B illustrates a side view of the cervical wedge composite bone graft of FIG. 35A and includes opposing textured surfaces 117a and 117b, and a vertically disposed channel 118. The top and bottom surfaces of the graft are sloped at angel 119 and 120, respectively. Angle 119 is preferably from about 0° to about 10°, more preferably from about 0° to about 7°, an in this figure it is 0°. Angle 120 is preferably from about 0° to about 10°, more preferably from about 0° to about 7°, and in this figure the angle is 7°, that is the graft slopes at 7°.

Figure 36A:
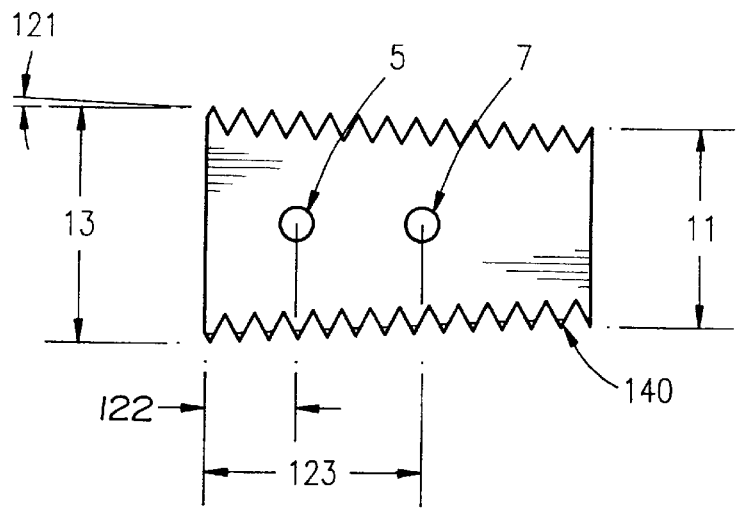
FIGS. 36A, 36B, & 36C.
Figure 36B:
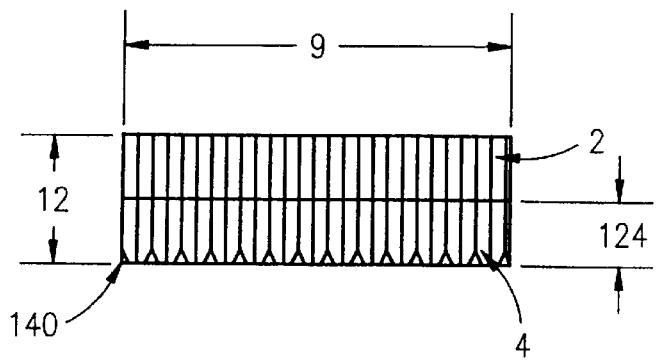
Figure 36C:
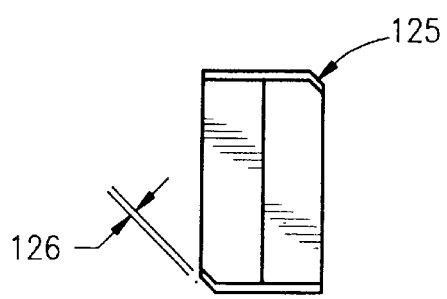

FIGS. 36A, 36B, and 36C, illustrate a trapezoid wedge composite bone graft including two cortical bone portions where 36A is a cross-section view, 36B is a top-view, and 36C is a side view of the width of the composite graft. The composite bone graft includes first and second cortical bone portions 2 and 4, through-holes 5, and a cortical bone pins 7 (The diameter of each bone pin may be the same or different depending on the particular application, implant and size of the graft, the diameter of a pin is preferably about 1.0 to about 5.0 mm, more preferably from about 1.5 to about 4.0 mm, even more preferably from about 2.0 to about 3.5 mm, and most preferably 2.5 to 3.0 mm). The composite bone graft, has a length 9 (preferably from 5.0 to about 50.0 mm, more preferably from about 10.0 to about 30.0 mm, even more preferably from about 15.0 mm to about 25.0 mm, and most preferably about 21.0 mm to 23 mm), an anterior (shorter) height 11 (preferably from about 3.0 mm to about 30.0 mm, more preferably from about 5.0 mm to about 25.0 mm, even more preferably from about 8.0 mm to about 15.0 mm), a posterior (longer) height 13 (preferably from about 5.0 mm to about 50.0 mm, more preferably from about 7.0 mm to about 25.0 mm, and even more preferably from about 10.0 to about 15.0 mm), a composite width 12 (preferably from about 4.0 mm to about 20.0 mm, more referably from about 5.0 mm to about 15.0 mm, section widths 124, which are preferably from about 2.0 mm to about 5.0 mm, more preferably from about 2.5 mm to about 4.0 mm, and most preferably about 3.5 mm±0.5 mm. The bone graft has a length 122 (for example when the length of the graft is 23.0 mm, length 122 is preferably about 5.5 mm) which is the length of the graft measured from the posterior (longer) end to the center of the first pin 7, a length 123 (for example when the length of the graft is 23.0 mm, length 123 is preferably about 13.5 mm) which is the length of the graft measured from the posterior (longer) end to the center point of the second pin 7. The graft is chamfered diametrically opposed edges including edge 140 at an angle 125 of preferably about 45° at a depth 126 of preferably about 0.5 mm. The wedge graft has a slope 121 of preferably from about 3.0° to about 13.0°, more preferably from about 5.0° to about 11.0° and most preferably about 5.4° or 10.8° depending on the anterior and posterior heights.

Figure 37:
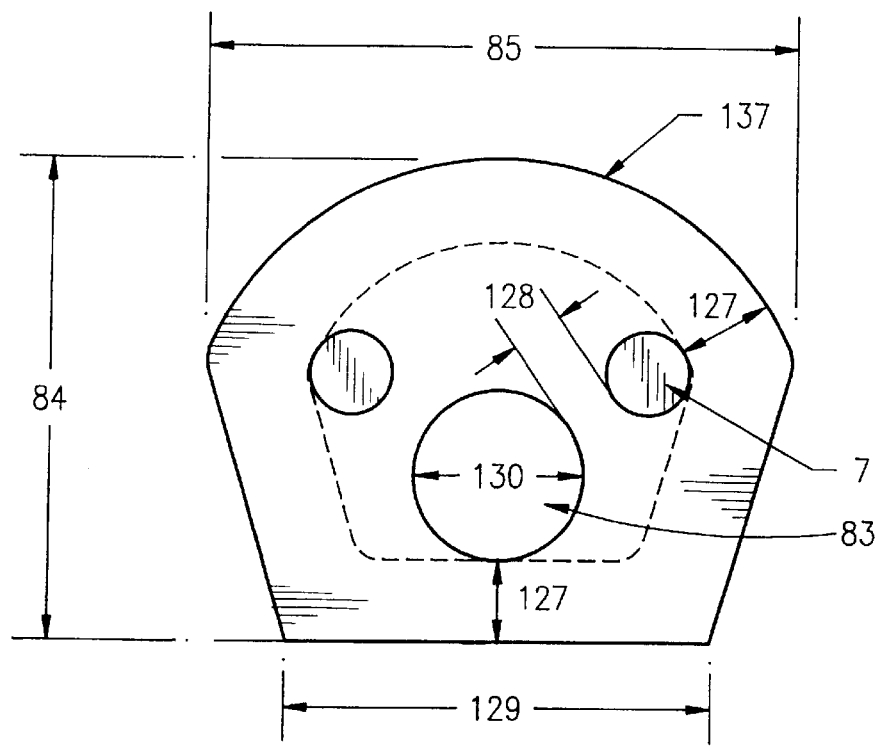
FIG. 37.

FIG. 37 illustrates a cross-section view of a cervical wedge composite bone graft (flattened curved wedge composite bone graft) for use in cervical fusions. The flattened curved wedge composite bone graft includes two or more cortical bone portions held together by two cortical bone pins 7 to form a pinned graft unit, and the pinned graft unit having a hole 83 disposed there through located between pins 7 and having a diameter 130 of from about 3.0 mm to about 7.0 mm, more preferably from about 4.0 mm to about 6.0 mm and most preferably about 4.0 mm to 5.0 mm. The distance 127 between hole 83 and second width 129, and between pins 7 and arc 137, is preferably 1.0 mm to 3.5 mm, more preferably about 1.5 mm to about 3.0 mm and even more preferably about 2.0 mm. The distance 28 between hole 8 and pins 7 is preferably from 1.5 mm to 3.5 mm, more preferably from 2.0 mm to about 3.0 mm, and most preferably is about 2.25 mm to 2.75 mm. The cervical fusion graft has a diameter 84 of from about 10.0 mm to about 20.0 mm, more preferably from about 12.0 mm to about 16.0 mm, and most preferably about 12.0 mm to 14.0 mm, a width 85 of from about 14.0 mm to about 24.0 mm, more preferably from about 15.0 mm to about 20.0 mm, and most preferably about 15.5 mm to 17.5 mm and a second width 129 of from about 8 mm to about 16.0 mm, more preferably from about 10.0 to about 14.0 mm, and most preferably about 11.0 mm to12.0 mm. Slope 136 is preferably about 15° to about 30°, more preferably about 20° to about 25°, and most preferably about 20°.

Figure 38:
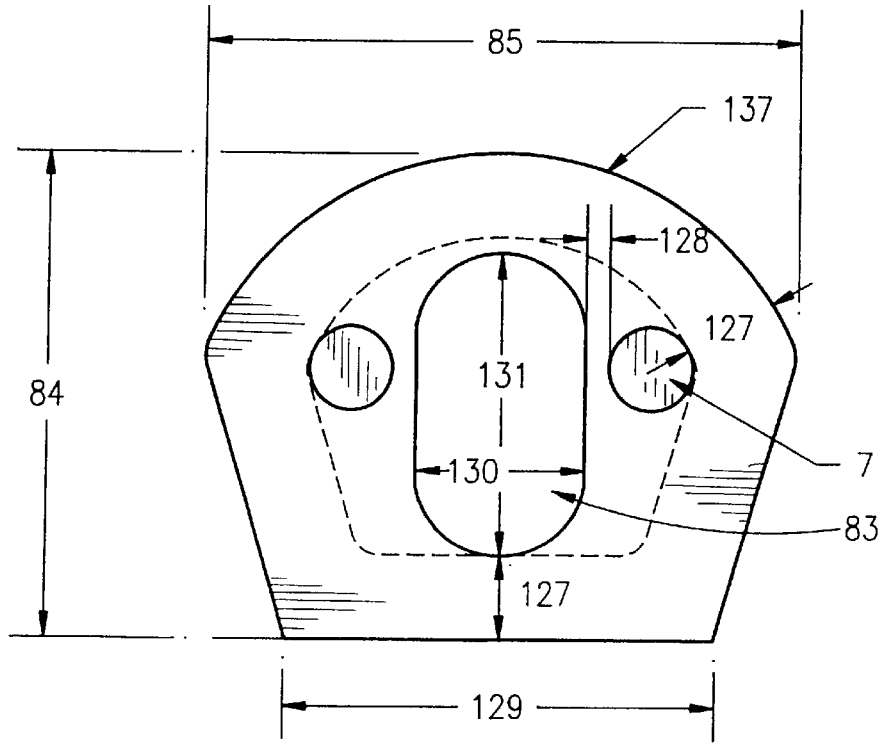
FIG. 38.

FIG. 38 illustrates a cross-section view of a cervical wedge composite bone graft (flattened curved wedge composite bone graft) for use in cervical fusions. The flattened curved wedge composite bone graft includes two or more cortical bone portions held together by two cortical bone pins 7 to form a pinned graft unit, and the pinned graft unit having a hole 83 disposed there through located between pins 7 and hole 83 having a height 131 of from about 5.0 mm to about 15.0 mm, more preferably from about 6.0 mm to about 12.0 mm, and most preferably about 8.0 mm to 10.0 mm, and having a width 130 of from 3.0 mm to about 7.0 mm, more preferably from about 4.0 mm to about 6.0 mm, and most preferably about 4.0 mm to 5.0 mm. The distance 127 between hole 83 and second width 129, and between pins 7 and arc 137, is preferably 1.0 mm to 3.5 mm, more preferably about 1.5 mm to about 3.0 mm and even more preferably about 2.0 mm. The distance 128 between hole 83 and pins 7 is preferably from 1.5 mm to 3.5 mm, more preferably from 1.0 mm to about 3.0 mm, and most preferably is about 2.0 mm. The cortical fusion graft has a diameter 84 of from about 10.0 mm to about 20.0 mm, more preferably from about 12.0 mm to about 16.0 mm, and most preferably about 12.0 mm to 14.0 mm, a width 85 of from about 14.0 mm to about 24.0 mm, more preferably from about 15.0 mm to about 20.0 mm, and most preferably about 15.5 mm to 17.5 mm, and a second width 129 of from about 8.0 mm to about 16.0 mm, more preferably from about 10.0 mm to about 14.0 mm, and most preferably about 11.0 mm to 12.0 mm . Slope 136 is preferably about 15° to about 30°, more preferably about 20° to about 25°, and most preferably about 20°.

Figure 39:
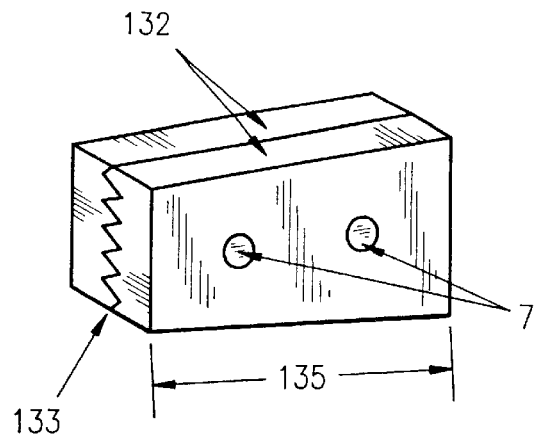
FIGS. 39.

FIG. 39 illustrates a perspective view of a preferred composite bone graft including cortical bone portions 132, and a cortical bone pins 7. The cortical bone portions 132 are patterned with grooves 133 running in direction 135 to provide an interlocking fit between the bone portioris 132.

Figure 40A:
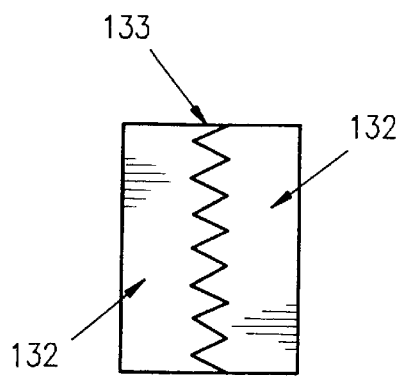
FIGS. 40A & 40B.
Figure 40B:
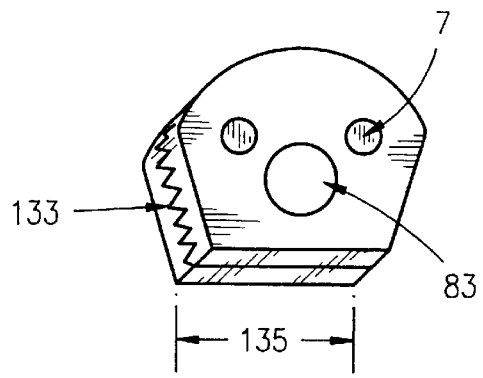

FIGS. 40A and 40B illustrate a wedge composite bone graft (flattened curved wedge composite bone graft) for use in cervical fusions where 14A is a standing side view, and 14B is a perspective view. The flattened curved wedge composite bone graft includes first and second cortical bone portions 132 held together by two cortical bone pins 7 to form a pinned graft unit, and the pinned graft unit having a hole 83 disposed there through located between pins 7. The cortical bone portions 132 are patterned with grooves 133 running in direction 135 to provide an interlocking fit between the bone portions 132.

Figure 41:
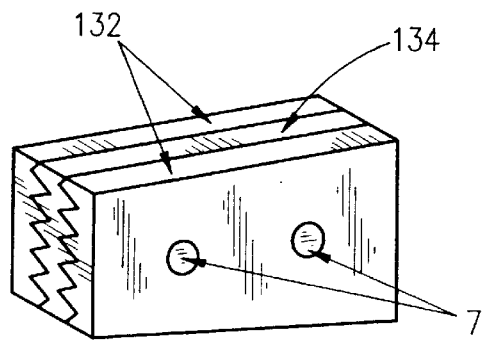
FIG. 41.

FIG. 41 illustrates aperspective view of a preferred composite bone graft including cortical bone portions 132 and 134, and a cortical bone pins 7. The cortical bone portions 132 and 134 are patterned with grooves 133 running in direction 135 to provide an interlocking fit between the bone portions 132.

Figure 42A:
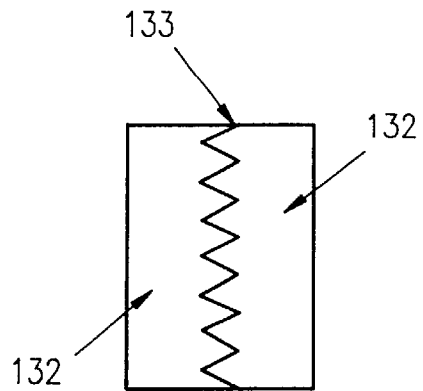
FIGS. 42A, 42B, & 42C.
Figure 42B:
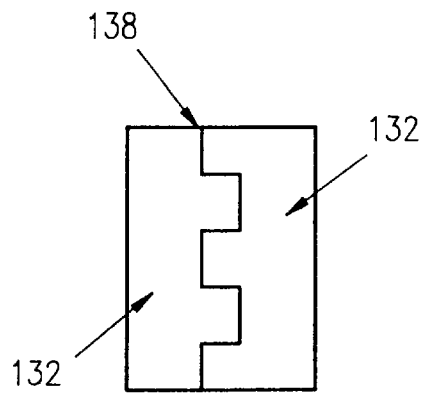
Figure 42C:
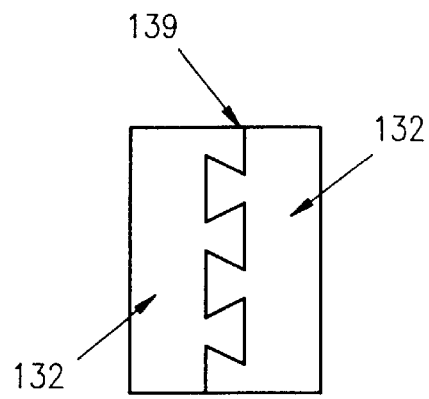

FIGS. 42A, 42B, and 42C illustate side views of a preferred composite bone graft including two patterned cortical bone portions 132 having a pattern 133, 138, and 139, respectively, where the bone portions are interlocked with each other. FIG. 42C illustrates a self-locking, interlocking pattern 139.

Figure 43:
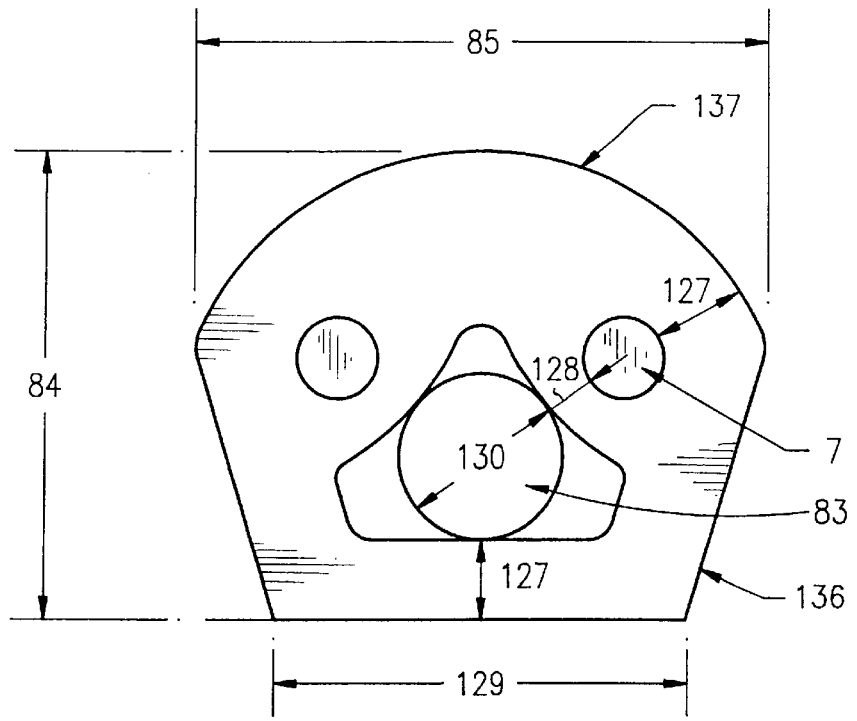
FIG. 43.

FIG. 43 illustrates a cross-section view of a cervical wedge composite bone graft (flattened curved wedge composite bone graft) for use in cervical fusions. The flattened curved wedge composite bone graft includes two or more cortial bone portions held together by two cortical bone pins 7 having a diameter of from 1.0 mm to about 4.0 mm, preferably from about 2.0 mm to about 3.0 mm and more preferably about 2.5 mm, to form a pinned graft unit, and the pinned graft unit having a hole 83 disposed there through located between pins 7, and hole 83 having a width 130 of from 3.0 mm to about 7.0 mm, more preferably from about 4.0 mm to about 6.0 mm, and most preferably about 4.0 mm to 5.0 mm. The distance 127 between 83 and second width 129, and between pins 7 and arc 137, is preferably 1.0 mm to 3.5 mm, more preferably about 1.5 mm to about 3.0 mm and even more preferably about 2.0 mm. The distance 128 between hole 83 and pins 7 is preferably from 1.5 mm to 3.5 mm, more preferably from 1.0 mm to about 3.0 mm, and most preferably is about 2.0 mm. The cervical fusion graft has a diameter 84 of from about 11.0 mm to about 20.0 mm, more preferably from about 12.0 mm to about 16.0 mm, and most preferably about 11.0 mm to 13.0 mm, a width 85 of from about 10.0 mm to about 24.0 mm, more preferably from about 12.0 mm to about 20.0 mm, and most preferably about 13.5 mm to 15.5 mm, and a second width 129 of from about 4.0 mm to about 12.0 mm, more preferably from about 6.0 mm to about 10.0 mm, and most preferably about 7.0 mm to about 8,0 mm. Slope 136 is preferably about 25°.

Figure 44:
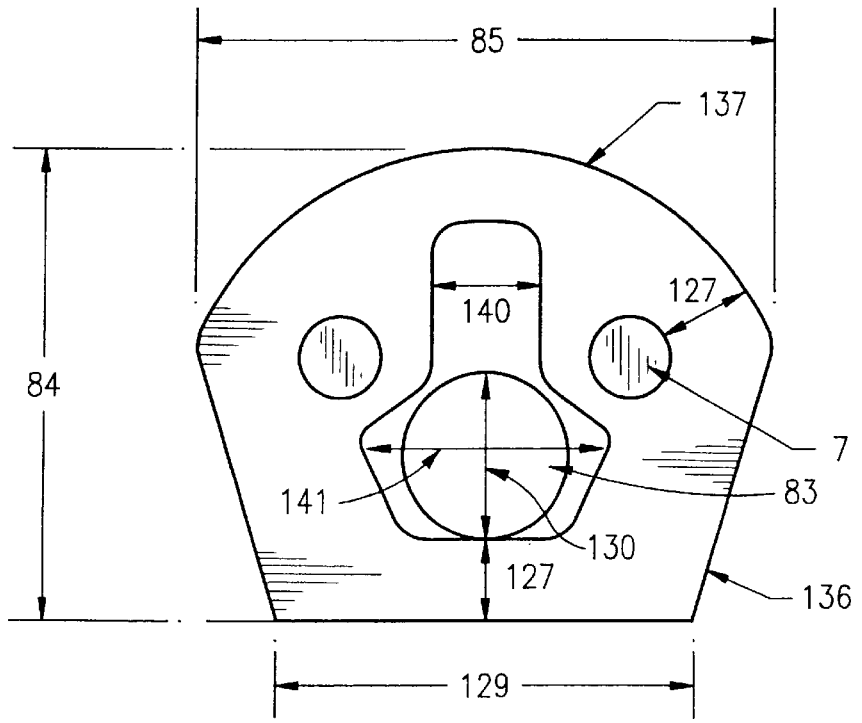
FIG. 44.

FIG. 44 illustrates a cross-section view of a cervical wedge composite bone graft (flattened curved wedge composite bone graft) for use in cervical fusions. The flattened curved wedge composite bone graft includes two or more cortical bone portions held together by two cortical bone pins 7 having a diameter of from 1.0 mm to about 4.0 mm, preferably from about 2.0 mm to about 3.0 mm and more preferably about 2.5 mm, to form a pinned graft unit, and the pinned graft unit having a hole 83 disposed there through located between pins 7, and hole 83 having a diameter 130 of from 3.0 mm to about 9.0 mm, more preferably from about 4.0 mm to about 8.0 mm, and most preferably about 6.0 mm to 7.0 mm, and a width 141 of from about 5.0 mm to about 13.0 mm, preferably from about 7.0 mm to about 11.0 mm, more preferably from about 8.5 mm to about 9.5 mm, and most preferably about 9.0 mm. Hole 113 has a second width 140 of from about 2.0 mm to about 6.0 mm, preferably from about 3.0 mm to about 5.0 mm, and more preferably form about 3.5 mm to about 4.5 mm. The distance 127 between hole 83 and second width 129, and between pins 7 and arc 137, is preferably 1.0 mm to 3.5 mm, more preferably about 1.5 mm to about 3.0 mm and even more preferably about 2.0 mm. The cervical fusion graft has a diameter 84 of from about 10.0 mm to about 20.0 mm, more preferably from about 12.0 mm to about 16.0 mm, and most preferably about 13.0 mm to 15.0 mm, a width 85 of from about 10.0 mm to about 24.0 mm, more preferably from about 12.0 mm to about 20.0 mm, and most preferably about 16.5 mm to 18.5 mm, and a second width 129 of from about 6.0 mm to about 14.0 mm, more preferably from about 8.0 mm to about 12.0 mm, and most preferably about 9.0 mm to 11.0 mm. Slope 136 is preferably about 25°.

The present composite bone graft can include two or more bone portions, including any combination of cancellous and cortical bone portions, or cancellous or cortical bone portions alone, where the bone portions may optionally be demineralized, and may optionally be discontinuous, where the bone portions are connected, for example by interlocking the bone portions, and/or by one or more mechanical and/or chemical connectors. Any cancellous bone portion and/or discontinuous bone portion (cortical and/or cancellous), and/or any demineralized bone portion (cortical and/or cancellous) may optionally include one or more pharmaceutically active agents or therapeutically beneficial substances provided therein, for example provided in the matrix of cancellous bone, or provided in any artificially created void areas. Both the cortical and cancellous bone portions may be solid and continuous or may be discontinuous (i.e. include one or more "holes" or "perforations" of any shape disposed at regular or random intervals throughout the bone portion. Bone portions may be provided with a pattern to enable an interlocking fit between cortical bone portions.

Suitable mechanical connectors include pin-type structures having any cross-section shape, such shapes including for example, round, square, triangular, rectangular, hexagon, pentagon, oval, and irregular. The pin-type structure can include surface modification, for example the surface can be roughened, or provided with a plurality of horizontally or vertically disposed grooves (horizontal or vertically relative to the length of the pin); horizontally or vertically disposed ridges; or helical threads. The pin or surface-modified pin an also include one or more slots extending partially or entirely through the diameter of the pin, an extending partially or entirely through the length of the pin, suitable slots include for example, a slot extending partially through the diameter of the pin, for example about half-way through the diameter of the pin, and through the entire length of the pin; and a slot extending entirely through the diameter of the pin, and extending through a partial length of the pin for example, extending at least halfway through the length of the pin, preferably extending no more than about seven-eighths the length of the pin. Suitable mechanical connectors also include cotter pins. A composite graft can be pinned with one or more biocompatible pins, where the pins have substantially the same diameter or have a diameter different from each other. Suitable diameters can be readily selected and employed by one of ordinary skill in the art to which the present invention pertains without undu experimentation depending upon, for example, the particular application and implantation site, and the size and shape of the composite graft. The composite graft can be pinned with one or more biocompatible pins, entirely or partially traversing a dimension of the graft, for example, the height, length, and/or width of the composite graft. One of ordinary skill in the art to which the present invention pertains can readily select an appropriate pin, number of pins, and determine the orientation of the pin or pins, based on for example, the particular graft, whether the graft is interlocking or not, the orientation of the graft in the body, and the clinical indication, without undue experimentation.

Suitable chemical connectors include any biocompatible adhesive. Such adhesives are well known to those of ordinary skill in the art to which the present invention pertains, and can be readily selected and employed by those of ordinay skill in the art, without undue experimentation. Suitable chemical connectors also include known methods of biochemical surface modification. Such methods are well known to those of ordinary skill in the art to which the present invention pertains, and can be readily selected and employed by those of ordinary skill in the art, without undue experimentation.

The chemical and/or mechanical (connectors may be used alone or in any combination and may include one or more therapeutically beneficial substances including for example, one or more osteoinductive substances, one or more osteoconductive substances and one or more pharmaceutically active agents.

The through-hole(s) of the composite bone graft may also include surface modification as described above for the present mechanical connectors configured to accomadate a particular mechanical connector. For example, if a threaded cortical bone pin is used, the through-hole or holes can optionally be threaded. The through-hole(s) can traverse any dimension of the graft, provided that they are placed such that when graft unit is connected the graft is held together. One of ordinary skill in the art to which the present invention pertains can readily select an optimum location for the through-holes based on criteria including the following: the anterior and posterior height of the composite bone graft, and the diameter of the mechanical and/or mechanical and chemical connectors, and the height of the protrusions. For example, when the anterior height is relatively small (i.e. 7.0 mm) and the diameter of the pin is relatively large (i.e.2.5–3.0 mm), the through-holes can be spaced equidistant along the length of the graft unit, or displaced toward the posterior end of the graft unit.

The graft unit can be connected with one or more mechanical connectors. Suitable connection include any connection which is adequate to hold the bone portions of the graft unit together. Such connections include, for example, an interference or friction connection where the diameter of the pin is the same as or slightly larger than (preferably no more than 1.5 mm larger than the diameter of the through-hole) the diameter of the corresponding through-hole; a slidable connection where the diameter of the pins the slightly less than the diameter of the through-hole, and a compression fit, where the pin is configured to allow compression upon insertion where the pin expands after insertion, achieved for example, by providing the pin with a slot.

The mechanical connector of the invention, including pin-like connectors can be composed of any biocompatible material sufficient to hold together the present graft unit. Suitable biocompatible materials include for example, cortical bone; stainless steel; titanium; cobalt-chromium-molybdenum alloy; and a plastic for example, of one or more of the following: nylon, polycarbonate, polypropylene, polyacetal, polyethylene, and polysulfone, where the plastic can optionally include fibers; and a polymer including one or more bioabsorbable polymers including resorbable calcium phosphates; bioceramrics and/or glasses including for example bioactive glasses and glass-cerarnics; and calcium phosphate ceramics. Such mechanical connectors including for example, bioabsorbable polymers may optionally include one or more active agents, including for example one or more pharmaceutically active agents and/or one or more therapeutically beneficial agents, provided on the surface or impregnated in the matrix of the material.

The surface of the mechanical connector can be modified by methods well known to those of ordinary skill in the art to which the invention pertains, and include for example the following: (a) modification to influence cell adhesion and growth, provided by: (I) oxidized polystyrene surface, (ii) ammonia plasma-treated surface, and (iii) plasma-deposited acetone or methanol film; (b) modification to control protein adsorption; and (c) modification to improve lubricity.

The composite bone graft preferably has a shape including for example, a square, rectangular or curved block; a flattened curved wedge (ie. a cervical wedge for use in cervical fusion); a wedge; a trapezoid wedge; a polyhedron block a parallelepiped; a cylinder or dowel having a uniform diameter or a decreasing or increasing diameter, for example a tapered cylinder or tapered dowel; a dowel or tapered dowel having a cross-section of a shape including for example, round, oval, square, rectangular, triangular, pentagon, or hexagon.

The composite bone graft can include one or more partially or completely textured surfaces. Preferably, a textured composite bone graft includes opposing textured surfaces disposed perpendicular to the interface(s) of the bone portions. The textured surface of the composite bone graft includes a plurality of protrusions. The protrusions can be formed over an entire surface of the composite bone graft or over a portion of a surface, for example over the entire cut surfaces, or over a portion of the cut surfaces. The plurality of protrusions can be formed on the surface in any number of ways well known to those of ordinary skill in the art to which the present invention pertains, including for example mechanical and/or chemical methods, including for example, by forming a series of parallel linear or curved grooves. The bone allograft protrusions can be formed by milling, for example by milling a set of parallel linear groves to form a saw-tooth configuration on the cut surface of the composite graft to form continuous linear protrusions; by milling a first set of parallel linear groves followed by turning the graft and forming a second set of parallel grooves at an angle to the first series, for example at a 90° angle to form a plurality of discrete pyrimidal protrusions. Milling is preferably achieved, by for example: running the graft over a milling tool which includes a plurality of closely space blades which can be adjusted to achieve a desired height and width; to form the discrete pyrimidal rotrusions, the graft can then be turned at, for example, a 90° angle and again run over the milling tool to produce the discrete protrusions illustrated. Milling can also be achieved using for example a routing or dremel tool, a laser, and masking and acid etching.

Other protrusions, for example concentric rings or other curved or irregular, or regular protrusions can be provided by attaching a drill bit having a blade corresponding to the protrusion pattern desired where the blade is appropriately sized to provide a desired protrusion width, length, and height, to a drill and drilling the desired surface of the bone to achieve the desired textured surface. One of ordinary skill in the art can readily design and produce, or select, and employ an appropriate milling tool to achieve a desired textured surface on a bone allograft, without undue experimentation.

Preferably, the protrusions (discrete, continuous, or a combination thereof) present on one or more surfaces of the present allograft are closely spaced, preferably from about 0.0 to 3.0 mm apart, preferably 0.1 to 2.0 mm apart, more preferably about 0.2 to 1.5 mm apart, and most preferably about 0.5 mm apart, (that is, there is preferably a distance of from 0.0 to 3.0 mm between the edges of two adjacent protrusions). The protrusions preferably have a height of from 0.1 to 5.00 mm, preferably 0.3 to 3.0 mm, more preferably 0.5 to 1.5 mm, and even more preferably 0.75 mm to 1.3 mm, and most preferably about 1.2 mm.

The composite bone graft may include one or more void areas. Examples of such grafts include a composite graft having for example a first and a second cortical bone portion where the bone portions are for example slidably connected with for example one or more bone pins, where the first and second bone portion are disposed apart thereby creating a centrally located void. The void may optionally include any pharmiceutically active agent and/or therapeutically beneficial agent, including for example, osteoinducive substances including for example, bone morphogenic protein, hydroxyapitate, demineralized bone and bone products including for example GRAFTON and DYNEGRAFT, and autograft bone; such substances may be in any form including for example, in the form of a paste, gel, or sponge.

IV. Use of the Composite Bone Grafts

The present composite bone graft, are useful in spinal applications including restoration of column support and are preferably used from the posterior approach. Composite grafts suitable for posterior lumbar interbody fusions include for example the following described in detail below: (a) composite bone grafts having a trapezoid wedge shape and optionally having opposing textured surfaces disposed perpendicular to the interfaces of the bone portions, (b) composite bone grafts having a parallel block shape and optionally having opposing textured surfaces disposed perpendicular to the interfaces of the bone portions, (c) composite bone grafts having a large square block shape and optionally having opposing textured surfaces disposed perpendicular to the interfaces of the bone portions, (d) composite bone graft blocks having a flattened curved wedge shape and optionally having opposing textured surfaces disposed perpendicular to the interfaces of the bone portions for use in for example, cervical fusion, (which can be used from an anterior or posterior approach) and (e) composite bone grafts having an ovoid wedge shape for performing anterior fusions (which can be used from an anterior or posterior approach).

The term "about" used below and throughout this disclosure in reference to specific dimensions means that the tolerance limits for overall or outer dimensions of the composite bone graft is plus or minus (+/−) 1.0 mm, and the tolerance limits for the width of individual cortical bone portions is plus or minus (+/−) 0.5 mm.

The composite bone grafts having a trapezoid wedge shape, the shape as shown in FIG. 1, and optionally having opposing textured surfaces disposed perpendicular to the interfaces of the bone portions, preferably include two or more bone portions where the bone portions can be cortical or cancellous bone portions or a combination thereof, each bone portion having a width of from about 1.5 mm to about 10.0 mm, preferably from about 2.0 mm to about 7.0 mm, more preferably from about 2.0 mm to about 5.0 mm, and most preferably having a width of about 2.0 mm to about 4.0 mm, to give a composite width of from about 8.0 mm to about 15.0 mm, preferably from about 9.0 mm to about 13.00 mm, and more preferably about 11.0 mm.

The trapezoid wedge composite bone graft has a front (anterior) height which is smaller than its back (posterior) height, the anterior height being from about 5.0 mm to about 15.0 mm, preferably from about 6.0 mm to about 13.0 mm, more preferably from about 7.0 mm to about 12.0 mm, and most preferably about 8.0 mm, 9.0 mm, 10.0 mm, 12.0 mm, or 14.0 mm; the posterior height being from about 7.0 mm to about 20.0 mm, preferably from about 8.0 mm to about 17.0 mm, more preferably from about 9.0 mm to about 15.0 mm, and most preferably the posterior height is about 7.0 mm, 10.0 mm, 11.0 mm, 12.0 , mm or 14.0 mm ; and the trapezoid wedge composite bone graft has a length of from about 15.0 mm to about 35.0 mm, preferably from about 17.0 mm to about 30.0 mm, more preferably from about 20.0 mm to about 27.0 mm, and most preferably a length of about 21.0 mm, or 23.0 mm.

The bone portions may be interlocking and/or connected with one or more mechanical and/or chemical biocompatible connectors. The preferred connectors include mechanical connectors including for example, one or more cortial bone pins having a round cross-section and having a diameter of from about 1.0 mm to about 6.0 mm, preferably from about 2.0 mm to about 5.0 mm, more preferably from about 2.0 mm to about 4.5 mm, and most preferably a pin diameter of from about 2.0 mm to about 4.0 mm, where the diameter of each pin in a single graft may be the same or different. The diameter of the two corresponding through-holes is preferably sufficient to provide an interference or frictional or slidable connection between the bone portions and the pin, preferably a interference or frictional connection. The foregoing described trapezoid wedge composite optionally includes a cancellous bone portion disposed between the two cortical bone portions and having the same width or a greater width than the cortical bone portions. The trapezoid wedge composite graft can optionally include diametrically opposed chamfered edges.

Most preferable trapezoid wedge composite bone grafts include the following configurations:

(a) a first cortical portion having a width of from about 3.0 mm to about 4.0 mm, preferably about 4.0 mm; a second cortical bone portion having a width of from about 3.0 mm to about 4.0 mm, preferably about 4.0 mm; a central cancellous bone portion having a width of from about 3.0 mm to about 5.0 mm, preferably about 3.0 mm disposed there between, forming a graft unit, the graft unit held together by two round cortical bone pins having a diameter of from about 2.0 mm to about 4.0 mm, the composite graft having an overall length of about 21.0 mm, an anterior height of about 9.0 mm, and a posterior height of about 11.0 mm; or an anterior height of about 8.0 mm and a posterior height of about 10.0 mm, or an anterior height of about 10.0 mm and a posterior height of about 12.0 mm, or an anterior height of about 12.0 mm and a posterior height of about 14.0 mm.

(b) a first cortical portion having a width of about 4.0 mm; a second cortical bone portion having a width of about 4.0 mm; a central cancellous bone portion having a width of about 3.0 mm disposed there between forming a graft unit, the graft unit held together by two round cortical bone pins having a diameter of about 3.0 mm, th composite graft having an overall length of about 21.0 mm, an anterior height of about 9.0 mm, and a posterior height of about 11.0 mm, or an anterior height of about 8.0 mm and a posterior height of about 10.0 mm, or an anterior height of about 10.0 mm and a posterior height of about 12.0 mm, or an anterior height of about 12.0 mm and a posterior height of about 14.0 mm; and where the length of the graft measured from the posterior end to the center of the first pin is about 5.5 mm, the length of the graft measured from the center point of a first pin to a center point of a second pin is about 8.0 mm and, the length of the graft measured from a center point of a second pin to the anterior end of the graft is about 7.5 mm, and optionally having opposing textured surfaces where the protrusions are in a saw-tooth pattern, and have a height of about 1.2 mm and have an angle of about 60° between protrusions;

(c) a first cortical portion having width of about 3.0 mm; a second cortical bone portion having a width of about 3.0 mm; a central cancellous bone portion having a width of about 3.0 mm disposed there between forming a graft unit, the graft unit held together by two round cortical bone pins having a diameter of about 4.0 mm, the composite graft having an overall length of about 21.0 mm, an anterior height of about 7.0 mm, and a posterior height of about 9.0 mm, or an anterior height of about 8.0 mm and a posterior height of about 10.0 mm, or an anterior height of about 10.0 mm and a posterior height of about 12.0 mm, or an anterior height of about 12.0 mm and a posterior height of about 14.0 mm; and where the length of the graft measured from the posterior end to the center of the first pin is about 6.0 mm, the length of the graft measured from the center point of a first pin to a center point of a second pin is about 9.0 mm and, the length of the graft measured from a center point of a second pin to the anterior end of the graft is about 6.0 mm, and optionally having opposing textured surfaces where the protrusions are in a saw-tooth pattern, and have a height of about 1.2 mm and have an angle of about 60° between protrusions;

(d) a first cortical portion having a width of about 3.0 mm, a second cortical bone portion having a width of about 3.0 mm, a central cancellous bone portion having a width of about 5.0 mm disposed there between, forming a graft unit, the graft unit held together by two round cortical bone pins having a diameter of about 2.0 mm to about 4.0 mm, the composite graft having an overall length of about 21.0 mm, an anterior height of about 9.0 mm, and a posterior height of about 11.0 mm;

(e) a first cortical portion having a width of about 3.0 mm, a second cortical bone portion having a width of about 3.0 mm, a central cancellous bone portion having a width of about 7.0 mm disposed there between, forming a graft unit, the graft unit held together by two round cortical bone pins having a diameter of about 2.0 mm to about 4.0 mm, the composite graft having an overall length of about 21.0 mm, an anterior height of about 11.0 mm, and a posterior height of about 13.0 mm;

(f) a first cortical portion having a width of about 3.0 mm, a second cortical bone portion having a width of about 3.0 mm, a central cancellous bone portion having a width of about 3.0 mm disposed there between, forming a graft unit, the graft unit held together by two round cortical bone pins having a diameter of about 2.0 to about 4.0 mm, the composite graft having an overall length of about 21.0 mm, an anterior height of about 7.0 mm, and a posterior height of about 9.0 mm;

(g) a first cortical portion having width of about 4.0 mm, a second cortical bone portion having a width of about 4.0 mm forming a graft unit, the graft unit held together by two round cortical bone pins having a diameter of about 3.0 mm, the composite graft having an overall length of about 25.0 mm, an anterior height of about 12.0 mm, and a posterior height of about 15.0 mm;

(h) a first, second, third and fourth cortical bone portion each having a width of from about 2.0 mm to about 3.0 mm, preferably about 2.0 mm, a first cancellous bone portion having a width of from about 2.0 mm to about 3.0 mm, referably about 3.0 mm, where the first cortical bone portion is disposed on the second cortical one portion, the first cancellous bone portion is disposed between the second and third cortical bone portions, and the fourth cortical bone portion is disposed on the third cortical bone portion, forming a graft unit, the graft unit held together by two round cortical bone pins having a diameter of about 2.0 mm to about 4.0 mm, the composite graft having an overall length of about 21.0 mm, an anterior height of about 9.0 mm, a posterior height of about 11.0 mm, and a composite width of about 11.0 mm;

(i) a combination of at least two cortical bone portions optionally having a cancellous bone portion disposed therebetween, and having (1) a posterior height of 9.0 mm an anterior height of 7.0 mm, a length of 21.0 mm, and a composite width of 12.0 mm; (2) a posterior height of 9.0 mm an anterior height of 7.0 mm, a length of 25.0 mm, and a composite width of 12.0 mm; (3) a posterior height of 11.0 mm, an anterior height of 9.0 mm, a length of 23.0 mm, and a composite width of 12.0 mm; (4) a posterior height of 11.0 mm, an anterior height of 9.0 mm, a length of 25.0 mm, and a composite width of 12.0 mm; (5) a posterior height of 13.0 mm, an anterior height of 11.0 mm, a length of 25.0 mm, and a compsite width of 12.0 mm; and (6) a posterior height of 15.0 mm, an anterior height of 13.0 mm, a length of 25.0 mm, and a composite width of 12.0 mm; and (j) a combination of two or more cortical bone portions optionally each having a patterned surface such that an interlocking fit between the bone portions is provided, and having: (1) a posterior height of 14.0 mm an anterior height of 10.0 mm, a length of 21.0 mm, and a composite width of 7.0 mm, two cortical bone pins each having a diameter of 3.0 mm, and a slope of 10.8°, and having diametrically opposed chamfered edges at 45° and 0.5 mm in depth, a distance from the center of the first pin to the center point of the second pin of 8 mm, and a distance from the anterior end of the graft to the center point of the first pin of 7.5 mm; (2) a posterior height of 12.0 mm an anterior height of 10.0 mm, a length of 21.0 mm, and a composite width of 7.0 mm, two cortical bone pins each having a diameter of 3.0 mm, and a slope of 5.45°, having diametrically opposed chamfered edges at 45° and 0.5 mm in depth, a distance from the center of the first pin to the second of the second pin of 8.0 mm, and a distance from the anterior end of the graft to the center point of the first pin of 7.5 mm; (3) a posterior height of 14.0 mm an anterior height of 12.0 mm, a length of 21.0 mm, and a composite width of 7.0 mm, two cortical bone pins each having a diameter of 3.0 mm, and a slope of 5.45°, having diametrically opposed chamfered edges at 45° and 0.5 mm in depth, a distance from the center of the first pin to the second of the second pin of 8 mm, and a distance from the anterior end of the graft to the center point of the first pin of 7.5 mm; (4) a posterior height of 11.0 mm, an anterior height of 9.0 mm, a length of 25.0 mm, and a composite width of 12.0 mm; (5) a posterior height of 12.0 mm an anterior height of 9.8 mm, a length of 23.0 mm, and a composite width of 7.0 mm, two cortical bone pins each having a diameter of 3.0 mm, and a slope of 5.5°, having diametrically opposed chamfered edges at 45° and 0.5 mm in depth, a distance from the center point of the second pin to the posterior end of the graft of 13.5 mm, and a distance from the center point of the first pin to the posterior end of the graft 5.5 mm; (6) a posterior height of 14.0 mm an anterior height of 9.8 mm, a length of 23.0 mm, and a composite width of 7.0 mm, two cortical bone pins each having a diameter of 3.0 mm, and a slope of 10.8° having diametrically opposed chamfered edges at 45° and 0.5 mm in depth, a distance from the center point of the second pin to the posterior end of the graft of 13.5 mm, and a distance from the center point of the first pin to the posterior end of the graft 5.5 mm; (7) a posterior height of 13.0 mm an anterior height of 9.0 mm, a length of 23.0 mm, and a composite width of 7.0 mm, two cortical bone pins each having a diameter of 3.0 mm, and a slope of 10.8°, having diametrically opposed chamfered edges at 45° and 0.5 mm in depth, a distance from the center point of the second pin to the posterior end of the graft of 13.5 mm, and a distance from the center point of the first pin to the posterior end of the graft of 5.5 mm; (8) a posterior height of 13.0 mm an anterior height of 11.0 mm, a length of 23.0 mm, and a composite width of 7.0 mm, two cortical bone pins each having a diameter of 3.0 mm, and a slope of 5.4°, having diametrically opposed chamfered edges at 45° and 0.5 mm in depth, a distance from the center point of the second pin to the posterior end of the graft of 13.5 mm, and a distance from the center point of the first pin to the posterior end of the graft 5.5 mm; (9) a posterior height of 11.0 mm an anterior height of 9.0 mm, a length of 23.0 mm, and a composite width of 7.0 mm, two cortical bone pins each having a diameter of 3.0 mm, and a slope of 5.4°, having diametrically opposed chamfered edges at 45° and 0.5 mm in depth, a distance from the center point of the second pin to the posterior end of the graft of 13.5 mm, and a distance from the center point of the first pin to the posterior end of the graft of 5.5 mm; (10) a posterior height of 7.0 mm an anterior height of 5.0 mm, a length of 21.0 mm, two cortical bone pins, and optionally having diametrically opposed chamfered edges; (11) a posterior height of 7.0 mm an anterior height of 5.0 mm, a length of 23.0 mm, two cortical bone pins and optionally having diametrically opposed chamfered edges; and (12) a posterior height of 7.0 mm an anterior height of 5.0 mm, a length of 25.0 mm, two cortical bone pins, and optionally having diametrically opposed chamfered edges.

The composite bone grafts having a parallel block shape and optionally having opposing textured surfaces disposed perpendicular to the interfaces of the bone portions, and optionally having diametrically opposed chamfered edges, preferably include: a combination of two or more bone portions, preferably cortical bone portions, optionally each having a patterned surface such that an interlocking fit between adjacent bone portions is provided; and:

(a) at least two cortical bone portions each having a width of from about 1.5 mm to about 10.0 mm, preferably from about 2.0 mm to about 7.0 mm, more preferably from at about 3.0 mm to about 5.0 mm, and most preferably having a width of about 4.0 mm to give a composite width of about 15.0 mm; the parallel block composite bone graft has a height from about 5.0 mm to about 20.0 mm, preferably from about 7.0 mm to about 19.0 mm, more preferably from about 8.0 mm to about 17.0 mm, and most preferably from about 9.0 mm to about 16.0 mm; and the parallel block composite bone graft has a length of from about 15.0 mm to about 35.0 mm, preferably from about 17.0 mm to about 30.0 mm, more preferably from about 20.0 mm to about 27.0 mm, and most preferably a length of from about 21.0 mm to about 25.0 mm. The preferred mechanical connectors include one or more, preferably two cortical bone pins having a round cross-section and having a diameter of from about 1.0 mm to about 6.0 mm, preferably from about 2.0 mm to about 5.0 mm, more preferably from about 2.5 mm to about 4.5 mm, and most preferably a pin diameter of from about 3.0 mm to about 4.0 mm, where the diameter of each cortical bone pin may be the same of different. The diameter of the two corresponding through-holes is preferably sufficient to provide an interference or frictional or slidable connection between the bone portions and the pin, preferably a interference or frictional connection, and (b) two or more cortical bone po ons layered to form a graft unit, and optionally one or more cancellous bone portions disposed between said cortical bone portions, the graft unit being connected by one or more mechanical connectors, preferably two cortical bone pins having a diameter of from about 1.0 mm to about 6.0 mm, preferably from about 2.0 mm to about 5.0 mm, more preferably from about 2.5 mm to about 4.5 mm, and most preferably a pin diameter of from about 3.0 mm to about 4.0 mm, where the diameter of each pin may be the same or different, and having a composite width of from 4.5 mm to about 30.0 mm, preferably from about 6.0 mm to about 21.0 mm, more preferably from about 9.0 mm to about 15.0 mm, and most preferably having a width of about 4.0 mm to give a composite width of about 12.0 mm to about 15.0 mm, a posterior and anterior height of from about 5.0 mm to about 20.0 mm, preferably from about 9.0 mm to about 17.0 mm, and a length of from about 20.0 mm to about 30.0 mm, specific preferred configurations include the following: following configurations: 1) an anterior and posterior height of about 9.0 mm, and a length of about 25.0 mm; (2) an anteri and posterior height of about 9.0 mm, and a length of about 21.0 mm; (3) an anterior and posteior height of about 11.0 mm, and a length of about 25.0 mm; (4) an anterior and posterior height of about 11.0 mm, and a length of about 21.0 mm; (5) an anterior and posterior height of about 13.0 mm, and a length of about 25.0 mm; (6) an anterior and posterior height of about 11.0 mm, and length of about 23.0 mm; (7) an anterior and posterior height of about 13.0 and a length of about 23.0 mm ; (8) an anterior and posterior height of about 15.0 mm, and a length of about 25.0 mm; and (9) an anterior and posterior height of about 17.0 mm, and a length of about 25.0 mm. The foregoing described parallel block composite bone graft optionally includes a cancellous bone portion disposed between the two cortical bone portions and having the same width or a greater width than the cortical bone portions.

Most preferable parallel block composite bone grafts include the following configurations:

(a) two or more cortical bone portions having a composite width of about 15.0 mm, held together by two round cortical bone pins having a diameter of about 2.0 mm to about 4.0 mm, where each pin has the same or a different diameter, the composite graft having a height of about 16.0 mm and a length of about 25.0 mm, (b) a first cortical portion having a width of about 3.0 mm, a second cortical bone portion having a width of about 3.0 mm, one or more central cancellous bone portions having a composite width of about 9.0 mm disposed there between, forming a graft unit, the graft unit held together by two round cortical bone pins having a diameter of about 2.0 mm to about 4.0 mm, where the diameter of each pin is the same or different, the composite graft having a height of about 16.0 mm and an overall length of about 25.0 mm, the parallel block composite bone graft also includes opposing textured surfaces disposed perpendicular to the interfaces of the bone portions;

(c) a first cortical bone portion having a width of about 3.0 mm, a second cortical bone portion having a width of about 3.0 mm, a central cancellous bone portion having a width of about 3.0 mm disposed there between, forming a graft unit, the graft unit held together by two round cortical bone pins having a diameter of about 2.0 mm to about 4.0 mm, where the diameter of each bone pin is the same or different, the composite graft having a height of about 10.0 mm and a length of about 25.0 mm, the parallel block composite bone graft also includes opposing textured surfaces disposed perpendicular to the interfaces of the bone portions;

(d) a first cortical portion having a width of about 3.0 mm, a second cortical bone portion having a width of about 3.0 mm, a central cancellous bone portion having a width of about 3.0 mm disposed there between, forming a graft unit, the graft unit held together by two round cortical bone pins having a diameter of about 2.0 mm to about 4.0 mm, where the diameter is the same or different, the composite graft having a height of about 9.0 mm and a length of about 21.0 mm, (e) a first cortical portion having a width of about 3.0 mm, a second cortical bone portion having a width of about 3.0 mm, a central cancellous bone portion having a width of about 5.0 mm disposed there between, forming a graft unit, the graft unit held together by two round cortical bone pins having a diameter of about 2.0 mm to about 4.0 mm, where the diameter of each bone pin is the same or different, the composite graft having a height of about 11.0 mm and a length of about 21.0 mm, and (f) a first cortical portion having width of about 3.0 mm, a second cortical bone portion having a width of about 3.0 mm, a central cancellous bone portion having a width of about 7.0 mm disposed there between, forming a graft unit, the graft unit held together by two round cortical bone pins having a diameter of about 2.0 mm to about 4.0 mm, where the diameter of each bone pin is the same or different, the composite graft having a height of about 13.0 mm and a length of about 21.0 mm.

Most preferable cortical block composite bone grafts include the following configurations: (a) a plurality of cortical bone portions each having a width of from about 3.0 mm to about 4.0 mm, preferably about 3.0 mm and the plurality of cortical bone portions having a composite width of from about 18.0 to about 22.0 mm, preferably a composite width of about 20.0 mm, the cortical block composite has a height of from about 18.0 to about 22.0 mm, preferably of about 20.0 mm and a length of from about 18.0 to about 22.0 mm, preferably of about 20.0 mm or 21.0 mm, with the graft unit held together by two round cortical bone pins having a diameter of about 2.0 mm to about 4.0 mm, where the diameter of each pin is the same or different, and (b) the cortical block composite bone graft of (a) where one or more of the central cortical bone portions are replaced with one or more cancellous bone portions having an overall width of from about 3.0 to about 15.0 mm, preferably about 14.0 mm.

Most preferable cervical wedge grafts (flattened curved wedge composite bone grafts) for cervical fusion, include the following configurations: a combination of two or more cortical bone portions optionally each having a patterned surface such that an interlocking fit between the bone portions is provided, and:

(a) a first cervical (flattened curved) cortical portion having a width of from about 2.0 mm to about 8.0 mm; a second cervical cortical bone portion having a width of from about 2.0 mm to about 8.0 mm; where the first portion is disposed on the second portion forming a graft unit, the graft unit is held together by at least two cortical bone pins having a diameter of from about 2.0 mm to about 4.0 mm, preferably 2.0 mm to about 3.0 mm; where the diameter of each pin is the same or different, the composite graft having a width of about 10.0 to about 20.0 mm, preferably about 16.0 mm, a diameter of about 10.0 mm to about 18.0 mm, preferably about 13.0 mm, and a centrally located hole, preferably from about 2.0 to about 8.0 mm in diameter, more preferably from about 3.0 to about 5.0 mm in diameter, disposed through the pinned graft unit, between at least two pins. Each of the top and bottom surfaces of the cervical fusion graft, from a side view, may be sloped at an angle of from about 0° to about 15°, preferably at an angle of from about 3° to about 10°, and most preferably one of the top or bottom surfaces sloped at an angle of about 7° with the other surface not sloped, along the top and bottom faces of the graft from the curved top end to the flattened bottom end as shown in FIGS. 14 and 15, to form the wedge shape. The anterior composite width at the flattened end is preferably from about 6.0 to about 8.0 mm. The top and bottom opposing faces of the cervical graft may optionally be textured, preferably with a plurality of pyrimidal protrusions, (b) a first cervical (flattened curved) cortical portion having a width of from about 2.0 mm to about 8.0 mm; a second cervical cortical bone portion having a width of from about 2.0 mm to about 8.0 mm; where the first portion is disposed on the second portion forming a graft unit, the graft unit is held together by at least two cortical bone pins having a diameter of from about 2.0 mm to about 4.0 mm, preferably 2.0 mm to about 3.0 mm; where the diameter of each pin may be the same or different, the composite graft having width of about 15.0 to about 25.0 mm, preferably about 19.0 mm, a diameter of about 12.0 mm to about 20.0 mm, preferably about 15.0 mm, and a centrally located hole disposed through the pinned graft unit, between at least two pins. The cervical fusion graft, from a side view, is preferably sloped at an angle of from about 3° to about 15°, preferably at an angle of about 7° along the top and bottom faces, or an angle of 0° along the top surface and an angle of 7° along the bottom surface , of the graft from the curved end to the flattened end as shown in FIGS. 14 and 15, to form the wedge shape. The anterior composite width at the flattened end is preferably from about 6.0 to about 8.0 mm. The top and bottom opposing faces of the cervical graft may optionally be textured, preferably with a plurality of pyrimidal protrusions, (c) a first and a second cervical (flattened curved) cortical bone portion, the first bone portion disposed on the second bone portion to form a graft unit, the graft unit is held together by at least two cortical bone pins having a diameter of from about 2.0 mm to about 4.0 mm, and having the following preferred configurations: a posterior composite width of from 5.0 mm to 15.0 mm, preferably from about 8.0 mm to 10.0 mm , an anterior composite width of from about 5.0 mm to about 10.0 mm, preferably from about 6.0 mm to about 8.0 mm,; the composite graft having a width of from about 12.0 to about 25.0 mm, preferably from about 16.0 mm to about 19.0 mm, a diameter of from about 10.0 mm to about 20.0 mm, preferably from about 13.0 mm to about 15.0 mm, and a centrally located hole dispose through the pinned graft unit, between at least two pins. The graft, from a side view, is preferably sloped at an angle of from about 3° to about 15°, preferably at an angle of about 7°, or angle of 0° along the top surface and an angle of 7° along the bottom surface, along the top and bottom faces of the graft from the curved end to the flattened end as shown in FIGS. 14 and 15, to form the wedge shape. The top and bottom opposing faces of the cervical graft may optionally be textured, preferably with a plurality of pyrimidal protrusions; and (d) two or more bone portions preferably cortical bone portions, layered to form a graft unit, where the bone portions are connected by: being configured to interlock with each other where the interlocking is self-locking or is locked with one or more pins entirely or partially traversing a dimension of the graft, and/or at least two cortical bone pins having a diameter of from about 2.0 mm to about 4.0 mm and having the following referred configurations: (I) a diameter of about 14.0 mm; a width of about 17.5 mm; a pin diameter of about 2.5 mm; a through-hole having a diameter of about 6.5 mm, a first width of about 9.0 mm, and a second width of about 4.0 mm; a distance from the arc to a pin and from the through-hole to the second width of the graft, of about 2.0 mm; a second width of about 10.0 mm, and the graft having its sides sloped at an angle of about 25° (see FIG. 44); and (ii) a diameter of about 12.0 mm; a width of about 14.5 mm; a pin diameter of about 2.5 mm; a through-hole having a diameter of about 4.0 mm; a distance from the arc to a pin and from the through-hole to the second width of the graft, and from the pin to the through-hole, of about 2.0 mm; a second width of about 7.75 mm, and the graft having its sides sloped at an angle of about 25° (see FIG. 43).

Most preferable anterior lumbar oval wedge composite bone grafts include the following configurations: (a) two or more ovoid cortical bone portions disposed on each other thereby forming a graft unit having a composite posterior width of from about 5.0 mm to about 20.0 mm, preferably from about 1.0 mm to about 15.0 mm, an anterior composite width of from 5.0 mm to about 20.0 mm, preferably from about 8.0 mm to about 14.0 mm, a height of from about 15.0 mm to about 30.0 mm, preferably from about 21.0 mm to about 28.0 mm, and a length of from about 23.0 mm to about 45.0 mm, preferably from about 32.0 mm to about 42.0 mm; the graft unit is held together by at least two cortical bone pins having a diameter of from about 2.0 mm to about 4.0 mm, where the pins have the same or a different diameter, to form a pinned graft unit; and optionally one or more through-holes disposed through the pinned graft unit. The graft, from a side view, is preferably sloped at an angle of from about 3° to about 15°, preferably at an angle of about 7°, or an angle of 0° along the top surface and an angle of 7° along the bottom surface, along the top and bottom faces of the to form the wedge shape. Th top and bottom opposing faces of the cervical graft may optionally be textured.

Any one or more of the cortical and/or cancellous bone portions of the above-described composite bone grafts, may optionally be demineralized and/or discontinuous, depending upon the particular clinical application. For example, any one or more bone portions of any composite graft may include for example, one or more horzontally disposed channels, vertically disposed channels or randomly disposed channels, partially or completely traversing the height and/or width of the graft. One of ordinary skill in the art to which the present invention pertains can readily select, make and employ, a particular composite graft, without undue experimentation.

V. Surgical Inplantation and Indications

The present composite bone graft is useful for implantation in patients suffering from defects caused by congenital anomaly, disease, or trauma, including for example, spine fractures; deformity, e.g. kyphotic deformities, e.g. posttraumatic kyphosis; postlaminectomy kyphosis, junctional kyphosis, and Scheuermann's kyphosis; scoliosis, e.g. neuromuscular scoliosis, adult scoliosis, paralytic scoliosis, congenital and syndromic scoliosis; and cervical neck pain. Surgical methods for correcting degenerative conditions, for example in the lumbar spine, include decompression (excision of disc material, hypertrophied bone, or ligament along with fusion, or fusion alone.

A posterior surgical approach is preferably used. The choice of approach is dictated by the site of primary pathology and the physical size of the composite bone graft. Pathology that involves vertebral bodies is best approached anteriorly through the thorax, abdomen or flank. Pathology involving posterior elements are best approached posteriorly for example, through a vertical midline approach or posterior lateral muscle spinning approach.

Those of ordinary skill in the art to which the present invention pertain, including for example an orthopedic surgeon and a spinal surgeon, can readily select and employ a particular composite bone graft, without undue experimentation. Factors to be considered in such selection and employment include: the type and size of graft bone, its anatomic site of fusion, and the age of the patient. An ideal graft, for example for use in lumbar interbody fusion, should be: osteoinductive, non-immunogenic, provide immediate mechanical stability, and be appropriately sized and shaped for the particular application/patient. Indications, diagnostic criteria, graft selection and surgical technique, are factors that can be readily selected, optimized and employed by those of ordinary skill in the art without undue experimentation, and are discussed in: Master Techniques in Orthopedic Surgery, The Spine, edited by Bradford, David S., Lippincott-Raven, ISBN 0-7817-0033-7, Philadelphia, Pa, (1997), hereby incorporated herein by reference in its entirety. When implanting a cervical fusion graft, an anterior cervical approach is used.

The following examples are illustrative only, and do not in any way limit the scope of the invention.

EXAMPLES

I. Preparation of a Composite Graft.

Donor bone was harvested according to industry accepted standards from a cadaver donor. The composite bone grafts, sized as recorded in Table 1, were prepared according to the method described as follows. Using a bandsaw cortical planks and pin segments were cut from a cortical shaft. One surface of each cortical planks was smoothed on a planing table and the planks were cut to the recorded thickness using a mill. Thereafter, using a table saw, the cut planks were cut to the recorded width and length. Cortical pins were then cut using a drill press, from the pin segments. Using a drill sander, the cortical pins were tapered sufficient to allow insertion into the reamed graft unit. Next, using a bandsaw, cancellous wafers were cut from cancellous bone to the recorded thickness. The wafers were then cut to the recorded width and length using a table saw. The cortical planks and cancellous wafer were then assembled into a graft unit in a jig and were then reamed using a drill press. The anterior through-hole was disposed through the width of the graft unit at the though-hole's center point, 7.5 mm along the length of the graft unit, and centered relative to the with of the graft unit. Using an arbor press, the cortical pins were pushed into the reamed graft unit to produce a pinned graft unit. Any excess pin was then cut off using a bandsaw. Next, using a drill sander, the pinned graft unit was then shaped to the final recorded width, and if the composite graft angled, the pinned graft was then milled to cut angles. The composite graft was milled to provide grooves of the recorded height, on the opposing surfaces as shown in the Figures. The produced composite bone grafts were then cleaned and tested as follows.

TABLE 1

| Specimen | | Composite width | Tooth (mm) | | Height (mm) | | Length | Pins (mm) | | Cancellous* width | Cortical* width |
|---|---|---|---|---|---|---|---|---|---|---|---|
| number | Graft Type | (mm) | Height | angle | front | back | (mm) | front | back | (mm) | (mm) |
| 1 | trapezoid wedge (TA) | 9.0 | 1.2 | 60.0° | 8.0 | 10.0 | 21.0 | 2.5 | 3.0 | 3.0 | 3.0 |
| 2 | trapezoid wedge (TB) | 11.0 | 1.5 | 60.0° | 10.0 | 12.0 | 21.0 | 3.0 | 3.0 | 5.0 | 3.0 |
| 3 | trapezoid wedge (TC) | 13.0 | 1.5 | 60.0° | 12.0 | 14.0 | 21.0 | 3.0 | 3.0 | 5.0 | 4.0 |
| 4 | trapezoid wedge (TD) | 13.0 | 1.5 | 60.0° | 12.0 | 14.0 | 21.0 | 3.0 | 3.0 | 5.0 | 4.0** |
| 5 | parallel block (PA) | 7.0 | 1.2 | 60.0° | 9.0 | 9.0 | 21.0 | 2.5 | 2.5 | 3.0 | 2.0 |
| 6 | parallel block (PB) | 9.0 | 1.2 | 60.0° | 9.0 | 9.0 | 21.0 | 2.5 | 2.5 | 3.0 | 3.0 |
| 7 | parallel block (PC) | 9.0 | 1.2 | 60.0° | 11.0 | 11.0 | 21.0 | 3.0 | 3.0 | 3.0 | 3.0 |
| 8 | parallel block (PD) | 9.0 | 1.2 | 60.0° | 10.0 | 10.0 | 21.0 | 2.5 | 3.0 | 3.0 | 3.0 |
| 9 | parallel block (PE) | 11.0 | 1.5 | 60.0° | 13.0 | 13.0 | 21.0 | 3.0 | 3.0 | 5.0 | 3.0 |
| 10 | parallel block (PF) | 11.0 | 1.5 | 60.0° | 12.0 | 12.0 | 21.0 | 3.0 | 3.0 | 5.0 | 3.0 |
| 12 | parallel block (PG) | 13.0 | 1.5 | 60.0° | 14.0 | 14.0 | 21.0 | 3.0 | 3.0 | 5.0 | 4.0** |
| 11 | parallel block (PH) | 11.0 | — | — | 9.0 | 9.0 | 21.0 | 3.0 | 3.0 | 5.0 | 3.0 |
| 12 | parallel block (PI) | 11.0 | — | — | 9.0 | 9.0 | 21.0 | 3.0 | 3.0 | 3.0 | 4.0** |
| 13 | parallel block (PJ) | 9.0 | — | — | 7.0 | 7.0 | 21.0 | 2.5 | 2.5 | 3.0 | 3.0 |

*+0.500 mm or −0.250 mm
**two (2) cortical planks were used, each −2.0 mm to give a composite cortical width of 4.0 mm II. Biomechanical Strength The biomechanical strength of the composite bone grafts recorded in Table 2 was determined ing static compression testing. All of the tested bone grafts were produced as set forth in Example 1, and sized as recorded. All of the composite bone grafts were constructed from two cortical layers sandwiching a cancellous layer with all of the layers oriented parallel to the sagittal plane, and secured together with two cortical bone pins. Tests were performed under a compressive load using an Instron™ 4204 test machine. An axial displacement was applied in a ramp fashion at 2.5 mm/min rate until catastrophic failure of the bone graft occurred or until the maximum displacement of 3 mm was reached. Data was collected at a rate 2 Hz.

As can be seen from the data set forth in Table 2, all of the composite grafts exhibited adequate to exceptional biomechanical strength, as compared to the vertebral body itsel which fails at 10,000 N (2,200 lbs).

two 3.0 mm cortical layers sandwiching a 3.0 mm cancellous layer, were produced. After production, the grafts were either fresh frozen or freeze-dried. Table 3 summarizes the compression test results of fresh frozen composite graft after thawing in 9.0% saline solution for 90 minutes and the freeze-dried composite bone grafts after soaking for 20 min., 60 min., and 7 days in 9.0% saline solution.

Test results showed that the 20 minute soaked freeze-dried grafts had the highest strength (Table 3) and stiffness (Table 4) among all the tested groups. Generally, strength and stiffness of the fresh-frozen grafts were relatively lower than the freeze-dried grafts.

TABLE 2

| Graft Type | Specimen number | Load at Max. Load (KN) | Displacement at Max. Load (Mm) | Load at z-sip, yield (Mm) | Displacement at z-sip, yield (Mm) | Stiffness (slope) (Aut Young) (N/mm) |
|---|---|---|---|---|---|---|
| PA | PA-1 | 8.464 | 3.460 | 6.719 | 1.706 | 6708.0 |
| (Donor 1) | PA-2 | 8.923 | 2.450 | 8.625 | 1.957 | 6544.0 |
| | PA-3 | 8.569 | 3.020 | 7.323 | 1.851 | 6201.0 |
| | PA-4 | 7.238 | 3.070 | 6.727 | 1.998 | 4756.0 |
| | PA-5 | 8.395 | 2.160 | 8.078 | 1.873 | 7321.0 |
| Mean (Donor 1): | | 8.318 | 2.832 | 7.495 | 1.877 | 6306 |
| Std. Dev. (Donor 1): | | .637 | .521 | .842 | .113 | 957 |
| (Donor 2) | PA-6 | 9.718 | 3.300 | 6.636 | 1.560 | 5637.0 |
| | PA-7 | 8.118 | 1.970 | 8.113 | 1.956 | 6379.0 |
| | PA-8 | 11.190 | 3.150 | 9.052 | 2.102 | 6246.0 |
| | PA-9 | 8.201 | 2.110 | 8.193 | 2.102 | 6643.0 |
| | PA-10 | 5.992 | 1.430 | 5.882 | 1.248 | 7973.0 |
| | PA-11 | 7.248 | 2.500 | 7.130 | 2.060 | 6578.0 |
| | PA-12 | 8.319 | 2.660 | 8.228 | 2.123 | 6500.0 |
| | PA-13 | 6.325 | 2.690 | 5.782 | 1.624 | 4518.0 |
| | PA-14 | 7.973 | 1.770 | 7.970 | 1.749 | 5867.0 |
| | PA-15 | 8.969 | 2.750 | — | — | 5546.0 |
| Mean (Donor 2): | | 8.205 | 2.433 | — | — | 6189.0 |
| Std. Dev. (Donor 2): | | 1.535 | .601 | — | — | 900.0 |
| (Donor 3) | PA-16 | 7.259 | 1.540 | 7.256 | 1.541 | 8207.0 |
| (Donor 4) | PA-17 | 9.799 | 1.710 | 9.799 | 1.687 | 9930.0 |
| | PA-18 | 7.879 | 1.640 | 7.876 | 1.623 | 7963.0 |
| | PA-19 | 9.590 | 1.620 | 9.584 | 1.603 | 9794.0 |
| | PA-20 | 9.388 | 1.670 | 9.380 | 1.665 | 8773.0 |
| | PA-21 | 9.617 | 1.750 | 9.617 | 1.748 | 10260.0 |
| Mean (Donor 4): | | 9.255 | 1.678 | 9.251 | 1.655 | 9344.0 |
| Std. Dev. (Donor 4) | | .783 | .053 | .783 | .057 | 950 |
| PC | PC-1 | 9.165 | 4.000 | 7.216 | 1.811 | 10230.0 |
| (Donor 5) | PC-2 | 7.664 | 2.860 | 7.664 | 2.853 | 4291.0 |
| | PC-3 | 8.360 | 2.810 | 8.338 | 2.791 | 4226.0 |
| | PC-4 | 8.612 | .970 | 8.607 | .958 | 19260.0 |
| Mean (Donor 5): | | 8.450 | 2.660 | 7.956 | 2.103 | 9503.0 |
| Std. Dev. (Donor 5): | | .623 | 1.254 | .633 | .900 | 7090.0 |
| (Donor 6) | PC-5 | 10.45 | 2.040 | 10.36 | 1.540 | 9482.0 |
| | PC-6 | 10.17 | 2.140 | 10.17 | 2.144 | 7261.0 |
| | PC-7 | 11.74 | 2.090 | 11.73 | 2.060 | 10330.0 |
| | PC-8 | 11.77 | 2.290 | 11.76 | 2.290 | 9123.0 |
| Mean (Donor 6): | | 11.03 | 2.140 | 11.01 | 2.009 | 9049.0 |
| Std. Dev. (Donor 6): | | .84 | .108 | .86 | .326 | 1295.0 |
| PB | PB-1 | 8.953 | 1.540 | 8.604 | 1.310 | 10160.0 |
| (Donor 7) | PB-2 | 10.910 | 1.850 | 10.910 | 1.852 | 10380.0 |
| Mean (Donor 7): | | 9.931 | 1.695 | 9.758 | 1.581 | 10270.0 |
| Std. Dev. (Donor 7): | | 1.336 | .219 | 1.632 | .383 | 156.0 |
| PE | PE-1 | 11.42 | 1.810 | 11.21 | 1.601 | 13900.0 |
| (Donor 8) | | | | | | |

III. Comparative Biomechanical Strength

Composite bone grafts were produced as described in Example A. 11×9×21 mm grafts: (PH) having two 3.0 mm cortical layers sandwiching a 5.0 mm cancellous layer, and (PI) having two 4.0 mm cortical layers sandwiching a 3.0 mm cancellous layer; and 9×7×21 mm grafts (PJ) having The inventive composite bone graft, both fresh-frozen and freeze-dried, when compared to commercially available bone graft produce (Os™ and Mid America) was significantly stronger. See Brantigan et al, Compression Strength of Donor Bone for Posterior Lumbar Interbody Fusion, Spine Vol. 18, No. 9, 1993.

TABLE 3

| Graft Type | Specimen Number | | | | | Mean | Std. Dev. |
|---|---|---|---|---|---|---|---|
| | 1 | 2 | 3 | 4 | 5 | | |
| Fresh Frozen-one-hour (PH-1) | 9.114 | 9.160 | 6.942 | 6.945 | 9.852 | 8.403 | 1.364 |
| Fresh Frozen-one-hour (PH-2) | 9.176 | 8.744 | — | — | — | 8.960 | 0.305 |
| Freeze-dried-20.0 min. (PI-1) | 13.970 | 14.460 | — | — | — | 14.220 | 0.346 |
| Freeze-dried-one-hour (PI-2) | 13.99 | 13.97 | — | — | — | 13.98 | 0.014 |
| Freeze-dried-seven-days (PI-3) | 10.300 | 8.255 | — | — | — | 9.277 | 1.446 |
| Fresh Frozen-one-hour (PJ-1) | 7.925 | 7.973 | 8.958 | 7.836 | 9.799 | 8.498 | .985 |
| Fresh Frozen-one-hour (PJ-2) | 8.897 | 9.015 | — | — | — | 8.956 | .083 |
| Os ™* | 1.098 | .934 | 5.72 | 2.145 | — | 2.474 | 2.229 |
| Mid America Tricortical** | 2.823 | 1.699 | 1.926 | 2.629 | 2.464 | 2.308 | 0.477 |

*Os ™ bone is a commercial tricortical bone graft product.
**Mid America tricortical is a commercially available bone graft product produced by Mid America.

TABLE 4

| Graft Type | Specimen Number | | | | | Mean | Std. Dev. |
|---|---|---|---|---|---|---|---|
| | 1 | 2 | 3 | 4 | 5 | | |
| Fresh Frozen-one-hour (PJ-1) (9 × 7, 3-3-3) | 7053.0 | 6176.0 | 5878.0 | 5434.0 | 7528.0 | 6413.8 | 1103.4 |
| Fresh Frozen-one-hour (PJ-2) (9 × 7, 3-3-3) | 7303.0 | 6112.0 | — | — | — | 6707.5 | 842.2 |
| Fresh Frozen-one-hour (PH-1) (11 × 9, 3-5-3) | 10980.0 | 13900.0 | — | — | — | 12440.0 | 2064.8 |
| Fresh Frozen-one-hour (PH-2) (11 × 9, 3-5-3) | 4938.0 | 11340.0 | 11060.0 | 12180.0 | 9125.0 | 9728.0 | 2902.3 |
| Freeze-dried-20.0 min. (PI-1) (11 × 9, 4-3-4) | 27760.0 | 28420.0 | — | — | — | 28090.0 | 466.7 |
| Freeze-dried-one-hour (PI-2) (11 × 9, 4-3-4) | 21940.0 | 22890.0 | — | — | — | 22415.0 | 671.8 |
| Freeze-dried-seven-days (PI-3) (11 × 9, 4-3-4) | 14590.0 | 18130.0 | — | — | — | 16360.0 | 2503.2 |

IV. Preparation of a Cervical Wedge Composite Graft

Donor bone was harvested according to industry accepted standards from a cadaver donor. The composite bone grafts, sized as recorded in Table 5, were prepared according to the method described as follows. Using a bandsaw cortical planks and pin segments were cut from a cortical shaft. One surface of each cortical planks was smoothed on a planing table and the planks were cut to the required thickness using a mill. Thereafter, using a table saw, the cut planks were cut to the required width and length. Cortical pins were then cut using a drill press, from the pin segments. Using a drill sander, the cortical pins were tapered sufficient to allow insertion into the reamed graft unit. Next, the cortical planks were assembled into a graft unit in a jig and were then reamed using a drill press. Using an arbor press, the cortical pins were pushed into the reamed graft unit to produce a pinned unit. At this point, the pinned unit was optionally sloped at it's top and/or bottom surface, for example at its bottom surface, at 7° using a radial saw. A circular shape was then cut through the pinned and optionally sloped unit using a trephine or Cloward cutter of appropriate size. Thereafter, using a radial saw or a band saw, the sides and bottom of the graft were shaped, and a centrally located hole was drilled through the pinned unit. Any excess pin was then cut off using a bandsaw. Lastly, the pinned graft unit was smoothed. If textured, the composite graft was milled to provide grooves on the opposing surfaces as shown in FIG. 35.

TABLE 5

| Specimen number | Graft Type | Composite Width (mm) | | Diameter (Mm) | Width (Mm) |
|---|---|---|---|---|---|
| | | Front | back | | |
| 1. | Cervical Wedge (CA) | 6.0 | 10.0 | 13.0 | 160 |
| 2. | Cervical Wedge (CB) | 7.0 | 11.0 | 13.0 | 16.0 |
| 3. | Cervical Wedge (CC) | 8.0 | 12.0 | 13.0 | 16.0 |
| 4. | Cervical Wedge (CD) | 6.0 | 10.0 | 15.0 | 19.0 |
| 5. | Cervical Wedge (CE) | 7.0 | 11.0 | 15.0 | 19.0 |
| 6. | Cervical Wedge (CF) | 5.0 | 12.0 | 15.0 | 19.0 |
| 7. | Cervical Wedge (CG) | 6.0 | 6.0 | 13.0 | 16.0 |
| 8. | Cervical Wedge (CH) | 8.0 | 8.0 | 13.0 | 16.0 |
| 9. | Cervical Wedge (CI) | 6.0 | 6.0 | 15.0 | 19.0 |
| 10. | Cervical Wedge (CJ) | 7.0 | 7.0 | 13.0 | 16.0 |
| 11. | Cervical Wedge (CK) | 7.0 | 7.0 | 15.0 | 19.0 |

It is to be understood, however, that the scope of the present invention is not to be limited to the specific embodiments described above. The invention may be practiced other than as particularly described and still be within the scope of the accompanying claims.

We claim:

1. A composite bone graft, comprising:
 a first cortical bone portion;
 a second cortical bone portion;
 a cancellous bone portion disposed between said first cortical bone portion and said second cortical bone portion to form a graft unit; and
 one or more bone pins for holding together said graft unit, wherein said first cortical bone portion and said second cortical bone portion are not in physical contact, and wherein said composite bone graft does not comprise an adhesive and said bone graft is not demineralized.

2. A composite bone graft, consisting essentially of:
 a first cortical bone portion;
 a second cortical bone portion;
 a cancellous bone portion disposed between said first cortical bone portion and said second cortical bone portion to form a graft unit; and
 one or more bone pins for holding together said graft unit, wherein said first cortical bone portion and said second cortical bone portion are not in physical contact and said bone graft is not demineralized.

3. The composite bone graft of any one of claims 1 or 2, said composite bone graft is a composite trapezoid wedge, said composite trapezoid wedge comprising:
 a top textured surface;
 a bottom textured surface;
 an anterior height of from about 3.0 mm to about 30.0 mm;
 a posterior height of from about 5.0 mm to about 50.0 mm;
 a composite width of from about 4.0 mm to about 20.0 mm; and
 a length of from about 5.0 mm to about 50.0 mm, wherein textured surfaces are opposing and are disposed perpendicular to interfaces of said bone portions, said top textured surface and said bottom textured surface comprise a plurality of continuous linear protrusions defining a saw-tooth pattern.

4. The composite bone graft of any one of claims 1 or 2, said composite bone graft is a composite parallel block, said composite parallel block comprising:
 a top textured surface;
 a bottom textured surface;
 a height of from about 3.0 mm to about 30.0 mm;
 a composite width of from about 4.0 mm to about 20.0 mm; and
 a length of from about 5.0 mm to about 50.0 mm, wherein textured surfaces are opposing and are disposed perpendicular to interfaces of said bone portions, said top textured surface and said bottom textured surface comprise a plurality of continuous linear protrusions defining a saw-tooth pattern.

5. The composite bone graft of any one of claims 1 or 2, said composite bone graft is a composite cervical wedge, said composite cervical wedge comprising:
 a top textured surface;
 a bottom textured surface;
 an anterior height of from about 3.0 mm to about 30.0 mm;
 a posterior height of from about 5.0 mm to about 50.0 mm;
 a composite width of from about 4.0 mm to about 20.0 mm; and
 a length of from about 5.0 mm to about 50.0 mm, wherein textured surfaces are opposing and are disposed perpendicular to interfaces of said bone portions, said top textured surface and said bottom textured surface comprise a plurality of continuous linear protrusions defining a saw-tooth pattern.

6. The composite bone graft of any one of claims 1 or 2, said composite bone graft is a composite cervical block, said composite cervical block comprising:
 a top textured surface;
 a bottom textured surface;
 a height of from about 3.0 mm to about 30.0 mm;
 a composite width of from about 4.0 mm to about 20.0 mm; and
 a length of from about 5.0 mm to about 50.0 mm, wherein textured surfaces are opposing and are disposed perpendicular to interfaces of said bone portions, said top textured surface and said bottom textured surface comprise a plurality of continuous linear protrusions defining a saw-tooth pattern.

7. The composite bone graft of claim 3, said plurality of continuous protrusions having a height of from about 0.1 mm to about 5.0 mm.

8. The composite bone graft of claim 4, said plurality of continuous protrusions having a height of from about 0.1 mm to about 5.0 mm.

9. The composite bone graft of claim 5, said plurality of continuous protrusions having a height of from about 0.1 mm to about 5.0 mm.

10. The composite bone graft of claim 6, said plurality of continuous protrusions having a height of from about 0.1 mm to about 5.0 mm.

11. The composite bone graft of any one of claims 1 or 2, said first cortical bone portion comprises one or more cortical bone planks layered to form said first cortical bone portion, said second cortical bone portion comprises one or more cortical bone planks layered to form said second cortical bone portion, and said cancellous bone portion comprises one or more cancellous bone planks layered to form said cancellous bone portion.

12. The composite bone graft of any one of claims 1 or 2, comprising allogenic or xenogenic bone.

13. A composite bone graft comprising two or more distinct, adjacent, bone portions comprising at least one cancellous bone portion, layered to form a graft unit; one or more bone pins provided perpendicular to an interface between adjacent bone portions; and a first chamfered edge and a second chamfered edge, said first chamfered edge provided along a length of said composite bone graft at its top edge, and said second chamfered edge provided along a length of said composite bone graft at its bottom edge, such that the chamfered edges are diametrically opposed, wherein said composite bone graft does not comprise an adhesive, and said bone graft is not demineralized.

14. A composite bone graft comprising:
 one or more cortical bone portions layered to form a first unit;
 one or more cortical bone portions layered to form a second unit;
 one or more cancellous bone portions layered to form a third unit; said third unit disposed between said first and said second unit to form a graft unit and wherein one or more of said bone portions comprise a discontinuous bone portion;,
 one or more bone pins for holding together said graft unit said bone graft does not comprise an adhesive; and one or more therapeutically beneficial substances selected from the group consisting of: an osteoinductive material selected from the group consisting of: autograft bone, allograft bone, demineraized cortical bone, demineralized cancellous bone, discontinuous demineralized cortical bone, collagen comprising one or more growth factors selected from the group consisting of: bone morphogenic protein, and transforming growth factor-β; collagen comprising demineralized bone, cancellous bone, cortical bone, and a growth factor selected from the group consisting of: bone morphogenic protein, and transforming growth factor-β; an osteoconductive substance selected from the group consisting of: demineralized cortical bone, demineralized cancellous bone, discontinuous demineralized cortical bone, discontinuous cortical bone, collagen, cancellous bone, hydrpxyapitate, polymeric matrix material, bioglass, bioceramic, resorbable biomaterial, bioabsorbable polymer, a plastic matrix, stainless steel, titanium, and cobalchromium-molybdenum alloy matrix; and a pharmaceutically active agent selected from the group consisting of: a growth factor selected from the group consisting of: bone morphogenic protein, and transforming growth factor-β, a chemotherapeutic agent, an anti-inflammatory agent, and an antibiotic, and wherein said bone portions are not demineramized.

15. A composite bone graft, comprising:

a plurality of cortical bone portions;

a plurality of cancellous bone portions, where each of said cortical bone portions and each of said cancellous bone portions are alternately layered to form a graft unit; and one or more bone pins for holding together said graft unit, wherein said composite bone graft does not comprise an adhesive and said bone graft is not demineralized.

\* \* \* \* \*

(12) INTER PARTES REVIEW CERTIFICATE (2996th)
United States Patent (10) Number: US 6,458,158 K1
Anderson et al. (45) Certificate Issued: Feb. 15, 2023

(54) COMPOSITE BONE GRAFT, METHOD OF MAKING AND USING SAME

(75) Inventors: Billy G. Anderson; Llyod Wolfinbarger, Jr.

(73) Assignee: LIFENET HEALTH

Trial Number:

IPR2019-00569 filed Feb. 19, 2019

Inter Partes Review Certificate for:

Patent No.: 6,458,158
Issued: Oct. 1, 2002
Appl. No.: 09/699,029
Filed: Oct. 27, 2000

The results of IPR2019-00569 are reflected in this inter partes review certificate under 35 U.S.C. 318(b).

INTER PARTES REVIEW CERTIFICATE
U.S. Patent 6,458,158 K1
Trial No. IPR2019-00569
Certificate Issued Feb. 15, 2023

AS A RESULT OF THE INTER PARTES REVIEW PROCEEDING, IT HAS BEEN DETERMINED THAT:

Claims 1-15 are found patentable.

* * * * *